(12) United States Patent
Schneewind et al.

(10) Patent No.: US 6,773,706 B2
(45) Date of Patent: Aug. 10, 2004

(54) IDENTIFICATION OF SORTASE GENE

(75) Inventors: Olaf Schneewind, Los Angeles, CA (US); Sarkis Mazmanian, Sherman Oaks, CA (US); Gwen Liu, Los Angeles, CA (US); Hung Ton-That, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/933,999

(22) Filed: Aug. 21, 2001

(65) Prior Publication Data

US 2003/0022178 A1 Jan. 30, 2003

Related U.S. Application Data

(63) Continuation-in-part of application No. 09/292,437, filed on Apr. 15, 1999.

(51) Int. Cl.$^7$ .................. A61K 39/00; A61K 39/02; A61K 39/385; C12N 9/48; C07K 1/00

(52) U.S. Cl. .................. 424/185.1; 424/190.1; 424/192.1; 424/193.1; 424/234.1; 424/243.1; 435/183; 435/191; 435/212; 435/220; 530/350

(58) Field of Search .................. 424/185.1, 190.1, 424/192.1, 193.1, 234.1, 243.1; 530/350; 435/183, 191, 212, 220

(56) References Cited

FOREIGN PATENT DOCUMENTS

WO    WO 00/62804    10/2000

OTHER PUBLICATIONS

Brocklehurst, Keith, "Specific covalent modification of thiols: applications in the study of enzymes and other biomolecules" *Int. J. Biochem.* 10:259–274 (1979).

Hook et al., "Proteases and the emerging role of protease inhibitors in prohormone processing" *FASEB Journal* 81269–1278 (Dec. 1994).

Klein et al., "Cloning and nucleotide sequence analysis of the *Lactobacillus delbrueckil* ssp. Lactis DSM7290 cysteine aminopeptidase gene pepC" *FEMS Microbiology Letters* 124:291–300 (1994).

Kyte et al., "A Simple Method for Displaying the Hydropathic Character of a Protein" *J. Mol. Biol.* (1982) 157:105–102 (1982).

Stucky et al., "Cloning and DNA sequence analysis of pepQ, a prolidase gene from *Lactobacillus delbrueckii* subsp. Lactis DSM7290 and partial characterization of its product" *Mol Gen Genet* 247:4940500 (1995).

G.P. Smith, "Filamentous Fusion Phage: Novel Expression Vectors that Display Cloned Antigens on the Virion Surface," *Science* 228:1315–1316 (1985).

J.A. Javitch et al., "Mapping the Binding Site Crevice of the Dopamine D2 Receptor by the Substituted–Cysteine Accessibility Method," *Neuron* 14: 825–831 (1995).

M.H. Akabas & A. Karlin, "Identification of Acetylcholine Receptor Channel–Lining Residues in the M1 Segment of the α–Subunit," *Biochemistry* 34: 12496–12500 (1995).

D.J. Smith et al., "Simple Alkanethiol Groups for Temporary Blocking of Sulfhydryl Groups of Enzymes," *Biochemistry* 14: 766–771 (1975).

W.N. Valentine & D.E. Paglia, "Effect of Chemical Modification of Sulfhydryl Groups of Human Erythrocyte Enzymes," *Am. J. Hematol.* 11: 111–124 (1981).

R.P. Novick, "Genetic Systems in Staphylococci," *Meth. Enzymol.* 204: 587–636 (1991).

O. Schneewind et al., "Sorting of Protein A to the Staphylococcal Cell Wall," *Cell* 70: 267–281 (1992).

O. Schneewind et al., "Cell Wall Sorting Signals in Surface Proteins of Gram–Positive Bacteria," *EMBO J.* 12:4803–4811 (1993).

E. Dufour et al., "Peptide Aldehydes and Nitriles as Transition State Analog Inhibitors of Cysteine Proteases," *Biochemistry* 34: 9136–9143 (1995).

J. O. Westerik & R. Wolfenden, "Aldehydes as Inhibitors of Papain," *J. Biol. Chem.* 247: 8195–8197 (1972).

L Björck et al., "Bacterial Growth Blocked by a Synthetic Peptide Based on the Structure of a Human Proteinase Inhibitor," *Nature* 337: 385–386 (1989).

P.A. Bartlett & C.K. Marlowe, "Phosphonamidates as Transition–State Analogue Inhibitors of Thermolysin," *Biochemistry* 22: 4618–4624 (1983).

(List continued on next page.)

Primary Examiner—Mark Navarro
(74) Attorney, Agent, or Firm—Ginger R. Dreger; Heller Ehrman White & McAuliffe LLP

(57) ABSTRACT

The present invention is a substantially purified sortase-transamidase enzyme from Gram-positive bacteria, such as *Staphylococcus aureus*. The enzyme having a molecular weight of about 23,539 or about 29,076 daltons and catalyzing a reaction that covalently cross-links the carboxyl terminus of a protein having a sorting signal to the peptidoglycan of a Gram-positive bacterium, the sorting signal having: (1) a motif of $LPX_3X_4G$ therein; (2) a substantially hydrophobic domain of at least 31 amino acids carboxyl to the motif; and (3) a charged tail region with at least two positively charged residues carboxyl to the substantially hydrophobic domain, at least one of the two positively charged residues being arginine, the two positively charged residues being located at residues 31–33 from the motif, wherein $X_3$ is any of the twenty naturally-occurring L-amino acids and $X_4$ is selected from the group consisting of alanine, serine, and threonine, and wherein sorting occurs by cleavage between the fourth and fifth residues of the $LPX_3X_4G$ motif. Variants of the enzyme, methods for cloning the gene encoding the enzyme and expressing the cloned gene, and methods of use of the enzyme, including for screening for antibiotics and for display of proteins or peptides on the surfaces of Gram-positive bacteria, are also disclosed.

10 Claims, 23 Drawing Sheets

OTHER PUBLICATIONS

R.F. Pratt, "Inhibition of a Class C β–Lactamase by a Specific Phosphonate Monoester," *Science* 246: 917–919 (1989).

J.V. Moroney et al., "The Distance Between Thiol Groups in the γ Subunit of Coupling Factor 1 Influences the Proton Permeability of Thylakoid Membranes," *J. Bioenerget. Biomembr.* 14: 347–359 (1982).

A.N. Chatterjee & J.T. Park, "Biosynthesis of Cell Wall Mucopeptide by a Particulate Fraction from *Staphylococcus aureus*," *Proc. Natl. Acad. Sci. USA* 51:9–16 (1964).

M. Matsuhashi et al., "Incorporation of Glycine into the Cell Wall Glycopeptide in *Staphylococcus aureus*: Role of sRNA and Lipid Intermediates," *Proc. Natl. Acad. Sci. USA* 54:587–594 (1965).

D.B. Smith & K.S. Johnson, "Single–Step Purification of Polypeptides Expressed in *Escherichia coli* as Fusions with Glutathione S–Transferase," *Gene* 67: 31–40 (1988).

P.Z. Wang et al., "Nucleotide sequence of β–lactamase regulatory genes from staphylococcal plasmid p1258," *Nucl. Acids Res.* 19:4000–(1991).

P. Recsei et al., "Cloning, Sequence, and Expression of the Lysostaphin Gene from *Staphylococcus simulans*," Proc. Natl. Acad. Sci. USA 84:1127–1131 (1987).

K. Brocklehurst et al., "Cysteine Proteases," in *New Comprehensive Biochemistry, vol. 16: Hydrolytic Enzymes* (A. Neuberger & K. Brocklehurst, eds., Elsevier, New York, 1987), ch. 2, pp. 39–158.

B.L.M. de Yonge et al., "Peptidoglycan Composition of a Highly Methicillin–resistant *Staphylococcus aureus* Strain," *J. Biol. Chem.* 267: 11248–(1992).

U. Kopp et al., "Staphylococcal Peptidoglycan Interpeptide Bridge Biosynthesis: A Novel Antistaphylococcal Target?" *Microb. Drug Resist.* 2: 29–(1996).

D. Boothby et al., "A Rapid, Quantitative, and Selective Estimation of Radioactively Labeled Peptidoglycan in Gram–Positive Bacteria," *Anal. Biochem.* 44: 645 (1971).

H. Ton–That et al., "Anchor Structure of Staphylococcal Surface Proteins," *J. Biol. Chem.* 272: 22285–22292 (1997).

K. Yokogawa et al., "Mutanolysin, Bacteriolytic Agent for Cariogenic Streptococci: Partial Purification and Properties," *Antimicrob. Agents Chemother.* 6: 156–(1974).

W.W. Navarre et al., "Multiple Enzymatic Activities of the Murein Hydrolase from Staphylococcal Phage φ11," *J. Biol. Chem.* 274: in press (1999).

W.W. Navarre et al., "Anchor Structure of Staphylococcal Surface Proteins," *J. Biol. Chem.* 273:29135–(1998).

D.J. Smith et al., "Simple Alkanethiol Groups for Temporary Blocking of Sulfhydryl Groups of Enzymes," *Biochemistry* 14: 766–771 (1975).

W. W. Navarre and O. Schneewind, "Surface Proteins of Gram–Positive Bacteria and Mechanisms of Their Targeting to the Cell Wall Envelope," *Microbiol. Mol. Biol. Rev.* 63: 174 (1999).

M.K. Yeung et al., "Identification of a Gene Involved in Assembly of *Actinomyces naeslundii* T14V Type 2 Fimbriae," *J. Bacteriol.* 66: 1482–(1998).

M. K. Yeung and J. O. Cisar, "Sequence Homology between the Subunits of Two Immunologically and Functionally Distinct Types of Fimbriae of Actinomyces spp.," *J. Bacteriol.* 172: 2462–(1990).

D.B. Oliver et al., "Azide–resistant mutants of *Escherichia coli* alter the SecA protein, an azide–sensitive component of the protein export machinery," *Proc. Natl. Acad. Sci. USA* 87: 8227–8231 (1990).

I. van de Rijn and V.A. Fischetti, "Immunochemical Analysis of Intact M Protein Secreted from Cell Wall–Less Streptococci," *Infect. Immun.* 32: 86–91 (1981).

J. Movitz, "Formation of Extracellular Protein A by *Staphylococcus aureus*," *Eur. J. Biochem.* 68:291–299 (1976).

P. Lawrence and J. L. Strominger, "Biosynthesis of the Peptidoglycan of Bacterial Cell Walls," *J. Biol. Chem.* 245: 3653 (1970).

J.W. Kozarich et al., "Hydroxylaminolysis of Pencillin Binding Components is Enzymatically Catalyzed," *J. Biol. Chem.* 252: 7525–(1977).

G.T. Wang et al., *Tetrahedron Lett.* 31: 6493–6496 (1990).

E.D. Matayoshi et al., "Novel Fluorogenic Substrates for Assaying retroviral Proteases by Resonance Energy Transfer," *Science* 247: 954–(1989).

R. Pathak et al., "Sulfhydryl Modification of the Yeast Wbp1p Inhibits Oligosaccharyl Transferase Activity," *Biochemistry* 34: 4179–(1995).

W.W. Navarre & O. Schneewind, "Proteolytic Cleavage and Cell Wall Anchoring at the LPXTG Motif of Surface Proteins in Gram–Positive Bacteria," *Mol. Microbiol.* 14: 115–121 (1994).

C.A. Schindler & V.T. Schuhardt, "Lysostaphin: A New Bacteriolytic Agent for the Staphylococcus," *Proc. Natl. Acad. Sci. USA* 51: 414–421 (1964).

O. Schneewind et al., "Structure of the Cell Wall Anchor of Surface Proteins in *Staphylococcus aureus*," *Science* 268: 103–106 (1995).

O. Schneewind et al., "Cell Wall Sorting Signals in Surface Protein of Gram–Negative Bacteria," *EMBO J.* 12: 4803–4811 (1993).

I. van de Rijn & R.E. Kessler, "Growth Characteristics of Group A Streptococci in a New Chemically Defined Medium," *Infect. Immun.* 27:444–448 (1980).

W.W. Navarre et al., "Cell Wall Sorting of Lipoproteins in *Staphylococcus aureus*," *J. Bacteriol.* 178: 441–446 (1996).

S.R. Talay et al., "Domain Structure and Conserved Epitopes of Sfb Protein, the Fibronectin–Binding Adhesin of *Streptococcus pyogenes*," *Mol. Microbiol.* 13: 531–539 (1994).

M.P. Schreuder et al., "Targeting of a Heterologous Protein to the Cell Wall of *Saccharomyces cerevisiae*," *Yeast* 9: 399–409 (1993).

J.A. Ogier et al., "A 40–Kilodalton Cell Wall Protein–Coding Sequence Upstream of the sr Gene of *Streptococcus mutans*," *Infect. Immun.* 59: 1620–1626 (1991).

A. Rambukkana et al., "Identification and Characterization of Epitopes Shared Between the Mycobacterial 65–Kilodalton Heat Shock Protein and the Actively Secreted Antigen 85 Complex: Their In Situ Expression on the Cell Wall Surface of *Mycobacterium leprae*," *Infect. Immun.* 11: 4517–4527 (1992).

Cregg et al., "Molecular cloning and expression of the spsB gene encoding an essential type 1 signal peptidase from *Staphylococcus aureus*" *J. Bacteriol.* 178:5712–5718 (1996).

Dalbey et al., "Leader peptidase catalyzes the release of exported proteins from the outer surface of the *Escherichia coli* plasma membrane" *J. Biol. Chem.* 260:15925–15931 (1985).

Dhar et al., "Anchor structure of cell wall surface proteins in *Listeria monocytogenes*" *Biochemistry* 39:3725–3733 (2000).

Duong et al., "Biogenesis of the gram–negative bacterial envelope" *Cell* 91:567–573 (1997).

Duong et al., "The SecDFYajCdomain of preprotein translocase controls preprotein movement by regulating SecA membrane cycling" *EMBO J.* 16:4871–4879 (1997).

Fischetti et al., "Conservation of a hexapeptide sequence in the anchor region of surface proteins from gram–positive cocci" *Mol. Microbiol.* 4:1603–1605 (1990).

Flock, J.I. "Extracellular–matrix–binding proteins as targets for the prevention of *Staphylococcus aureus* infections" *Mol. Med. Today* 5:532–537 (1999).

Flock et al., "Cloning and expression of the gene for a fibronectin–binding protein from *Staphylococcus aureus*" *EMBO J.* 6:2351–2357 (1987).

Foster et al., "Surface protein adhesins of *Staphylococcus aureus*" *Trends Microbiol.* 6:484–488 (1998).

Giesbrecht et al., "staphylococcal cell wall: morphogenesis amd fatal variations in the presence of penicillin" *Microbiol. Mol. Biol. Rev.* 62:1371–1414 (1998).

Guss et al., "Region X, the–cell–wall–attachment part of staphylococcal protein" *A. Eur. J. Biochem.* 138:413–420 (1984).

Jönsson et al., "Two different genes encode fibronectin binding proteins in *Staphylococcus aureus*. The complete nucleotide sequence and characterization of the second gene." *Eur. J. Biochem.* 202:1041–1048 (1991).

Josefsson et al., "Three new members of the serine–aspartate repeat protein multigene family of *Staphylococcus aureus*" *Microbiol.* 144:3387–3395 (1998).

Kandler et al., "Cell wall polymers in archaea (archaebacteria)" *Cell Mol. Life Sci.* 54:305–308 (1998).

Kunst et al., "The complete genome sequence of the gram-positive bacterium *Bacillus subtilis*" *Nature* 390:249–256 (1997).

Lowy, F.D. "*Staphylococcus aureus* infections" *New Engl. J. Med.* 339:520–532 (1998).

Matsuhashi, M. "Utilization of lipid–linked precursors and the formation of peptidoglycan in the process of cell growth and division: membrane enzymes involved in the final steps of peptidoglycan synthesis and the mechanism of their regulation" in Ghuysen, J.M. and Hakenbeck, R. (eds.) *Bacterial Cell Wall,* Elsevier Biochemical Press, Amsterdam 55–72 (1994).

Mazmanian et al., "*Staphylococcus aureus* mutants defective in the display of surface proteins and in the pathogenesis of animal infections" *Proc. Natl. Acad. Sci. USA* 97:5510–5515 (2000).

Mazmanian et al., "*Staphylococcus aureus* sortase, an enzyme that anchors surface proteins to the cell wall" *Science* 285:760–763 (1999).

McDevitt et al., "Molecular characterization of the clumping factor (fibrinogen receptor) of *Staphylococcus aureus*" *Mol. Microbiol.* 11:237–248 (1994).

Miller et al. "Interaction of E. coli Ffh/4.5S ribonucleoprotein and FtsY mimics that of mammalian signal recognition particle and its receptor" *Nature* 367:657–659 (1994).

Nakagawa et al., "Functional biosynthesis of cell wall peptidoglycan by polymorphic bifunctional polypeptides. Penicillin–binding protein 1Bs of *Escheria coli* with activities of transglycosylase and transpeptidase." *J. Biol. Chem.* 259:13937–13946 (1984).

Ni Eidhin et al., "Clumping factor B (ClfB), a new surface–located fibrinogen–binding adhesin of *Staphylococcus aureus*" *Mol. Microbiol.* 30:245–257 (1998).

Patti et al., "The *Staphylococcus aureus* collagen adhesin is a virulence determinant in experimental septic arthritis" *Infect. Immun.* 62:152–161 (1994).

Patti et al., "Molecular characterization and expression of a gene encoding a *Staphylococcus aureus* collagen adhesin" *J. Biol. Chem.* 267:4766–4772 (1992).

Pohlschröder et al., "Protein translocation in the three domains of life: variations on a theme" *Cell* 91:563–566 (1997).

Poritz et al., "An *E. coli* ribonucleoprotein containing 4.5S RNA resembles mammalian signal recognition particle" *Science* 250:1111–1117 (1990).

Randall, L.L. "Peptide binding by chaperone SecB: implications for recognition of nonnative structure" *Science* 257:241–245 (1992).

Rohrer et al., "The essential *Staphylococcus aureus* gene fmhB is involved in the first step of peptidoglycan pentaglycine interpeptide formation" *Proc. Natl. Acad. Sci. USA* 96:9351–9356 (1999).

Schleifer et al., "Peptidoglycan types of bacterial cell walls and their taxonomic implications" *Bacteriol. Rev.* 36:407–477 (1972).

Sjödahl, J., "Repetitive sequences in protein A from *Staphylococcus aureus*. Arrangement of five regions within the protein, four being highly homologous and Fc–binding." *Eur. J. Biochem.,* 73:343–351 (1977).

Sjöquist et al., "Protein A isolated from *Staphylococcus aureus* after digestion with lysostaphin" *Eur. J. Biochem.* 29:572–578 (1972a).

Sjöquist et al., "Localization of protein A in the bacteria" *Eur. J. Biochem.* 30:190–194 (1972b).

Strominger et al. "Peptidoglycan transpeptidase and D–alanine carboxypeptidase: penicillin–sensitive enzymatic reactions" *Fed. Proc.* 26:9–18 (1967).

Tipper et al. "Mechanism of action of penicillins: a proposal based on their structural similarity to acyl–D–alanyl–alanine" *Proc. Natl. Acad. Sci. USA* 54:1133–1141 (1965).

Ton–That et al. Anchor structure of staphylococcal surface proteins. III. The role of the FemA, FemB, and FemX factors in anchoring surface proteins to the bacterial cell wall. *J. Biol. Chem.* 273:29143–29149 (1998).

Ton–That et al. "Purification and characterization of sortase, the transpeptides that cleaves surface proteins of *Staphylococcus aureus* at the LPXTG motif" *Proc. Natl. Acad. Sci USA*, 96:12424–12429 (1999).

Ton–That et al. "Anchoring of surface proteins to the cell wall of *Staphylococcus aureus*. I. Sortase catalyzed in vitro transpeptidation reaction using LPXTG peptide and NH2–Gly3 substrates" *J. Biol. Chem.* 275:9876–9881 (1999).

Ton–That et al. "Anchor structure of staphylococcal surface proteins. IV. Inhibitors of the cell wall sorting reaction" *J. Biol. Chem.* 274:24316–24320 (1999).

Uhlén et al. "Complete sequence of the staphylococcal gene encoding protein A" *J. Biol. Chem.* 259:1695–1702 and 13628 (1984).

Ulbrandt et al. "The *E. coli* signal recognition particle is required for the insertion of a subset of inner membrane proteins" *Cell* 88:187–196 (1997).

van Heijenoort et al. "Effects of moenomycin on *Escherichia coli*" *J. Gen. Microbiol.* 133:667–674 (1987).

M. Kuroda, et al., "Whole Genome Sequencing of Meticillin–Resistant Staphylococcus Aureus", *The Lancet*–357:1225–1240(2001).

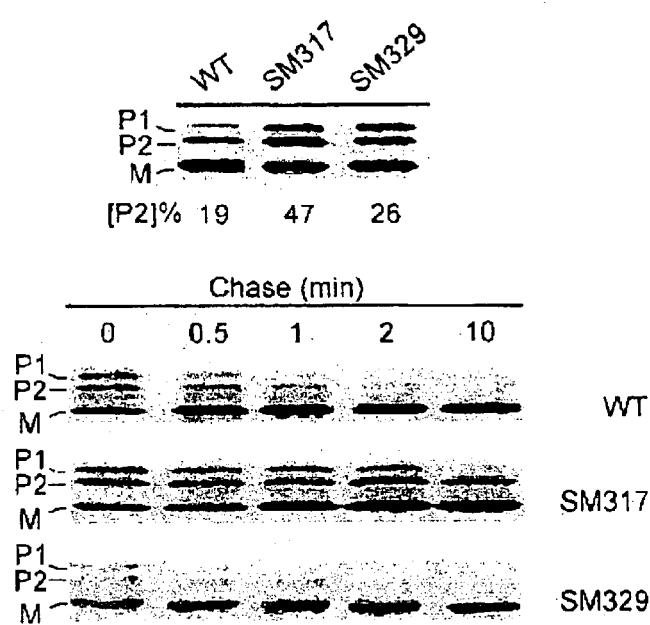
FIG. 2B
FIG. 2C
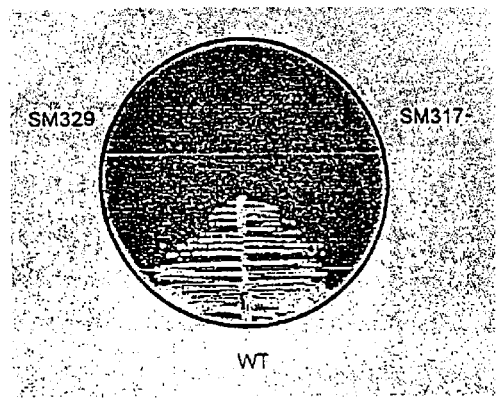
FIG. 2D

FIG. 6A

```
ATG AAA TGG ACA AAT CGA TTA ATG ACA ATC GCT GGT GTG GTA CTT ATC CTA     18
 M   K   W   T   N   R   L   M   T   I   A   G   V   V   L   I   L
GTG GCA GCA TAT GAA TTT GCT AAA CAA CCA TAT ATC GAT AAT AAT GTA CTT CAC  36
 V   A   A   Y   E   F   A   K   Q   P   Y   I   D   N   N   V   L   H
GAT AAA GAT GAA AAG AAG CAG ATT GAA GCT CAA TAT GAT AAA AAT CCG AAA GAA  54
 D   K   D   E   K   K   Q   I   E   A   Q   Y   D   K   N   P   K   E
AAA GAT AAA K CAA CAA ATT CCA CAA ATT CCG AAA AAA GAT CCA TCG TAT CCA GGA 72
 K   D   K   K   Q   Q   I   P   Q   I   P   K   K   D   P   S   Y   P   G
GCA GGC TAT ATT GAA GAT GAT GCT AAA K ATT K GAT GTA GTA TAT GAA GAA GAA 90
 A   G   Y   I   E   D   D   A   K   I   K   D   V   V   Y   E   E   E
CCA GCA ACA CCT GAA CAA CAA TTA CAA AAT AGA GGT GTA GCA GGA TTT GCA GAA AAT CCG 108
 P   A   T   P   E   Q   Q   L   Q   N   R   G   V   A   G   F   A   E   N
TCA CTA GAT GAT TTT CAA CAA AAT ATT TCA AAA CAC ACT TTC ATT GAC CGT CCG  126
 S   L   D   D   F   Q   Q   N   I   S   K   H   T   F   I   D   R   P
AAC TAT CAA TTT CAA GAA ACA CTT CTT GAA AAT GCA AAA AAG AAA AGT ATG ATG TAC TAC TTT 144
 N   Y   Q   F   Q   E   T   L   L   E   N   A   K   K   K   S   M   V   Y   F
AAA GTT GGT GTA TAT AAT AAT ACA CGT AAG AAT ATG ACA GGT G ATA AGA GAT GTT AAG 162
 K   V   G   V   Y   N   N   T   R   K   N   M   T   G   I   R   D   V   K
CCT ACA GAT GAA GGA GTT CTA GAT AAT GAT GAA CAA CAA AAA CAA TTA ACA 180
 P   T   D   E   G   V   L   D   N   D   E   Q   K   Q   L   T
TTA ATT ACT GAT TAT TAC AAA TAA GAA GAA AAA GGC ACA GGC GTT GAA AAA CGT AAA 198
 L   I   T   D   Y   Y   K   N   E   E   K   K   G   T   G   V   E   K   R   K
ATC TTT GTA GCT ACA GAA GTC                                              206
 I   F   V   A   T   E   V  *
```

(seq. ID NO. 2)
(seq. ID NO. 3)

>fasta SrtB (SEQ ID No:38)
MRMKRFLTIVQILLVIIIFGYKIVQTYIEDKQERANYEKLQQKFQMLMSKHQAHVRPQFESLEKINKDIVGWIKLSGT
SLNYPVLQKTNHDYLNLDFEREHRRKGSIFMDFRNELKILNHNTILYGHHVGDNTMFDVLEDYLKQSFYEKHKIIEFDN
KYGKYQLQVFSAYKTTTKDNYIRTDFENDQDYQQFLDETKRKSVINSDVNVTVKDKIMTLSTCEDAYSETTKRIVVVAKI
IKVS >8092 SrtB (from 47233 to 49964) (SEQ ID No:37)
AAAAACCCTTGTGGTGTCACTGTACCTGATAAAGATTCAGCAACTTTCATGTTTATTTCA
AAAACTTCTTGCGCGTATGCGATAATTGCTGATCTAATCTTGCCGGTTCAATTGCAAAT
AATTGTGTAATTACAATTCCACTTTGATAAGCTTCTTCAATTAAATGCACACCTTCAATT
AAAGCTAATCCAGTTTTATCCCCTCTCACGTTTCTCTTTTAGCTTGTTCGCTTGTTTAATT
CTATTATTTTGTGCAGAAGTAATTGTTCCATTGATAGCTCCTCGTTTATTTTAAAAA
TAAAATATTAATTCACTCATAATAAGATGAAAACATTTGATTGTATAGTTAATATTAATTAAT
CGCTTTTATCACTCATAATATTTCAAATTGTATAATTCTTTTATCGATACTACTA
TAAATCATACGCCCCAAAATATCATTATTAAGCACATCAAATCAAACTATGTTTTAGCAATTGT
GATATAATTGATGATTATTTGTGTTCATTAAAAAAACGACCATCATCGTATCATGTCGTTA
TGTTAGCATGTTGTGTTCATTAAAAAAACGACCAAGTACTGCAACCTCTTTAAATTCAATTATT
CAAAAGCTAACAATACCAATTGTCATATAGCCTATATCATATGTAATTACTTTGTTATTTATAATCGGGCTACTTT
TCATGTAACTATAGCCTATATCATATGTAATTACTTTGTTATTATAATCGGGCTACTTT
CATCTTCATTTTACTTCCTAACATGTTTATGCGCTGCTTAAAGACATCAGATTTTAACC
AATCCGTAAAGCTTGCTTTGATTTGTAACAACATGCCATCAAAGCCTTCTAATGTTTCAATCCCAT
CTTGTTTCTCAAAGTTGTGTAACAACATGCCATCAAAGCCTTCTAATGTTTCAATCCCAT
GTCTCGTGTAAATCGTTCTATAATATCCTTCTTTTGCTGTTCCTGTTAACTTACCTAATTATTTTG
TTTCTGCCATAAATTCATAATTTCGTCGTTCACTATGCATCTTCGCACGTTGATAAAGTCA
CGACACAACAATTCTTTTCGTCGTTCACTTAACATCTGAATTAATTACAGATTTACGTTTGTCT
TTATTCTATCTTTTACCGTTACATTAAATCTTGATCATTTTCAAAATCTGTACGTATGTAATTATCTT
CATCTAAAAATTGTGATAATCTTGATAATCTTGATCATTTTCAAAATCTGTACGTATGTAATTATCTT
TAGTAGTAGTTTTATATGCACTAAATACTTGCAATTGATATTTACCATATTTATTGTCAA
ATTCAATTATCTTGTGTTTTCATAAAACGATTGCTTTAAATAATCTTCTAACACATCAA
ACATCGTATTATCACCGACATGGTGCCCGTATAAAAATAGTATTATTGATTAAATTCTTCA

FIG. 6B

| FIG. 6B |
|---|
| FIG. 6B |
| FIG. 6B |

FIG. 6B

```
ATTCATTTCTAAATCCATAAAATACTACCTTTACGTCGATGTTCTCGCTCAAAATCTA
AATTAAATAATCGTGATTTGTCTTACCTGTCGTAGTACTGGATGGTTTAATGATGTTCCTG
ATAATTTATCCAACAATGTCTTTATTTTTTCAAGTGATTCAAATTGTGGTC
TCACATGTTCTTGATGTTTGCTCATCAGCATTGAAATTTTGTTGTAATTCTCATAAT
TTGCGCGTTCTTGCTTGTCTTCAATATATGTTTGAACAATTTGTAACCAAAAATGATAA
TAATTACAACCAATAAAATTTGTACAATAGTTAAAAATCGCTTCATTCTCATAAAAATCC
TCTTTTATTAACGACGTTTCTTCAGTCATCACTAAACCAGTTGTGTTACCGTTTTAGATT
CGATTTCGTTGACTTTGACAAATTAAGTAAATTAGCATTGGACCACGACAATCATTAAA
ATAGCATTGGCTGGAATTTCTAAAGGAGGCTGTATCACTCGTCCTAATAAATCAGCCACT
AACAATAGCCATGCACCAATAACTGTAGAAAACGGAATAAGTACTCTGTAATTGCCCCCA
ACTAGCTTTCTAACCACATGTGGCACACAATAATACCTAAAAAGGCTAGTTGTCCAACAATC
GCAACAGTTGCACTTGCTAAAAATACTGCTAATAAACCTGTTAACCATCTGTAACGATCA
ATATTAAAACCGATACTTCGCGCTTGTATGTCGTCTAAATTAGTAAATTCAATTTAGGG
GACAATAGTAATGTTAATATTAATCCCAATAATGCTGATACTGCTAATATGTATACGTCG
CTCCATATTTCATTGTTAAGCCTTGAGGAATTTTCATTAAAGGGTTTTGAGTTAAAATT
TCTAAAACACCATTAATTAATAATACGAATAATATCCAACACCTACTAATATCATACTTACAGCA
TTGAATCTAAATTTAGAATGCAACAATATAATTGTACAATTGGTATTAAACCTCCAATA
AAACTTAATAATGGTAAGTAAGTAACAATTGTGAATAAACAACATACAAAGTGCTCTC
ATTATAAGTGCACCTGAGGAAACGCCAATGATATTCGCCTCTGCCAACCATCAATGCAATTAAT
GCTGCTTGTAATAATGCTCCAGAAACTGCTAACATTGCGCCAACCATCAATGCAATTAAT
ATACGTGGCAAATCGCAAATCAATGATTGAATCCACTGCTTCATTGCTACCAGTTGTAAAT
TTTGTAAATAGGTCATTAAATGACAATTAATTGTACCGGTTACAAACGAAATATAAGCA
GTTGCGATTAAAATGACTAACAAACATAAAAA

8092 SrtB (from 47233 to 49964)
```

FIG. 6B₂

```
                          15                        30                         45                          60                         75                    90
1 Anei    -------------------------------------------------------MGLLTYPTAASWVSQYNQSKVTADYSAQVDG---ARPDAKTQVEQAHAYND-ALSAGAVLEANNHVPTG    65
2 Spyo    ---------------------------------------------------------------------------------------MEEVWQKAKAYNA-RLGIQPVPDAFS-PRDG           29
3 Efea    MKSKKKRRIIDGFMILLLIGIGAFAYPFVSDALNNYLDQQIIAHYQAKASQE--NTKEMAELQEKMEKKNQ-ELAKKGSNPGLDPFSET                                           87
4 Bsub    ------------------------------MKKVIPLFIIAAGLVIAGYG--GFKLIDTNTKTEQTLKE-AKLAAKKPQEASGRKNS                                           54
5 Smut    ------------------------MKKERQSRKKRSFLRTFLPILLLVIGLALIFNTPIRNALIAWNTNRYQVSNVSKKDIEHNKAAHSSFDFK                                    70
6 Saur    ------------------------------MKKWTNRLMTIAGVVLILV----AAYLFAKPHIDNYLHD-KDKDEKIEQYDKNVKEQ                                            52

1 Anei    AGSSKDSSLQYANITKANNEGLMARLKTFSTSEDIRVAHG-TADDTLKKLGHIEGTSFRVGGEGTRSVLTGJRGLAE---ATMTNLDK         151
2 Spyo    IHD-KN------YESLQIENNDEMGYVEYSIKVLIFHY-TTDEVTRKLAGHIFGSALPVGGDTHTVISARGLPS---AEMTNLNL            110
3 Efea    QKTTKKP---DKSYFESHT--IGVLTFDKINVRLIPDK-TNALIEKSSLLEGISYRTGINTHAVISGRGLPQ---AKLFIDLPE             167
4 Bsub    TDQAKN----KASFKPETG-QASCHEIFKTNAELKVEG-TDADDEKVGHYKDSYVED-ENGQIVLSGR-----DTVRRIGE                129
5 Smut    KVESUSTQSVLAAQMAAQKLPVLGGIATFDIKNLIFKG-LDNVGTYLAGTMKNDQVMG-ENNYALASHLVGMTGSSQMFSPLER             157
6 Saur    ASKDKKQQ--AKPQIPKDSKVAGYIEIDADEKHVYPGPATPEQNRKVSFAEFNESED--DQNISLAGTLFIDRP--NYQTNLKA             135

1 Anei    VKTIDSLIVEVFGEVITRVTSKVFEPEFTEAIPVEEGKDIFLTLVITP----GINTIERILTGERIYETPAFDLAAAGERPDVPHFP          237
2 Spyo    VKKLDTVERVLNKVFAIKVDQFTTEPDQVTSISGVMGKDYATMVITPY----GVNTKRLIVRGHRTAYHYKKYQAKKAMKLVDKSR          196
3 Efea    LRKSDEVTEVNGKRLAQVDQITTPPTTKDIHIESCQDIIVTHLVITPQ----MINSHRLLVRGHRLPYQPEKAAGMKRVAQQQNLL          253
4 Bsub    EEKSDOLRLISYGEFEVKTKIDKDRTSTILQHEKEFLITLVPHSYVGNAPKRVITYSKRVL----VPFSYVGNAPKRVITYSKRVL           198
5 Smut    AKELMELTLDKNKVFTVISEVKTLTPEHVLDNRPGONEVTLVLPA----GITARTLVHSTYKGENDENKTSKKIKKAFRQSYN              242
6 Saur    AKKLSMVFKVGNEIRKAKMTSIRDLKFTDVGLDEQKQKDQLILLDDY--NEKTGVAWFKRKIEVATEVK--                          206

1 Anei    WWAVGLAAGLIVVGLYLWRSGYAAARAKERALARARAAQEEPQPQTWAEQMRIWMDDDAGVEPQRWFTDLPVPPQSEMENLALLEEIAS        327
2 Spyo    MWAEVVCAAFGVVIAIILVEMYSRVSAKKSK-----                                                            227
3 Efea    LWTLLLIACALIISGFIIWYKRRKKTTRKPK-----                                                            284
4 Bsub    ------                                                                                         198
5 Smut    QISF--                                                                                         246
6 Saur    ------                                                                                         206

1 Anei    LSAPSGRWDDQELIDTAEIPVLDATRPSAGTSGRTHRL    367    (seq. ID NO. 5)
2 Spyo    --------------------------------------    227    (seq. ID NO. 4)
3 Efea    --------------------------------------    284    (seq. ID NO. 6)
4 Bsub    --------------------------------------    198    (seq. ID NO. 8)
5 Smut    --------------------------------------    246    (seq. ID NO. 7)
6 Saur    --------------------------------------    206    (seq. ID NO. 3)
```

FIG. 7A

```
Blast 2 Sequences results

BLAST 2 SEQUENCES RESULTS VERSION VLASTP 2.1.2 [Nov-13-2000]
Matrix gap open:    gap extension:
x_dropoff:   expect:    wordsize:   Filter Sequence 1 lcl | 1_fasta SrtA Length 206    (1  . . . 206)
Sequence 2 lcl | 2_fasta SrtB Length 244    (1  . . . 244)

2 1
NOTE: The statistics (bitscore and expect value) is calculated based on the size of nr
database Score = 38.9 bits (89), Expect = 0.041
Identities = 55/244 (22%), Positives = 92/244 (37%), Gaps = 50/244 (20%)

Query:   7 RLMTIAGVVLLVAAYLFAKPHIDNYLHDKDKDEKIEQYDKNVKEQASKDKKQQAKPQ--  64
           R +TI    ++L+ +   +F +   + Y+   DK  + E+ + +  SK +      +PQ
Sbjct:   5 RFLTIVQILLVIII-IFGYKIVQTYIEDKQERANYEKLQQKFQMLSKHQAH-VRPQFE  62

Query:  65 -IPKDKSKVAGYIEIPDADIKEPVYPGPATPEQLN---------RGVSFAEENESLD--D  112
            + K   + + G+I++  +   + PV G    + LN         +G F +  L    +
Sbjct:  63 SLEKINKDIVGWIKLSGTSLNYPVLQGKTNHDYLNLDFEREHRRKGSIFMDFRNELKILN  122

Query: 113 QNISIAGHTFIDRPNYQFTN--LKAAKKGSMVYFKVGNETRKYKMTSIRDVKPTDVG---  167
            N  +GH  D +      +   LK +     + + + N+ KY++     K T
Sbjct: 123 HNTILYGHHVGDNTMFDVLEDYLKQSFYEKHKIIEFDNKYGKYQLQVFSAYKTTKDNYI  182

Query: 168 ---------VLDEQKGK-----------DKQLTLITCDD-YNEKTGVWEKRKIFVA  202
                     + LDE K K           DK +TL TC+D Y+E T    KR + VA
Sbjct: 183 RTDFENDQDYQQFLDETKRKSVINSDVNVTVKDKIMTLSTCEDAYSETT---KRIVVVA  238

Query: 203 TEVK  206
            +K
Sbjct: 239 KIIK  242

CPU time:   0.07 user secs.   0.01 sys. secs   0.08 total secs.

Gapped
Lambda K    H
       0.313  0.133  0.376
```

FIG. 7B

IDENTIFICATION OF SORTASE GENE

CROSS-REFERENCE To RELATED APPLICATIONS

This application is a continuation-in-part of pending U.S. patent application Ser. No. 09/292,437, filed Apr. 15, 1999 which is hereby incorporated by reference in its entirety.

GOVERNMENT RIGHTS

This invention was made with Government support under Grant No. AI39987, awarded by the National Institutes of Health. The government has certain rights in this invention.

BACKGROUND OF THE INVENTION

General Background and State of the Art: This invention is directed to an enzyme from Gram-positive bacteria, designated sortase-transamidase, nucleic acid segments encoding the enzyme, and methods of use of the enzyme.

Human infections caused by Gram-positive bacteria present a medical challenge due to the dramatic increase in multiple antibiotic resistance strains in recent years. Gram-positive bacteria that can cause serious or fatal infections in humans include Staphylococcus, Streptococcus, Enterococcus, Pneumococcus, Bacillus, Actinomyces, Mycobacterium, and Listeria, as well as others. Infections caused by these pathogens are particularly severe and difficult to treat in immunologically compromised patients. These include patients suffering from infection with the Human Immunodeficiency Virus (HIV), the virus that causes AIDS, as well as patients given immune-suppressive agents for treatment of cancer or autoimmune diseases. In particular, infections caused by various Mycobacterium species, including *M. tuberculosis, M. bovis, M. avium*, and *M. intracellulare*, are frequently the cause of disease in patients with AIDS.

Therefore, it is apparent that new target sites for bacterial chemotherapy are needed if such pathogenic organisms are to be controlled.

A unique characteristic of these pathogens and many Gram-positive bacteria is their surface display of proteins anchored to the cell wall. In fact, many of these molecules are known to be involved in essential cellular functions, including pathogenesis in a susceptible host. Thus, a possible disruption in this anchoring process may prove to be an effective treatment against these disease-causing elements.

The anchoring of surface molecules to the cell wall in Gram-positive bacteria has been demonstrated to involve a conserved pathway, culminating in recognition of a conserved cleavage/anchoring site by some previously uncharacterized cellular machinery. Molecules whose ultimate location is the cell wall must invariably be translocated across the single cellular membrane of these organisms. This is mediated for all cell wall anchored proteins by the well studied secretory pathway, involving cleavage of an amino-terminal signal peptide by a type I signal peptidase. Upon translocation of the molecule out of the cytoplasm, a mechanism must be present that extracellularly recognizes this protein as a substrate for anchoring. This process has been previously shown to involve the carboxyl-terminally located cell wall sorting signal, consisting of a highly conserved motif such as LPXTG (SEQ ID NO:1), in which X can represent any of the twenty naturally occurring L-amino acids, followed by a series of hydrophobic residues and ultimately a sequence of positively-charged residues. Thus, once amino-terminally modified and successfully secreted, a polypeptide with this carboxyl-terminal sequence can present itself as a substrate to be processed by the anchoring machinery. At this time, cleavage of the sorting signal after the threonine residue is coupled with covalent linkage of the remainder of the polypeptide to the free amino group of the pentaglycine crossbridge in the cell wall.

It is this transpeptidation reaction that anchors mature surface proteins to the peptidoglycan layer, from which point the molecules can serve their biological functions. Therefore, there is a need to isolate and purify the enzymes that catalyze this reaction. There is also a need to identify the genes encoding such enzymes in order that the enzymes can be produced by genetic engineering techniques.

Additionally, there is also a need to develop new methods for displaying proteins or peptides on the surfaces of bacteria. For many purposes, it is desirable to display proteins or peptides on the surfaces of bacteria so that the proteins or peptides are accessible to the surrounding solution, and can, for example, be bound by a ligand that is bound specifically by the protein or peptide. In particular, the display of proteins on the surface of bacteria is desirable for the preparation of vaccines, the linkage of molecules such as antibiotic molecules or diagnostic reagents to cells, for screening reagents such as monoclonal antibodies, and for the selection of cloned proteins by displaying the cloned proteins, then observing their reaction with specific reagents such as antibodies. One way of doing this has been with phage display (G. P. Smith, "Filamentous Fusion Phage: Novel Expression Vectors that Display Cloned Antigens on the Virion Surface," *Science* 228:1315–1316 (1985)). However, phage display is limited in its practicality, because it requires that the protein being displayed to be inserted into a coat protein of filamentous phage and retain its activity while not distorting the conformation of the coat protein, allowing functional virions to be formed. In general, this technique is therefore limited only to small peptide and proteins.

Therefore, there is a need for a more general method of peptide and protein display.

INVENTION SUMMARY

The present invention is directed to sortase-transamidase enzymes from Gram-positive bacteria, particularly the products of the surface protein sorting genes (srtA and srtB) of *Staphylococcus aureus*, and methods for their use, particularly in the areas of drug screening and peptide and protein display and as targets for bacteriocidal compounds or antibiotics.

One aspect of the present invention is a substantially purified sortase-transamidase enzyme from a Gram-positive bacterium, the enzyme catalyzing a reaction that covalently cross-links the carboxyl terminus of a protein having a sorting signal to the peptidoglycan of a Gram-positive bacterium, the sorting signal having a motif of $LPX_3X_4G$ therein, wherein sorting occurs by cleavage between the fourth and fifth residues of the $LPX_3X_4G$ motif. Typically, the Gram-positive bacterium is a species selected from the group consisting of but not limited to *Staphylococcus aureus, S. sobrinus, Enterococcus faecalis, Streptococcus pyogenes*, and *Listeria monocytogenes*. Preferably, the Gram-positive bacterium is *S. aureus*, and more preferably, the enzyme is the product of the srtA gene or the srtB gene of *S. aureus*.

Preferably, the enzyme has a molecular weight of about 23,539 or about 29,076 daltons and the sorting signal further includes: (2) a substantially hydrophobic domain of at least 31 amino acids carboxyl to the motif; and (3) a charged tail region with at least two positively charged residues carboxyl to the substantially hydrophobic domain, at least one of the two positively charged residues being arginine, the two positively charged residues being located at residues 31–33 from the motif, wherein $X_3$ is any of the twenty naturally-occurring L-amino acids and $X_4$ is selected from the group consisting of alanine, serine, and threonine.

The enzyme includes an amino acid sequence of: (1)

M-K-K-W-T-N-R-L-M-T-I-

A-G-V-V-L-I-L-V-A-A-Y-L-F-A-K-P-H-I-D-N-Y-L-H-D-K-D-K-D-E-K-I-E-Q-Y-D-K-N-V-K-

E-Q-A-S-K-D-K-K-Q-Q-A-K-P-Q-I-P-K-D-K-S-K-V-A-G-Y-I-E-I-P-D-A-D-I-K-E-P-V-Y-P-

G-P-A-T-P-E-Q-L-N-R-G-V-S-F-A-E-E-N-E-S-L-D-D-Q-N-I-S-I-A-G-H-T-F-I-D-R-P-N-Y-

Q-F-T-N-L-K-A-A-K-K-G-S-M-V-Y-F-K-V-G-N-E-T-R-K-Y-K-M-T-S-I-R-D-V-K-P-T-D-V-

G-V-L-D-E-Q-K-G-K-D-K-Q-L-T-L-I-T-C-D-D-Y-N-E-K-T-G-V-W-E-K-R-K-I-F-V-A-T-E-V-

K (SEQ ID NO:3)

and (2) sequences incorporating one or more conservative amino acid substitutions in SEQ ID NO:3, wherein the conservative amino acid substitutions are any of the following: (1) any of isoleucine, leucine, and valine for any other of these amino acids; (2) aspartic acid for glutamic acid and vice versa; (3) glutamine for asparagine and vice versa; and (4) serine for threonine and vice versa.

Alternatively, the enzyme can include an amino acid sequence of: (1)

M-R-M-K-

R-F-L-T-I-V-Q-I-L-L-V-V-I-I-I-F-G-Y-K-I-V-Q-T-Y-I-E-D-K-Q-E-R-A-N-Y-E-K-L-Q-Q-K-

F-Q-M-L-M-S-K-H-Q-A-H-V-R-P-Q-F-E-S-L-E-K-I-N-K-D-I-V-G-W-I-K-L-S-G-T-S-L-N-Y-

P-V-L-Q-G-K-T-N-H-D-Y-L-N-L-D-F-E-R-E-H-R-R-K-G-S-I-F-M-D-F-R-N-E-L-K-I-L-N-H-

N-T-I-L-Y-G-H-H-V-G-D--N-T-M-F-D-V-L-E-D-Y-L-K-Q-S-F--Y-E-K-H-K-I-I-E-F-D-N-K-Y-

G-K-Y-Q-L-Q-V-F-S-A-Y-K-T-T-T-K-D-N-Y-I-R-T-D-F-E-N-D-Q-D-Y-Q-Q-F-L-D-E-T-K-

R-K-S-V-I-N-S-D-V-N-V-T-V-K-D-K-I-M-T-L-S-T-C-E-D-A-Y-S-E-T-T-K-R-I-V-V-A-K-I-

I-K-V-S (SEQ ID NO:38)

and (2) sequences incorporating one or more conservative amino acid substitutions in SEQ ID NO:38, wherein the conservative amino acid substitutions are any of the following: (1) any of isoleucine, leucine, and valine for any other of these amino acids; (2) aspartic acid for glutamic acid and vice versa, (3) glutamine for asparagine and vice versa; and (4) serine for threonine and vice versa.

Another aspect of the present invention is a nucleic acid sequence encoding this enzyme. In one alternative, the nucleic acid sequence includes therein a sequence of:

ATGAAAAAATGGACAAATCGATTAATGACAATCGCTGGTGTGGTACTTAT

CCTAGTGGCAGCATATTTGTTTGCTAAACCACATATCGATAATTATCTTC

ACGATAAAGATAAAGATGAAAAGATTGAACAATATGATAAAAATGTAAAA

GAACAGGCGAGTAAAGATAAAAAGCAGCAAGCTAAACCTCAAATTCCGAA

AGATAAATCGAAAGTGGCAGGCTATATTGAAATTCCAGATGCTGATATTA

AAGAACCAGTATATCCAGGACCAGCAACACCTGAACAATTAAATAGAGGT

GTAAGCTTTGCAGAAGAAAATGAATCACTAGATGATCAAAATATTTCAAT

TGCAGGACACACTTTCATTGACCGTCCGAACTATCAATTTACAAATCTTA

AAGCAGCCAAAAAAGGTAGTATGGTGTACTTTAAAGTTGGTAATGAAACA

CGTAAGTATAAAATGACAAGTATAAGAGATGTTAAGCCTACAGATGTAGG

AGTTCTAGATGAACAAAAAGGTAAAGATAAACAATTAACATTAATTACTT

GTGATGATTACAATGAAAAGACAGGCGTTTGGGAAAAACGTAAAATCTTT

GTAGCTACAGAAGTCAAATAA (SEQ ID NO: 2);

and (2) a sequence complementary to SEQ ID NO:2 (SEQ ID NO:39). In another alternative, the nucleic acid sequence can include a sequence hybridizing with SEQ ID NO:2 or a sequence complementary to SEQ ID NO:2 with no greater than about a 15% mismatch under stringent conditions. Preferably, the degree of mismatch is less than about 5%; more preferably, the degree of mismatch is less than about 2%.

In yet another aspect of the present invention a nucleic acid sequence encoding this enzyme includes therein a sequence of:

```
AAAAACCCTTGTGGTGTCACTGTACCTGATAAAGATTCAGCAACTTTCAT

GTTTATTTCAAAAACTTCTTGCGCGTATGCGATAATTTGCTGATCTAATC

TTGCCGGTTCAATTGCAAATAATTGTGTAATTACAATTCCACTTTGATAA

GCTTCTTCAATTAAATGCACACCTTCAATTAAAGCTAATCCAGTTTTATC

CCTCTCACGTTTCTTTTTTAGCTTGTTCGCTTGTTTAATTCTATTATTTT

GTGCAGAAGTAATTTGTTCCATTGATAGCTCCTCGCTTTATTTTTAAAAA

TAAAAATATTAATCATTAATAAGATGAAAACATTTGATTGTATAGTTAAT

ATTAATTAATCGCTTTTATCACTCATAATATTTCAAATTGTATAAATTTC

TTTTATCGATACTACTACTATAAATCATACGCCCCAAAATATCATTATTA

ATTCTTTTCTTCTTCAAAATAAATCAAAATGATATAATTGATGATTATTT

TCAAAGCACATTCAAATCAAACTATGTTTTAGCAATTTGTTGTTAGCATG

TTTGTGTTCATTAAAAAAACGACCATCATCGGTATCATGTATGGTCGTTA

CAAAAGCTAACAATACCAATTGTCATAACAAGTACTGCAACCTCTTTAAA

TTCAATTATTTCATGTAACTATAGCCTATATCATATGTAATTACTTTGTT

ATTTATAATCGGGCTACTTTCATCTTCATTTTTACTTCTAACATGTTTAT

GCGCTGCTTTAAAGACATCAGATTTTAACCAATCCGTAAAAGCTTGCTTT

GATTTCCAAACTGTTAAAATTTTCACTTCATCAAAATCTTCTTGTTCTAA

AGTTTGTGTAACAAACATGCCATCAAAGCCTTCTAATGTTTCAATCCCAT

GTCTCGTGTAAAATCGTTCTATAATATCTTTTGCTGTTCCTTTTGTTAAC

GTCAGCCTATTTTCTGCCATAAATTTCATAATTATCCTCTTTTCTGTTTA

ACTTACCTTAATTATTTTTGCGACAACAACAATTCTTTTCGTCGTTTCAC

TATATGCATCTTCGCACGTTGATAAAGTCATTATTCTATCTTTTACCGTT

ACATTAACATCTGAATTAATTACAGATTTACGTTTTGTCTCATCTAAAAA

TTGTTGATAATCTTGATCATTTTCAAAATCTGTACGTATGTAATTATCTT

TAGTAGTAGTTTTATATGCACTAAATACTTGCAATTGATATTTACCATAT

TTATTGTCAAATTCAATTATCTTGTGTTTTTCATAAAACGATTGCTTTAA

ATAATCTTCTAACACATCAAACATCGTATTATCACCGACATGGTGCCCGT

ATAAAATAGTATTATGATTTAAATTCTTCAATTCATTTCTAAAATCCATA

AAAATACTACCTTTACGTCGATGTTCTCGCTCAAAATCTAAATTTAAATA

ATCGTGATTTGTCTTACCTTGTAGTACTGGATAATTTAATGATGTTCCTG

ATAATTTTATCCATCCAACAATGTCTTTATTTATTTTTTCAAGTGATTCA

AATTGTGGTCTCACATGTTCTTGATGTTTGCTCATCAGCATTTGAAATTT

TTGTTGTAATTTCTCATAATTTGCGCGTTCTTGCTTGTCTTCAATATATG

TTTGAACAATTTTGTAACCAAAAATGATAATAATTACAACCAATAAAATT

TGTACAATAGTTAAAAATCGCTTCATTCTCATAAAAATCCTCTTTTATTA

ACGACGTTTCTTCAGTCATCACTAAACCAGTTGTTGTACCGTTTTAGATT

CGATTTCGTTGACTTTGACAAATTAAGTAAATTAGCATTGGACCACCGAC

AATCATTAAAATAGCATTGGCTGGAATTTCTAAAGGAGGCTGTATCACTC

GTCCTAATAAATCAGCCACTAACAATAGCCATGCACCAATAACTGTAGAA

AACGGAATAAGTACTCTGTAATTGCCCCCAACTAGCTTTCTAACCACATG
```

-continued

```
TGGCACAATAATACCTAAAAAGGCTAGTTGTCCAACAATCGCAACAGTTG

CACTTGCTAAAAATACTGCTAATAAACCTGTTAACCATCTGTAACGATCA

ATATTAAAACCGATACTTCGCGCTTGTATGTCGTCTAAATTTAGTAAATT

CAATTTAGGGGACAATAGTAATGTTAATATTAATCCCAATAATGCTGATA

CTGCTAATATGTATACGTCGCTCCATATTTTCATTGTTAAGCCTTGAGGA

ATTTTCATTAAAGGGTTTTGAGTTAAAATTTCTAAAACACCATTTAATAA

TACGAATAACGCAACACCTACTAATATCATACTTACAGCATTGAATCTAA

ATTTAGAATGCAACAATATAATTATTAAAAATGGTATTAAACCTCCAATA

AAACTTAATAATGGTAAGTAAAAGTACAATTGTGGAATAAACAACATACA

AAGTGCTCTCATTATAAGTGCACCTGAGGAAACGCCAATGATATTCGCCT

CTGCCAAAGGATTTTGTAGTGCTGCTTGTAATAATGCTCCAGAAACTGCT

AACATTGCGCCAACCATCAATGCAATTAATATACGTGGCAATCGCAAATC

AATGATTGAATCCACTGCTTCATTGCTACCAGTTGTAAATTTTGTAAATA

GGTCATTAAATGACAATTTAATTGTACCGGTTACAAACGAAATATAAGCA

GTTGCGATTAAAATGACTAACAAACATAAAAA
```

(SEQ ID NO: 37);

and (2) a sequence complementary to SEQ ID NO:37 (SEQ ID NO:40). In another alternative, the nucleic acid sequence can include a sequence hybridizing with SEQ ID NO:37 or a sequence complementary to SEQ ID NO:37 with no greater than about a 15% mismatch under stringent conditions. Preferably, the degree of mismatch is less than about 5%; more preferably, the degree of mismatch is less than about 2%.

Yet another aspect of the present invention is a vector comprising a nucleic acid sequence of the present invention operatively linked to at least one control sequence that controls the expression or regulation of the nucleic acid sequence.

Yet another aspect of the present invention is a host cell transfected with a vector of the present invention.

Another aspect of the present invention is a method for producing a substantially purified sortase-transamidase enzyme. The method comprises the steps of:

(1) culturing a host cell according to the present invention under conditions in which the host cell expresses the encoded sortase-transamidase enzyme; and (2) purifying the expressed enzyme to produce substantially purified sortase-transamidase enzyme.

Another aspect of the present invention is a method for screening a compound for anti-sortase-transamidase activity. This method is important in providing a way to screen for antibiotics that disrupt the sorting reaction and are likely to be effective in treating infections caused by Gram-positive bacteria.

In one alternative, the screening method comprises the steps of:

(1) providing a substantially purified sortase-transamidase enzyme according to the present invention;

(2) performing an assay for sortase-transamidase in the presence and in the absence of the compound; and (3) comparing the activity of the sortase-transamidase enzyme in the presence and in the absence of the compound to screen the compound for sortase-transamidase activity.

In another alternative, the screening method comprises the steps of:
(1) providing an active fraction of sortase-transamidase enzyme from a Gram-positive bacterium;
(2) performing an assay for sortase-transamidase in the presence and in the absence of the compound; and
(3) comparing the activity of the sortase-transamidase enzyme in the presence and in the absence of the compound to screen the compound for sortase-transamidase activity.

The active fraction of sortase-transamidase activity can be a particulate fraction from *Staphylococcus aureus*.

The assay for sortase-transamidase enzyme can be performed by monitoring the capture of a soluble peptide that is a substrate for the enzyme by its interaction with an affinity resin. In one alternative, the soluble peptide includes a sequence of at least six histidine residues and the affinity resin contains nickel. In another alternative, the soluble peptide includes the active site of glutathione S-transferase and the affinity resin contains glutathione. In yet another alternative, the soluble peptide includes the active site of streptavidin and the affinity resin contains biotin. In still another alternative, the soluble peptide includes the active site of maltose binding protein and the affinity resin contains amylose.

Still another aspect of the present invention is an antibody specifically binding a sortase-transamidase enzyme of the present invention.

Yet another aspect of the present invention is a protein molecule comprising a substantially purified sortase-transamidase enzyme according to the present invention extended at its carboxyl-terminus with a sufficient number of histidine residues to allow specific binding of the protein molecule to a nickel-sepharose column through the histidine residues added at the carboxyl-terminus.

Still another aspect of the present invention is a method for displaying a polypeptide on the surface of a Gram-positive bacterium comprising the steps of:
(1) expressing a polypeptide having a sorting signal at its carboxy-terminal end, the sorting signal having: (a) a motif of $LPX_3X_4G$ therein; (b) a substantially hydrophobic domain of at least 31 amino acids carboxyl to the motif; and (c) a charged tail region with at least two positively charged residues carboxyl to the substantially hydrophobic domain, at least one of the two positively charged residues being arginine, the two positively charged residues being located at residues 31–33 from the motif, wherein $X_3$ is any of the twenty naturally-occurring L-amino acids and $X_4$ is selected from the group consisting of alanine, serine, and threonine;
(2) forming a reaction mixture including: (i) the expressed polypeptide; (ii) a substantially purified sortase-transamidase according to the present invention; and (iii) a Gram-positive bacterium having a peptidoglycan to which the sortase-transamidase can link the polypeptide; and
(3) allowing the sortase-transamidase to catalyze a reaction that cleaves the polypeptide within the $LPX_3X_4$ motif of the sorting signal and covalently cross-links the amino-terminal portion of the cleaved polypeptide to the peptidoglycan to display the polypeptide on the surface of the Gram-positive bacterium.

Another display method according to the present invention comprises:
(1) cloning a nucleic acid segment encoding a chimeric protein into a Gram-positive bacterium to generate a cloned chimeric protein including therein a carboxyl-terminal sorting signal as described above;
(2) growing the bacterium into which the nucleiracid segment has been cloned to express the cloned chimeric protein to generate a chimeric protein including therein a carboxyl-terminal sorting signal; and
(3) binding the polypeptide covalently to the cell wall by the enzymatic action of a sortase-transamidase expressed by the Gram-positive bacterium involving cleavage of the chimeric protein within the $LPX_3X_4G$ motif so that the polypeptide is displayed on the surface of the Gram-positive bacterium in such a way that the polypeptide is accessible to a ligand.

Another aspect of the present invention is a polypeptide displayed on the surface of a Gram-positive bacterium by covalent linkage of an amino-acid sequence of $LPX_3X_4$ derived from cleavage of an $LPX_3X_4G$ motif, wherein $X_3$ is any of the twenty naturally-occurring L-amino acids and $X_4$ is selected from the group consisting of alanine, serine, and threonine, the polypeptide being displayed on the surface of the Gram-positive bacterium in such a way that the polypeptide is accessible to a ligand.

Another aspect of the present invention is a covalent complex comprising:
(1) the displayed polypeptide; and
(2) an antigen or hapten covalently cross-linked to the polypeptide.

Yet another aspect of the present invention is a method for vaccination of an animal comprising the step of immunizing the animal with the displayed polypeptide to generate an immune response against the displayed polypeptide, or, alternatively, with the covalent complex to generate an immune response against the antigen or the hapten.

Still another aspect of the present invention is a method for screening for expression of a cloned polypeptide comprising the steps of:
(1) expressing a cloned polypeptide as a chimeric protein having a sorting signal at its carboxy-terminal end as described above;
(2) forming a reaction mixture including: (i) the expressed chimeric protein; (ii) a substantially purified sortase-transamidase enzyme according to the present invention; and (iii) a Gram-positive bacterium having a peptidoglycan to which the sortase-transamidase can link the polypeptide through the sorting signal;
(3) binding the chimeric protein covalently to the cell wall by the enzymatic action of a sortase-transamidase expressed by the Gram-positive bacterium involving cleavage of the chimeric protein within the $LPX_3X_4G$ motif so that the polypeptide is displayed on the surface of the Gram-positive bacterium in such a way that the polypeptide is accessible to a ligand; and
(4) reacting the displayed polypeptide with a labeled specific binding partner to screen the chimeric protein for reactivity with the labeled specific binding partner.

Still another aspect of the present invention is a method for the diagnosis or treatment of a bacterial infection caused by a Gram-positive bacterium comprising the steps of:
(1) conjugating an antibiotic or a detection reagent to a protein including therein a carboxyl-terminal sorting signal as described above to produce a conjugate; and
(2) introducing the conjugate to an organism infected with a Gram-positive bacterium in order to cause the conjugate to be sorted and covalently cross-linked to the cell walls of the bacterium in order to treat or diagnose the infection.

If an antibiotic is used, typically it is a penicillin, ampicillin, vancomycin, gentamicin, streptomycin, a cephalosporin, amikacin, kanamycin, neomycin, paromomycin, tobramycin, ciprofloxacin, clindamycin, rifampin, chloramphenicol, norfloxacin, or a derivative of these antibiotics.

Similarly, another aspect of the present invention is a conjugate comprising an antibiotic or a detection reagent covalently conjugated to a protein including therein a carboxyl-terminal sorting signal as described above to produce a conjugate. In still another aspect of the present invention, a composition comprises the conjugate with a pharmaceutically acceptable carrier.

Another aspect of the present invention is a substantially purified protein having at least about 50% match with best alignment with the amino acid sequences of at least one of the putative homologous proteins of *Streptococcus pyogenes* (SEQ.ID NO.4), *Actinomyces naeslundii* (SEQ.ID NO.5), *Enterococcus faecalis* (SEQ.ID NO.6), *Streptococcus mutans* (SEQ.ID.NO.7) or *Bacillus subtilis* (SEQ.ID NO.8) and having sortase-transamidase activity. Preferably, the match is at least about 60% in best alignment; more preferably, the match is at least about 70% in best alignment.

BRIEF DESCRIPTION OF THE DRAWINGS

These and other features, aspects, and advantages of the present invention will become better understood with reference to the following description and accompanying drawings where:

FIG. 6A depicts the DNA sequence of the srtA gene (SEQ ID NO:2) and deduced primary structure of the SrtA protein (SEQ ID NO:3). The NH$_2$-terminal hydrophobic membrane anchor sequence is boxed. A single cysteine predicted to be the active site for cleavage of cell wall sorting signals at the LPXTG motif is shaded.

FIG. 6B depicts the DNA sequence of the srtB gene (SEQ ID NO:37) and deduced amino acid sequence of the SrtB protein (SEQ ID NO:38) in *Staphylococcus aureus*.

FIG. 7A depicts a sequence alignment comparing the predicted primary structure of the SrtA protein (Sortase) with that of homologous sequences identified by database searches. Note the conservation of a single cysteine residue as well as its surrounding sequence.

FIG. 7B depicts an amino acid sequence alignment comparing the amino acid sequence of SrtA with that of SrtB.

OS2 cultures caused increasing amounts of surface protein to be released.

FIG. 13:
(A) depicts a Coomassie-stained SDS-PAGE gel used to characterize surface proteins released by hydroylamine treatment.
(B) depicts an rpHPLC chromatogram of COOH-terminal anchor peptides released from S. aureus BB270 cells via treatment with 0.1 M NH$_2$OH.
(C) depicts an rpHPLC chromatogram of COOH-terminal anchor peptides released from S. aureus BB270 cells via treatment with 0.1 M NH$_2$OH.

Figure 14A:
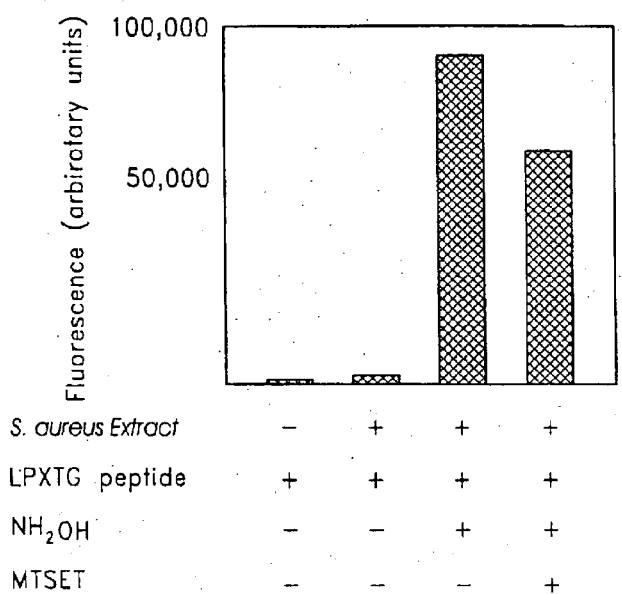
Figure 14C:
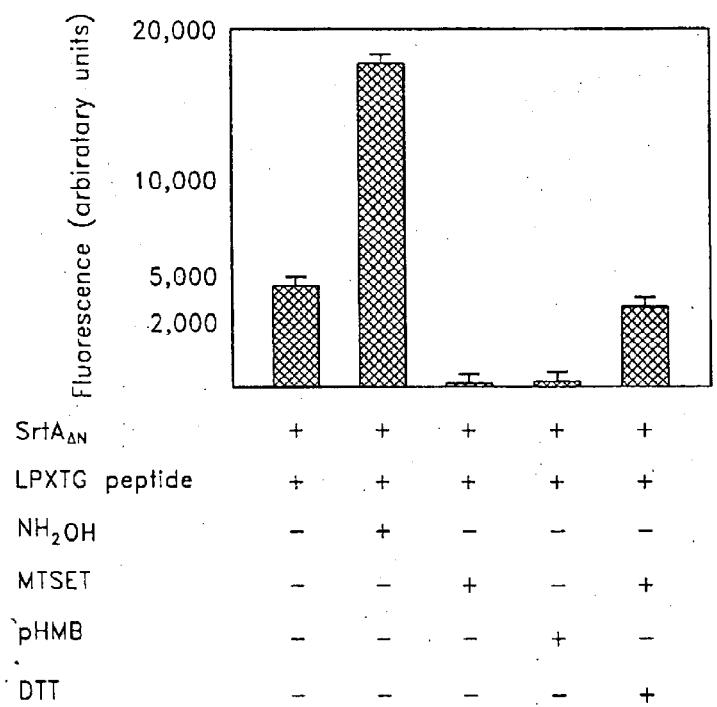
Figure 14B:
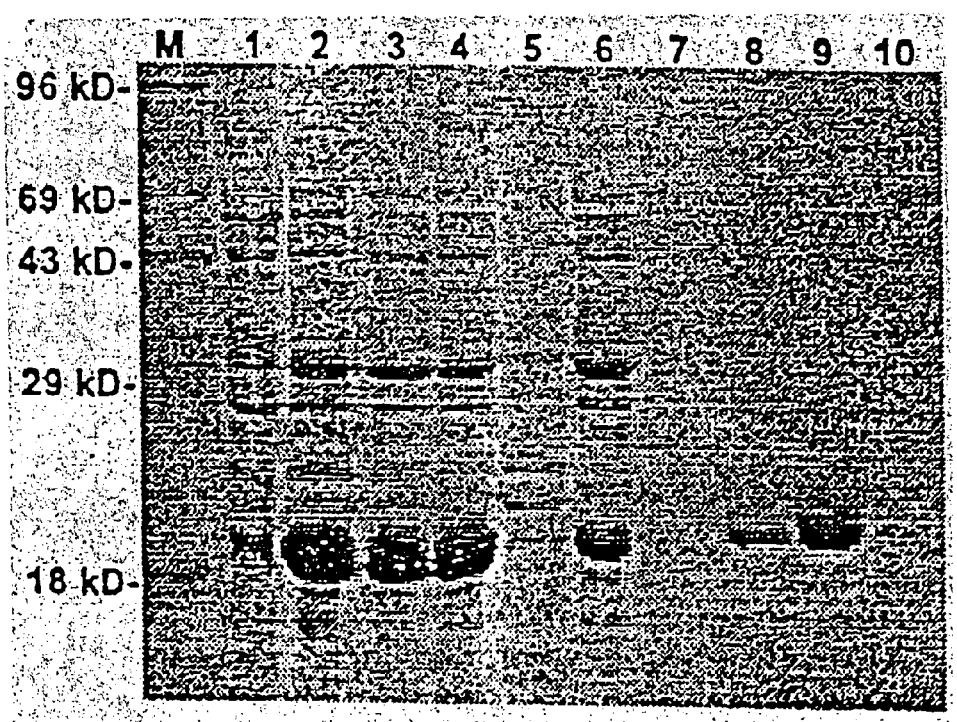

FIG. 14:
(A) is a bar graph depicting the effect of incubating staphylococal extracts with the sorting substrate DABCYL-QALPETGEENPF-EDANS; peptide cleavage is indicated as an increase in fluorescence. The addition of 0.2 M NH$_2$OH increased peptide cleavage, whereas peptide cleavage was inhibited by the addition of methanethiosulfonate (MTSET), a known inhibitor of sortase.
(B) depicts an SDS-PAGE gel analysis of E. coli XL-1Blue (pHTT5) expressing SrtA$_{DN}$, in which the NH$_2$-terminal membrane anchor of sortase (SrtA) has been replaced with a six histidine tag. Lane 1 contains uninduced culture; 2, 1 mM IPTG induced culture; 3, French press extract; 4, the supernatant of centrifuged French press extracts; 5, the sediment of French press extracts; 6, flow-through of affinity chromatography on Ni-NTA; 7, column wash; 8–10, 1 ml fractions eluted with 0.5 M imidazole.
(C) is a bar graph depicting the effect of incubating purified SrtA$_{DN}$ was incubated with the peptide substrate DABCYL-QALPETGEE-EDANS and cleavage monitored as an increase in fluorescence. The reaction was inhibited by the addition of methanethiosulfonate (MTSET) or organic mercurial (pHMB), while the addition of 0.2 M NH$_2$OH accelerated cleavage. MTSET-treated SrtA$_{DN}$ could be rescued by incubation with 10 mM DTT.

Figure 15:
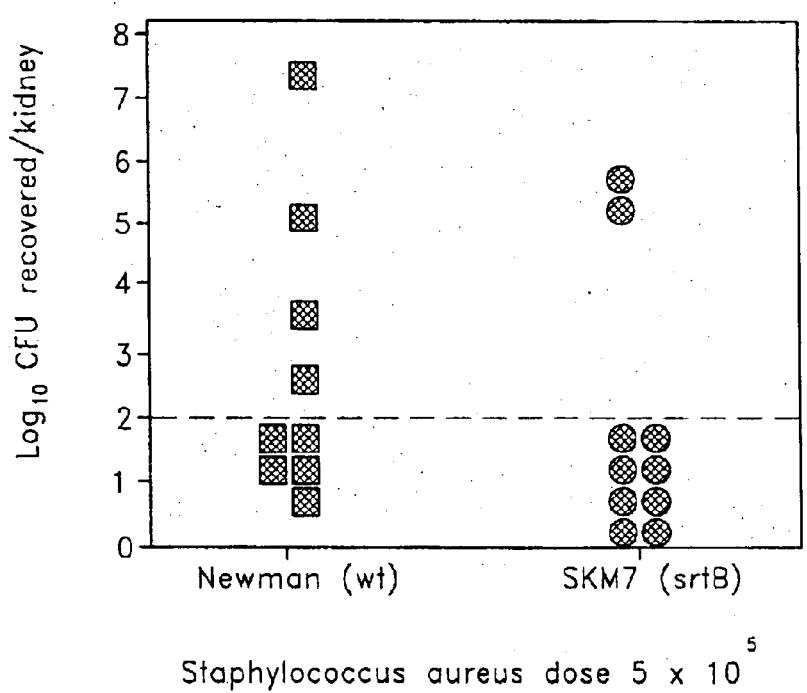

FIG. 15 depicts the effect of srtB knockout mutation on S. aureus staphylococcal host infectivity as indicated by number of staphylococci abscesses obtained per kidney in animals infected with either wild-type S. aureus Newman or isogenic srtB:ermC knockout variant (SKM7).

DEFINITIONS

As used herein, the terms defined below have the following meanings unless otherwise indicated:

"Nucleic Acid Sequence": the term "nucleic acid sequence" includes both DNA, DNA complements and RNA unless otherwise specified, and, unless otherwise specified, includes both double-stranded and single-stranded nucleic acids. Also included are hybrids such as DNA-RNA hybrids. In particular, a reference to DNA includes RNA that has either the equivalent base sequence except for the substitution of uracil and RNA for thymine in DNA, or has a complementary base sequence except for the substitution of uracil for thymine, complementarity being determined according to the Watson-Crick base pairing rules. Reference to nucleic acid sequences can also include modified bases as long as the modifications do not significantly interfere either with binding of a ligand such as a protein by the nucleic acid or with Watson-Crick base pairing.

"Mismatch": as used herein the term "mismatch" includes all unpaired bases when two nucleic acid sequences are hybridized with best alignment in the context of nucleic acid hybridization. In other words, the term "mismatch" includes not only situations in which the same number of bases are present in the two sequences or segments of sequences, but in which some bases do not form Watson-Crick pairs because of their sequences, but also situations in which different numbers of bases are present in the two sequences because of insertions or deletions, referred to generically as "indels." In this latter situation, certain of the bases in the longer sequence must be unpaired and may loop out from the hybrid.

"Match": as used herein the term "match" includes all paired amino acids when two amino acid sequences are compared with best alignment in the context in terms of protein sequence comparison. Amino acid "sequence identity" percentages include only identical amino acid pairing when amino acid sequences are matched in best alignment. Amino acid "sequence similarity" percentages include both similar and identical amino acids when amino acid sequences are matched in best alignment. Similar amino acids are amino acids which share similar physical and/or chemical properties. The following is a listing of amino acids which are considered to be similar, or conservative amino acids relative to one another, as substitutions of each of these amino acids for the other in a sequence often do not disrupt the structure or function of the molecule as the amino acids share similar physical and/or chemical properties. In particular, the conservative amino acid substitutions can be any of the following: (1) any of isoleucine for leucine or valine, leucine for isoleucine, and valine for leucine or isoleucine; (2) aspartic acid for glutamic acid and glutamic acid for aspartic acid; (3) glutamine for asparagine and asparagine for glutamine; and (4) serine for threonine and threonine for serine.

Other substitutions can also be considered conservative, depending upon the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the different pK's of these two amino acid residues or their different sizes are not significant. Still other changes can be considered "conservative" in particular environments. For example, if an amino acid on the surface of a protein is not involved in a hydrogen bond or salt bridge interaction with another molecule, such as another protein subunit or a ligand bound by the protein, negatively charged amino acids such as glutamic acid and aspartic acid can be substituted for by positively charged amino acids such as lysine or arginine and vice versa. Histidine (H), which is more weakly basic than arginine or lysine, and is partially charged at neutral pH, can sometimes be substituted for these more basic amino acids. Additionally, the amides glutamine (Q) and asparagine (N) can sometimes be substituted for their carboxylic acid homologues, glutamic acid and aspartic acid.

"Antibody": as used herein the term "antibody" includes both intact antibody molecules of the appropriate specificity, and antibody fragments (including Fab, F(ab'), Fv, and F(ab')$_2$), as well as chemically modified intact antibody molecules and antibody fragments, including hybrid antibodies assembled by in vitro reassociation of subunits. Also included are single-chain antibody molecules generally denoted by the term sFv and humanized antibodies in which some or all of the originally non-human constant regions are replaced with constant regions originally derived from human antibody sequences. Both polyclonal and monoclonal antibodies are included unless otherwise specified. Additionally included are modified antibodies or antibodies conjugated to labels or other molecules that do not block or alter the binding capacity of the antibody.

DETAILED DESCRIPTION OF THE PREFERRED EMBODIMENTS

A substantially purified sortase-transamidase enzyme from Gram-positive bacteria, particularly *Staphylococcus aureus*, has been identified and purified. The genome of gram-positive bacteria harbor more than one sortase and secretion gene. Both SrtA and SrtB cleave polypeptides bearing an LPXTG motif and are required for establishment of animal infection. The properties of these enzymes make them logical targets for antibiotic action. These enzymes also catalyze covalent crosslinkage of proteins to the peptidoglycan of Gram-positive bacteria.

I. A Sortase-Transamidase Enzyme

One aspect of the invention is a substantially purified sortase-transamidase enzyme from a Gram-positive bacterium. As used herein, the term "substantially purified" means having a specific activity of at least tenfold greater than the sortase-transamidase activity present in a crude extract, lysate, or other state from which proteins have not been removed and also in substantial isolation from proteins found in association with sortase-transamidase in the cell.

A sortase-transamidase enzyme has a molecular weight of about 23,539 daltons or of about 29,076 daltons. The enzyme catalyzes a reaction that covalently crosslinks the carboxyl-terminus of a protein having a sorting signal to the peptidoglycan of the Gram-positive bacterium. The sorting signal has: (1) a motif of $LPX_3X_4G$ therein; (2) a substantially hydrophobic domain of at least 31 amino acids carboxyl to the motif; and (3) a charged tail region with at least two positively charged residues carboxyl to the substantially hydrophobic domain, at least one of the two positively charged residues being arginine, the two positively charged residues being located at residues 31–33 from the motif. In this sorting signal, $X_3$ can be any of the twenty naturally-occurring L-amino acids. $X_4$ can be alanine, serine, or threonine. Preferably, $X_4$ is threonine.

Sortase-transamidases are believed to occur in all Gram-positive bacteria. In particular, the enzymes exists in Mycobacterium, Nocardia, Actinomyces, Staphylococcus, Streptococcus, Listeria, Enterococcus, and Pneumococcus. Specifically, the enzymes exist in the following species: *Staphylococcus aureus, S. sobrinus, Enterococcus faecalis, Streptococcus pyogenes*, and *Listeria monocytogenes*.

Preferably an enzyme is isolated from *Staphylococcus aureus*, and more preferably is a product of the srtA gene or the srtB gene of *S. aureus*.

A. Amino Acid Sequence

A sortase-transamidase of the present invention includes therein an amino acid sequence of:

M-K-K-W-T-N-R-L-M-T-I-A-G-V-V-L-I-L-V-A-A-Y-L-F-A-K-P-H-I-D-N-Y-L-

H-D-K-D-K-D-E-K-I-E-Q-Y-D-K-N-V-K-E-Q-A-S-K-D-K-K-Q-Q-A-K-P-Q-I-P-K-D-K-S-K-

V-A-G-Y-I-E-I-P-D-A-D-I-K-E-P-V-Y-P-G-P-A-T-P-E-Q-L-N-R-G-V-S-F-A-E-E-N-E-S-L-

D-D-Q-N-I-S-I-A-G-H-T-F-I-D-R-P-N-Y-Q-F-T-N-L-K-A-A-K-K-G-S-M-V-Y-F-K-V-G-N-E-

T-R-K-Y-K-M-T-S-I-R-D-V-K-P-T-D-V-G-V-L-D-E-Q-K-G-K-D-K-Q-L-T-L-I-T-C-D-D-Y-N-

E-K-T-G-V-W-E-K-R-K-I-F-V-A-T-E-V-K (SEQ ID NO:3); or an amino acid sequence of:

M-R-M-K-R-F-L-T-I-V-Q-I-L-L-V-V-I-I-I-F-G-Y-K-I-V-Q-T-Y-I-E-D-K-Q-E-R-A-N-Y-E-K-

L-Q-Q-K-F-Q-M-L-M-S-K-H-Q-A-H-V-R-P-Q-F-E-S-L-E-K-I-N-K-D-I-V-G-W-I-K-L-S-G-T-

S-L-N-Y-P-V-L-Q-G-K-T-N-H-D-Y-L-N-L-D-F-E-R-E-H-R-R-K-G-S-I-F-M-D-F-R-N-E-L-

K-I-L-N-H-N-T-I-L-Y-G-H-H-V-G-D--N-T-M-F-D-V-L-E-D-Y-L-K-Q-S-F--Y-E-K-H-K-I-I-E-

F-D-N-K-Y-G-K-Y-Q-L-Q-V-F-S-A-Y-K-T-T-K-D-N-Y-I-R-T-D-F-E-N-D-Q-D-Y-Q-Q-F-

L-D-E-T-K-R-K-S-V-I-N-S-D-V-N-V-T-V-K-D-K-I-M-T-L-S-T-C-E-D-A-Y-S-E-T-T-K-R-I-V-

V-V-A-K-I-I-K-V-S (SEQ ID NO:38)

Also within the scope of the present invention are substantially purified protein molecules that are mutants of the sequence of SEQ ID NO:3 or of SEQ ID NO:38 that preserve the sortase-transamidase activity. In particular, conservative amino acid substitutions can be any of the following: (1) any of isoleucine for leucine or valine, leucine for isoleucine, and valine for leucine or isoleucine; (2) aspartic acid for glutamic acid and glutamic acid for aspartic acid; (3) glutamine for asparagine and asparagine for glutamine; and (4) serine for threonine and threonine for serine.

Other substitutions can also be considered conservative, depending upon the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the different pK's of these two amino acid residues or their different sizes are not significant. Still other changes can be considered "conservative" in particular environments. For example, if an amino acid on the surface of a protein is not involved in a hydrogen bond or salt bridge interaction with another molecule, such as another protein subunit or a ligand bound by the protein, negatively charged amino acids such as glutamic acid and aspartic acid can be substituted for by positively charged amino acids such as lysine or arginine and vice versa. Histidine (H), which is more weakly basic than arginine or lysine, and is partially charged at neutral pH, can sometimes be substituted for these more basic amino acids. Additionally, the amides glutamine (Q) and asparagine (N) can sometimes be substituted for their carboxylic acid homologues, glutamic acid and aspartic acid.

The amino acid sequence of SrtA (SEQ ID NO:3) and SrtB (SEQ ID NO:38) are homologous, sharing 22% identity and 37% similarity. The amino acid sequence (SEQ ID NO:3 or SEQ ID NO:38) of a sortase-transamidase from *Staphylococcus aureus* also has substantial homology with sequences of enzymes from other Gram-positive bacteria. For example, for SrtA there is about a 31% sequence identity (and about 44% sequence similarity) with best alignment over the entire sequenced region of the *S. pyogenes* open reading frame (SEQ.ID NO.4). There is about a 28% sequence identity (and about 44% sequence similarity) with best alignment over the entire sequenced region of the *A. naeslundii* open reading frame (SEQ. ID NO.5). There is about a 27% sequence identity (and about 47% sequence similarity) with best alignment over the entire sequenced region of the *S. mutans* open reading frame (SEQ. ID NO.7). There is about a 25% sequence identity (and about 45% sequence similarity) with best alignment over the entire sequenced region of the *E. faecalis* open reading frame (SEQ. ID NO.6). There is about a XX % sequence identity (and about XX % sequence similarity) with best alignment over the entire sequenced region of the *B. subtilis* open reading frame (SEQ. ID NO.8). However, higher sequence identity 23% (and about 38% sequence similarity) exist between the *B. subtilis* and *S. mutans* amino acid sequences. These matches are shown in FIG. 7. Therefore, another aspect of the present invention is a substantially purified protein molecule that has at least a 18% sequence identity match, preferably a 20% sequence identity match, and most preferably a 30% sequence identity match with best alignment with the *S. pyogenes, A. naeslundii, S. mutans, E. faecalis* or *B. subtilis* open reading frame of FIG. 7A and that has sortase-transamidase activity. Further, another aspect of the present invention is a substantially purified protein molecule that has at least a 30% sequence similarity match, preferably a 40% sequence similarity match, and most preferably a 50% sequence similarity match with best alignment with the *S. pyogenes, A. naeslundii, S. mutans, E. faecalis* or *B. subtilis* open reading frame of FIG. 7A and that has sortase-transamidase activity.

The sortase-transamidase is a cysteine protease.

B. Activity of the Sortase-Transamidase

Figure 1:
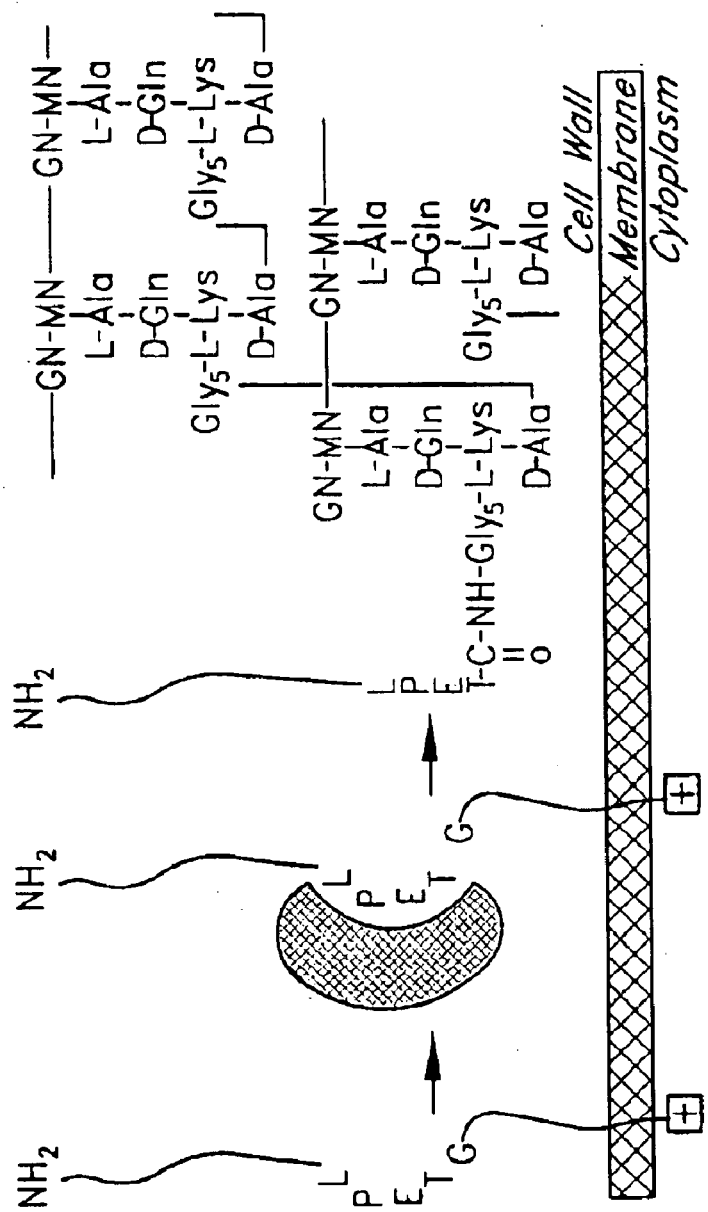
FIG. 1 is a diagram of the activity of the sortase-transamidase enzyme of the present invention.

Activity of the sortase-transamidase enzymes of the present invention is shown, in general, in FIG. 1. The enzyme first cleaves a polypeptide having a sorting signal within the $LPX_3X_4G$ motif. Cleavage occurs after residue $X_4$, normally a threonine; as indicated above, this residue can also be a serine or alanine residue. This residue forms a covalent intermediate with the sortase. The next step is the transamidation reaction that transfers the cleaved carboxyl terminus of the protein to be sorted to the $—NH_2$ of the pentaglycine crossbridge within the peptidoglycan precursor. The peptidoglycan precursor is then incorporated into the cell wall by a transglycosylase reaction with the release of undecaprenyl phosphate. The mature anchored polypeptide chains are thus linked to the pentaglycine cross bridge in the cell wall which is tethered to the ε-amino side chain of an unsubstituted cell wall tetrapeptide. A carboxypeptidase may cleave a D-Ala-D-Ala bond of the pentapeptide structure to yield the final branched anchor peptide in the staphylococcal cell wall.

The sorting signal has: (1) a motif of $LPX_3X_4G$ therein; (2) a substantially hydrophobic domain of at least 31 amino acids carboxyl to the motif; and (3) a charged tail region.

In the motif, $X_3$ can be any of the 20 naturally-occurring L-amino acids. $X_4$ can be any of threonine, serine, or alanine. Preferably, $X_4$ is threonine (O. Schneewind et al., "Cell Wall Sorting Signals in Surface Proteins of Gram-Positive Bacteria," EMBO J. 12:4803–4811 (1993)).

Preferably, the substantially hydrophobic domain carboxyl to the motif includes no more than about 7 charged residues or residues with polar side chains. For the purposes of this specification, these residues include the following: aspartic acid, glutamic acid, lysine, and arginine as charged residues, and serine, threonine, glutamine, and asparagine as polar but uncharged residues. Preferably, the sequence includes no more than three charged residues.

Representative sequences suitable for sorting signals for use with a sortase-transamidase of the present invention include, but are not limited to the following: E-E-N-P-F-I-G-T-T-V-F-G-G-L-S-L-A-L-G-A-A-L-L-A-G (SEQ ID NO:9), the hydrophobic domain of the staphylococcal proteinase (SPA) sorting signal from *Staphylococcus aureus*; (2) G-E-E-S-T-N-K-G-M-L-F-G-G-L-F-S-I-L-G-L-A-L-L (SEQ ID NO:10), the SNBP signal of *S. aureus*; (3) D-S-S-N-A-Y-L-P-L-L-G-L-V-S-L-T-A-G-F-S-L-L-G-L (SEQ ID NO:11), the SPM signal of *S. sobrinus*, (4) E-K-Q-N-V-L-L-T-V-V-G-S-L-A-A-M-L-G-L-A-G-L-G-F (SEQ ID NO:12), the PRGB signal of *Enterococcus faecalis*, (5) S-I-G-T-Y-L-F-K-I-G-S-A-A-M-I-G-A-I-G-I-Y-I-V (SEQ ID NO:13), the TEE signal of *Streptococcus pyogenes*, and (6) D-S-D-N-A-L-Y-L-L-L-G-L-L-A-V-G-T-A-M-A-L-T (SEQ ID NO:14), the INLA signal of *Listeria monocytogenes*. Other hydrophobic domains can be used as part of the sorting signal.

The third portion of the sorting signal is a charged tail region with at least two positively charged residues carboxyl to the substantially hydrophobic domain. At least one of the two positively charged residues is arginine. The charged tail can also contain other charged amino acids, such as lysine. Preferably, the charged tail region includes two or more arginine residues. The two positively charged residues are located at residues 31–33 from the motif. Preferably, the two arginine residues are either in succession or are separated by no more than one intervening amino acid. Preferably, the charged tail is at least five amino acids long, although four is possible. Among the charged tails that can be used are the following: (1) R-R-R-E-L (SEQ ID NO:15), from the SPA signal of *S. aureus*; (2) R-R-N-K-K-N-H-K-A (SEQ ID NO:16), from the SNBP signal of *S. aureus*; (3) R-R-K-Q-D (SEQ ID NO:17), from the SPAA signal of *S. sobrinus*; (4) K-R-R-K-E-T-K (SEQ ID NO:18), from the PRGB signal of *E. faecalis;* (5) K-R-R-K-A (SEQ ID NO:19), from the TEE signal of *S. pyogenes;* (6), K-R-R-H-V-A-K-H (SEQ ID NO:20), from the FIM sorting signal of *Actinomyces viscosus*, and (7) K-R-R-K-S (SEQ ID NO:21), from the BAC sorting signal of *Streptococcus aglactiae*; (8) K-R-K-E-E-N (SEQ ID NO:22), from the EMM signal of *Streptococcus pyogenes*.

Also usable as the charged tail portion of the sorting signal are the following sequences produced by mutagenesis from the SPA signal of *S. aureus*. These include R-R-R-E-S (SEQ ID NO:23), R-R-R-S-L (SEQ ID NO:24), R-R-S-E-L (SEQ ID NO:25), R-S-R-E-L (SEQ ID NO:26) and S-R-R-E-L (SEQ ID NO:27). Other charged tails that are usable as part of the sorting signal can be derived from a polyserine tail, itself inactive, by replacement of one or more of the serine residues with the basic amino acid arginine. These include R-R-S-S-S (SEQ ID NO:28), R-S-R-S-S (SEQ ID NO:29), and S-R-R-S-S (SEQ ID NO:30). Other sorting signals can also be used.

II. Genes Encoding Sortase-Transamidase Enzyme

A. Isolation of the Sortase-Transamidase Enzyme Gene

Genes for the sortase-transamidase enzymes SrtA and SrtB in *Staphylococcus aureus*, have been isolated. The isolation process is described in detail in the Examples Section below; in general, this process comprises: (1) the generation of temperature-sensitive mutants through chemical mutagenesis, such as with the DNA modifying agent N-methyl-N-nitro-N-nitrosoguanidine; (2) screening for temperature-sensitive mutants; (3) screening the temperature-sensitive mutants for a block in protein sorting by the use of a construct harboring the staphylococcal enterotoxin B (SEB) gene fused to the cell wall sorting signal of staphylococcal Protein A (SPA), to locate mutants that accumulate a precursor molecule formed by cleavage of an amino-terminal signal peptide but that is not then processed by cleavage of the carboxyl-terminal sorting signal; (4) generation of a *S. aureus* chromosomal library and complementation of the temperature-sensitive sorting defect; and (5) sequencing and characterization of the *S. aureus* complementing determinants.

B. Sequence of Sortase-Transamidase Genes

The above procedure yielded the entire coding sequence for the sortase-transamidase gene, srtA. This sequence is:

ATGAAAAAATGGACAAATCGATTAATGACAATCGCTGGTGTGGTACTTAT

CCTAGTGGCAGCATATTTGTTTGCTAAACCACATATCGATAATTATCTTC

ACGATAAAGATAAAGATGAAAAGATTGAACAATATGATAAAAATGTAAAA

GAACAGGCGAGTAAAGATAAAAAGCAGCAAGCTAAACCTCAAATTCCGAA

AGATAAATCGAAAGTGGCAGGCTATATTGAAATTCCAGATGCTGATATTA

AAGAACCAGTATATCCAGGACCAGCAACACCTGAACAATTAAATAGAGGT

GTAAGCTTTGCAGAAGAAAATGAATCACTAGATGATCAAAATATTTCAAT

TGCAGGACACACTTTCATTGACCGTCCGAACTATCAATTTACAAATCTTA

AAGCAGCCAAAAAAGGTAGTATGGTGTACTTTAAAGTTGGTAATGAAACA

CGTAAGTATAAAATGACAAGTATAAGAGATGTTAAGCCTACAGATGTAGG

AGTTCTAGATGAACAAAAAGGTAAAGATAAACAATTAACATTAATTACTT

GTGATGATTACAATGAAAAGACAGGCGTTTGGGAAAAACGTAAAATCTTT

GTAGCTACAGAAGTCAAATAA (SEQ ID NO: 2).

The last three nucleotides, TAA, of this sequence are the stop codon.

Blast searches using the srtA gene as query yielded the entire coding sequence for a second sortase-transamidase gene, srtB. This sequence is:

AAAAACCCTTGTGGTGTCACTGTACCTGATAAAGATTCAGCAACTTTCAT

GTTTATTTCAAAAACTTCTTGCGCGTATGCGATAATTTGCTGATCTAATC

TTGCCGGTTCAATTGCAAATAATTGTGTAATTACAATTCCACTTTGATAA

GCTTCTTCAATTAAATGCACACCTTCAATTAAAGCTAATCCAGTTTTATC

CCTCTCACGTTTCTTTTTAGCTTGTTCGCTTGTTTAATTCTATTATTTT

GTGCAGAAGTAATTTGTTCCATTGATAGCTCCTCGCTTTATTTTTAAAAA

TAAAAATATTAATCATTAATAAGATGAAAACATTTGATTGTATAGTTAAT

ATTAATTAATCGCTTTTATCACTCATAATATTTCAAATTGTATAAATTTC

TTTTATCGATACTACTACTATAAATCATACGCCCCAAAATATCATTATTA

ATTCTTTTCTTCTTCAAAATAAATCAAAATGATATAATTGATGATTATTT

TCAAAGCACATTCAAATCAAACTATGTTTTAGCAATTTGTTGTTAGCATG

TTTGTGTTCATTAAAAAAACGACCATCATCGGTATCATGTATGGTCGTTA

CAAAAGCTAACAATACCAATTGTCATAACAAGTACTGCAACCTCTTTAAA

TTCAATTATTTCATGTAACTATAGCCTATATCATATGTAATTACTTTGTT

ATTTATAATCGGGCTACTTTCATCTTCATTTTTACTTCTAACATGTTTAT

GCGCTGCTTTAAAGACATCAGATTTTAACCAATCCGTAAAAGCTTGCTTT

GATTTCCAAACTGTTAAAATTTTCACTTCATCAAAATCTTCTTGTTCTAA

AGTTTGTGTAACAAACATGCCATCAAAGCCTTCTAATGTTTCAATCCCAT

GTCTCGTGTAAAATCGTTCTATAATATCTTTTGCTGTTCCTTTTGTTAAC

GTCAGCCTATTTTCTGCCATAAATTTCATAATTATCCTCTTTTCTGTTTA

ACTTACCTTAATTATTTTTGCGACAACAACAATTCTTTTCGTCGTTTCAC

TATATGCATCTTCGCACGTTGATAAAGTCATTATTCTATCTTTTACCGTT

ACATTAACATCTGAATTAATTACAGATTTACGTTTTGTCTCATCTAAAAA

TTGTTGATAATCTTGATCATTTTCAAAATCTGTACGTATGTAATTATCTT

TAGTAGTAGTTTTATATGCACTAAATACTTGCAATTGATATTTACCATAT

TTATTGTCAAATTCAATTATCTTGTGTTTTTCATAAAACGATTGCTTTAA

ATAATCTTCTAACACATCAAACATCGTATTATCACCGACATGGTGCCCGT

ATAAAATAGTATTATGATTTAAATTCTTCAATTCATTTCTAAAATCCATA

AAAATACTACCTTTACGTCGATGTTCTCGCTCAAAATCTAAATTTAAATA

ATCGTGATTTGTCTTACCTTGTAGTACTGGATAATTTAATGATGTTCCTG

ATAATTTTATCCATCCAACAATGTCTTTATTTATTTTTTCAAGTGATTCA

AATTGTGGTCTCACATGTTCTTGATGTTTGCTCATCAGCATTTGAAATTT

TTGTTGTAATTTCTCATAATTTGCGCGTTCTTGCTTGTCTTCAATATATG

TTTGAACAATTTTGTAACCAAAAATGATAATAATTACAACCAATAAAATT

TGTACAATAGTTAAAAATCGCTTCATTCTCATAAAAATCCTCTTTTATTA

ACGACGTTTCTTCAGTCATCACTAAACCAGTTGTTGTACCGTTTTAGATT

CGATTTCGTTGACTTTGACAAATTAAGTAAATTAGCATTGGACCACCGAC

AATCATTAAAATAGCATTGGCTGGAATTTCTAAAGGAGGCTGTATCACTC

GTCCTAATAAATCAGCCACTAACAATAGCCATGCACCAATAACTGTAGAA

AACGGAATAAGTACTCTGTAATTGCCCCCAACTAGCTTTCTAACCACATG

TGGCACAATAATACCTAAAAAGGCTAGTTGTCCAACAATCGCAACAGTTG

CACTTGCTAAAAATACTGCTAATAAACCTGTTAACCATCTGTAACGATCA

ATATTAAAACCGATACTTCGCGCTTGTATGTCGTCTAAATTTAGTAAATT

CAATTTAGGGGACAATAGTAATGTTAATATTAATCCCAATAATGCTGATA

CTGCTAATATGTATACGTCGCTCCATATTTTCATTGTTAAGCCTTGAGGA

ATTTTCATTAAAGGGTTTTGAGTTAAAATTTCTAAAACACCATTTAATAA

TACGAATAACGCAACACCTACTAATATCATACTTACAGCATTGAATCTAA

ATTTAGAATGCAACAATATAATTATTAAAAATGGTATTAAACCTCCAATA

AAACTTAATAATGGTAAGTAAAAGTACAATTGTGGAATAAACAACATACA

AAGTGCTCTCATTATAAGTGCACCTGAGGAAACGCCAATGATATTCGCCT

CTGCCAAAGGATTTTGTAGTGCTGCTTGTAATAATGCTCCAGAAACTGCT

AACATTGCGCCAACCATCAATGCAATTAATATACGTGGCAATCGCAAATC

AATGATTGAATCCACTGCTTCATTGCTACCAGTTGTAAATTTTGTAAATA

-continued
GGTCATTAAATGACAATTTAATTGTACCGGTTACAAACGAAATATAAGCA

GTTGCGATTAAAATGACTAACAAACATAAAAA (SEQ ID NO: 37).

The complementary sequence for the sortase-transamidase gene, srtA gene is:

5'-TTATTTGACTTCTGTAGCTACAAAGATTTTACGTTTTTCCCAAACGC

CTGTCTTTTCATTGTAATCATCACAAGTAATTAATGTTAATTGTTTATCT

TTACCTTTTTGTTCATCTAGAACTCCTACATCTGTAGGCTTAACATCTCT

TATACTTGTCATTTTATACTTACGTGTTTCATTACCAACTTTAAAGTACA

CCATACTACCTTTTTTGGCTGCTTTAAGATTTGTAAATTGATAGTTCGGA

CGGACGGTCAATGAAAGTGTGTCCTGCAATTGAAATATTTTGATCATCTA

GTGATTCATTTTCTTCTGCAAAGCTTACACCTCTATTTAATTGTTCAGGT

GTTGCTGGTCCTGGATATACTGGTTCTTTAATATCAGCATCTGGAATTTC

AATATAGCCTGCCACTTTCGATTTATCTTTCGGAATTTGAGGTTTAGCTT

GCTGCTTTTTATCTTTACTCGCCTGTTCTTTTACATTTTTATCATATTGT

TCAATCTTTTCATCTTTATCTTTATCGTGAAGATAATTATCGATATGTGG

TTTAGCAAACAAATATGCTGCCACTAGGATAAGTACCACACCAGCGATTG

TCATTAATCGATTTGTCCATTTTTTCAT-3'

(SEQ ID NO: 39).

The complementary sequence for the sortase-transamidase gene, srtB is:

5'-TGAAATAAACATGAAAGTTGCTGAATCTTTATCAGGTACAGTGACAC

CACAAGGGTTTTTATTTGCAATTGAACCGGCAAGATTAGATCAGCAAATT

ATCGCATACGCGCAAGAAGTTTTAATTGAAGGTGTGCATTTAATTGAAGA

AGCTTATCAAAGTGGAATTGTAATTACACAATTAATTAAACAAGCGAACA

AGCTAAAAAAGAAACGTGAGAGGGATAAAACTGGATTAGCTTTTTTTTAA

AAATAAAGCGAGGAGCTATCAATGGAACAAATTACTTCTGCACAAAATAA

TAGATTAATTAATATTAACTATACAATCAAATGTTTTCATCTTATTAATG

ATTAATATTTTTATAGTAGTAGTATCGATAAAAGAAATTTATACAATTTG

AAATATTATGAGTGATAAAAGCGATTTTGATTTATTTTGAAGAAGAAAAG

AATTAATAATGATATTTTGGGGCGTATGATTTAACAAATTGCTAAAACAT

AGTTTGATTTGAATGTGCTTTGAAAATAATCATCAATTATATCTAACGAC

CATACATGATACCGATGATGGTCGTTTTTTTAATGAACACAAACATGCTA

ACAAATAATTGAATTTAAAGAGGTTGCAGTACTTGTTATGACAATTGGTA

TTGTTAGCTTTTGAAAGTAGCCCGATTATAAATAACAAAGTAATTACATA

TGATATAGGCTATAGTTACATGAGGTTAAAATCTGATGTCTTTAAAGCAG

CGCATAAACATGTTAGAAGTAAAAATGAAGATGAAGATTTTGATGAAGTG

AAAATTTTAACAGTTTGGAAATCAAAGCAAGCTTTTACGGATTATGGGAT

TGAAACATTAGAAGGCTTTGATGGCATGTTTGTTACACAAACTTTAGAAC

-continued
AAGATAGGCTGACGTTAACAAAAGGAACAGCAAAAGATATTATAGAACGA

TTTTACACGAGACCAAAAATAATTAAGGTAAGTTAAACAGAAAAGAGGAT

AATTATGAAATTTATGGCAGAAATGACTTTATCAACGTGCGAAGATGCAT

ATAGTGAAACGACGAAAAGAATTGTTGTTGTCGAGACAAAACGTAAATCT

GTAATTAATTCAGATGTTAATGTAACGGTAAAAGATAGAATAAAAGATAA

TTACATACGTACAGATTTTGAAAATGATCAAGATTATCAACAATTTTTAG

ATGTTGACAATAAATATGGTAAATATCAATTGCAAGTATTTAGTGCATAT

AAAAACTACTACTATTGATGTGTTAGAAGATTATTTAAAGCAATCGTTTTA

TGAAAAACACAAGATAATTGAATTGAAGAATTTAAATCATAATACTATTT

TATACGGGCACCATGTCGGTGATAATACGATGTTAGATTTTGAGCGAGAA

CATCGACGTAAAGGTAGTATTTTTATGGATTTTAGAAATGAATCAGGAAC

ATCATTAAATTATCCAGTACTACAAGGTAAGACAAATCACGATTATTTAA

ATTGACCACAATTTGAATCACTTGAAAAAATAAATAAAGACATTGTTGGA

TGGATAAAATTATATTATGAGAAATTACAACAAAAATTTCAAATGCTGAT

GAGCAAACATCAAGAACATGTGATTATCATTTTTGGTTACAAAATTGTTC

AAACATATATTGAAGACAAGCAAGAACGCGCAAGGATTTTTATGAGAATG

AAGCGATTTTTAACTATTGTACAAATTTTATTGGTTGTAATTAAATCTAA

AACGGTACAACAACTGGTTTAGTGATGACTGAAGAAACGTCGTTAATAAA

AGATTTAATGATTGTCGGTGGTCCAATGCTAATTTACTTAATTTGTCAAA

GTCAACGAAATCGAGTGGCTGATTTATTAGGACGAGTGATACAGCCTCCT

TTAGAAATTCCAGCCAATGCTATTGGGGCAATTACAGAGTACTTATTCC

GTTTTCTACAGTTATTGGTGCATGGCTATTGTTGATTGTTGGACAACTAG

CCTTTTTAGGTATTATTGTGCCACATGTGGTTAGAAAGCTAGTTGATCGT

TACAGATGGTTAACAGGTTTATTAGCAGTATTTTTAGCAAGTGCAACTGT

TGCCCCTAAATTGAATTTACTAAATTTAGACGACATACAAGCGCGAAGTA

TCGGTTTTAATATCGACGTATACATATTAGCAGTATCAGCATTATTGGGA

TTAATATTAACATTACTATTGTCAATTTTAACTCAAAACCCTTTAATGAA

AATTCCTCAAGGCTTAACAATGAAAATATGGAGTGCTGTAAGTATGATAT

TAGTAGGTGTTGCGTTATTCGTATTATTAAATGGTGTTTTAGATATTGGA

GGTTTAATACCATTTTTAATAATTATATTGTTGCATTCTAAATTTAGATT

CAAGAGAGCACTTTGTATGTTGTTTATTCCACAATTGTACTTTTACTTAC

CATTATTAAGTTTACTACAAAATCCTTTGGCAGAGGCGAATATCATTGGC

GTTTCCTCAGGTGCACTTATAATATTAATTGCATTGATGGTTGGCGCAAT

GTTAGCAGTTTCTGGAGCATTATTACAAGCAGCATTTACAACTGGTAGCA

ATGAAGCAGTGGATTCAATCATTGATTTGCGATTGCCACGTATTGCTTAT

ATTTCGTTTGTAACCGGTACAATTAAATTGTCATTTAATGACCTATTTAC

AAATTTTTATGTTTGTTAGTCATTTTAATCGCAAC-3'

(SEQ ID NO: 40).

Accordingly, within the scope of the present invention are nucleic acid sequences encoding a substantially purified sortase-transamidase enzyme from Gram-positive bacterium. The enzyme encoded have molecular weights of about 23,539 or about 29,076 daltons and catalyze a reaction that covalently cross-link the carboxyl-terminus of a protein having a sorting signal such as, for example, the sorting signal described above, to a peptidoglycan of a gram-positive bacterium. The sortase enzymes can also catalyze similar reactions using different surface protein substrates, thereby fulfilling similar, but non redundant functions in staphylococci. The nucleic acid sequences include the sequence of SEQ ID NO:2 or a sequence complementary to SEQ ID NO:2 (SEQ ID NO:39), or the sequence of SEQ ID NO:37 or a sequence complementary to SEQ ID NO:37 (SEQ ID NO:40).

Also included within the present invention is a nucleic acid sequence encoding a substantially purified sortase-transamidase enzyme from a Gram-positive bacterium with a molecular weight of about 23,539 or about 29,076 daltons, where the enzyme catalyzes a cross-linking reaction where the nucleic acid sequence hybridizes with at least one of: (1) the sequence of SEQ ID NO:2; (2) a sequence complementary to SEQ ID NO:2 (SEQ ID NO:39); (3) the sequence of SEQ ID NO:37; (4) a sequence complementary to SEQ ID NO:37 (SEQ ID NO:40); (5) a sequence complementary to SEQ ID NO:2 with no greater than about a 15% mismatch under stringent conditions; (6) or a sequence complementary to SEQ ID NO:37 with no greater than about a 15% mismatch under stringent conditions. Preferably, the degree of mismatch is no greater than about 5%; most preferably the mismatch is no greater than about 2%.

Also within the present invention is a nucleic acid sequence encoding a substantially purified sortase-transamidase enzyme from a Gram-positive bacterium with a molecular weight of about 23,539 or about 29,076 daltons and that catalyzes the cross-linking reaction described above involving the sorting signal, where the enzyme includes therein an amino acid sequence selected from the group consisting of:

valine for any other of these amino acids; (2) aspartic acid for glutamic acid and vice versa; (3) glutamine for asparagine and vice versa; and (4) serine for threonine and vice versa. Alternative nucleic acid sequences can be determined using the standard genetic code; the alternative codons are readily determinable for each amino acid in this sequence.

Construction of nucleic acid sequences according to the present invention can be accomplished by techniques well known in the art, including solid-phase nucleotide synthesis, the polymerase chain reaction (PCR) technique, reverse transcription of DNA from RNA, the use of DNA polymerases and ligases, and other techniques. If an amino acid sequence is known, the corresponding nucleic acid sequence can be constructed according to the genetic code.

C. Vectors and Host Cells Transformed with Vectors

Another aspect of the invention is a vector comprising a nucleic acid sequence according to the present invention operatively linked to at least one control sequence that controls the expression or regulation of the nucleic acid sequence. Such control sequences are well known in the art and include operators, promoters, enhancers, promoter-proximal elements and replication origins. The techniques of vector construction, including cloning, ligation, gap-filling, the use of the polymerase chain reaction (PCR) procedure, solid-state oligonucleotide synthesis, and other techniques, are all well known in the art and need not be described further here.

Another aspect of the present-invention is a host cell transfected with a vector according to the present invention. Among the host cells that can be used are gram-positive bacteria such as *Staphylococcus aureus*.

Transfection, also known as transformation, is done using standard techniques appropriate to the host cell used, particularly *Staphylococcus aureus*. Such techniques are described, for example, in R. P. Novick, "Genetic Systems (1) M-K-
K-W-T-N-R-L-M-T-I-A-G-V-V-L-I-L-V-A-A-Y-L-F-A-K-P-H-I-D-N-Y-L-H-D-K-D-K-D-E-K-I-
E-Q-Y-D-K-N-V-K-E-Q-A-S-K-D-K-K-Q-Q-A-K-P-Q-I-P-K-D-K-S-K-V-A-G-Y-I-E-I-P-D-A-
D-I-K-E-P-V-Y-P-G-P-A-T-P-E-Q-L-N-R-G-V-S-F-A-E-E-N-E-S-L-D-D-Q-N-I-S-I-A-G-H-
T-F-I-D-R-P-N-Y-Q-F-T-N-L-K-A-A-K-K-G-S-M-V-Y-F-K-V-G-N-E-T-R-K-Y-K-M-T-S-I-R-
D-V-K-P-T-D-V-G-V-L-D-E-Q-K-G-K-D-K-Q-L-T-L-I-T-C-D-D-Y-N-E-K-T-G-V-W-E-K-R-
K-I-F-V-A-T-E-V-K (SEQ ID NO:3); (2) M-R-M-K-R-F-L-T-I-V-Q-I-L-L-V-V-I-I-I-F-G-Y-
K-I-V-Q-T-Y-I-E-D-K-Q-E-R-A-N-Y-E-K-L-Q-Q-K-F-Q-M-L-M-S-K-H-Q-A-H-V-R-P-Q-F-
E-S-L-E-K-I-N-K-D-I-V-G-W-I-K-L-S-G-T-S-L-N-Y-P-V-L-Q-G-K-T-N-H-D-Y-L-N-L-D-F-
E-R-E-H-R-R-K-G-S-I-F-M-D-F-R-N-E-L-K-I-L-N-H-N-T-I-L-Y-G-H-H-V-G-D--N-T-M-F-
D-V-L-E-D-Y-L-K-Q-S-F---Y-E-K-H-K-I-I-E-F-D-N-K-Y-G-K-Y-Q-L-Q-V-F-S-A-Y-K-T-T-T-
K-D-N-Y-I-R-T-D-F-E-N-D-Q-D-Y-Q-Q-F-L-D-E-T-K-R-K-S-V-I-N-S-D-V-N-V-T-V-K-D-K-
I-M-T-L-S-T-C-E-D-A-Y-S-E-T-T-K-R-I-V-V-V-A-K-I-I-K-V-S (SEQ ID NO:38);

(3) sequences incorporating one or more conservative amino acid substitutions in SEQ ID NO:3 wherein the conservative amino acid substitutions are any of the following: (1) any of isoleucine, leucine and valine for any other of these amino acids; (2) aspartic acid for glutamic acid and vice versa; (3) glutamine for asparagine and vice versa; and (4) serine for threonine and vice versa; and (4) sequences incorporating one or more conservative amino acid substitutions in SEQ ID NO:38 wherein the conservative amino acid substitutions are any of the following: (1) any of isoleucine, leucine and in Staphylococci," Meth. Enzymol. 204: 587–636 (1991), as well as in O. Schneewind et al., "Sorting of Protein A to the Staphylococcal Cell Wall," Cell 70: 267–281 (1992).

III. Sortase-Transamidase as a Target for Antibiotic Action

A. A Site for Antibiotic Action

The reaction carried out by a sortase-transamidase of the present invention presents a possible target for a new class of antibiotics to combat medically relevant infections caused by numerous gram-positive organisms. Because this is a novel site of antibiotic action, these antibiotics have the advantage that resistance by the bacterium has not had a chance to develop.

The presence of more than one sortase gene in staphylococci indicates that sortase genes are essential for in vitro growth of staphylococci. Chemical inhibitors of sortase or other sortase inhibitors may therefore function as particularly useful and effective antibiotics or bactericidal compounds; and are particularly useful for treatment of human infections caused by Gram-positive bacteria. Such inhibitors are useful for treatment of any human infections caused by or resulting from Gram-positive bacteria. Such antibiotics can include compounds with structures that mimic the cleavage site, such as compounds with a structure similar to methyl methanethiosulfonate or, more generally, alkyl methanethiosulfonates. Alternatively, any compound, chemical, or inhibitor of sortase expression, function or activity can be effective as a antibiotic or bactericidal agent for use in the present invention.

The sortase-transamidases of the present invention are believed to be cysteine proteases. Other antibiotics that may inhibit the activity of the sortase-transamidase in the present invention include inhibitors that would be specific for cysteine-modification in a β-lactam framework. These inhibitors would have active moieties that would form mixed disulfides with the cysteine sulfhydryl. These active moieties could be derivatives of methanethiosulfonate, such as methanethiosulfonate ethylammonium, methanethiosulfonate ethyltrimethylammonium, or methanethiosulfonate ethylsulfonate (J. A. Javitch et al., "Mapping the Binding Site Crevice of the Dopamine D2 Receptor by the Substituted-Cysteine Accessibility Method," Neuron, 14: 825–831 (1995); M. H. Akabas & A. Karlin, "Identification of Acetylcholine Receptor Channel-Lining Residues in the M1 Segment of the α-Subunit," Biochemistry 34: 12496–12500 (1995)). Similar reagents, such as alkyl alkanethiosulfonates, i.e., methyl methanethiosulfonate, or alkoxycarbonylalkyl disulfides, have been described (D. J. Smith et al., "Simple Alkanethiol Groups for Temporary Blocking of Sulfhydryl Groups of Enzymes," Biochemistry 14: 766–771 (1975); W. N. Valentine & D. E. Paglia, "Effect of Chemical Modification of Sulfhydryl Groups of Human Erythrocyte Enzymes," Am. J. Hematol. 11: 111–124 (1981)). Other useful inhibitors involve derivatives of 2-trifluoroacetylaminobenzene sulfonyl fluoride (J. C. Powers, "Proteolytic Enzymes and Their Active-Site-Specific Inhibitors: Role in the Treatment of Disease," in Modification of Proteins), in a β-lactam framework, peptidyl aldehydes and nitriles (E. Dufour et al., "Peptide Aldehydes and Nitriles as Transition State Analog Inhibitors of Cysteine Proteases," Biochemistry 34: 9136–9143 (1995); J. O. Westerik & R. Wolfenden, "Aldehydes as Inhibitors of Papain," J. Biol. Chem. 247: 8195–8197 (1972)), peptidyl diazomethyl ketones (L. Björck et al., "Bacterial Growth Blocked by a Synthetic Peptide Based on the Structure of a Human Proteinase Inhibitor," Nature 337: 385–386 (1989)), peptidyl phosphonamidates (P. A. Bartlett & C. K. Marlowe, "Phosphonamidates as Transition-State Analogue Inhibitors of Thermolysin," Biochemistry 22: 4618–4624 (1983)), phosphonate monoesters such as derivatives or analogues of m-carboxyphenyl phenylacetamidomethylphosphonate (R. F. Pratt, "Inhibition of a Class C β-Lactamase by a Specific Phosphonate Monoester," Science 246: 917–919 (1989)), maleimides and their derivatives, including derivatives of such bifunctional maleimides as o-phenylenebismaleimide, p-phenylenebismaleimide, m-phenylenebismaleimide, 2,3-naphthalenebismaleimide, 1,5-naphthalenebismaleimide, and azophenylbismaleimide, as well as monofunctional maleimides and their derivatives (J. V. Moroney et al., "The Distance Between Thiol Groups in the γ Subunit of Coupling Factor 1 Influences the Proton Permeability of Thylakoid Membranes," J. Bioenerget. Biomembr. 14: 347–359 (1982)), peptidyl halomethyl ketones (chloromethyl or fluoromethyl ketones), peptidyl sulfonium salts, peptidyl acyloxymethyl ketones, derivatives and analogues of epoxides, such as E-64 (N-[N-(L-trans-carboxyoxiran-2-carbonyl)-L-leucylagmatine), E-64c (a derivative of E-64 in which the agmatine moiety is replaced by an isoamylamine moiety), E-64c ethyl ester, Ep-459 (an analogue of E-64 in which the agmatine moiety is replaced by a 1,4-diaminopropyl moiety), Ep-479 (an analogue of E-64 in which the agmatine moiety is replaced by a 1,7-diheptylamino moiety), Ep-460 (a derivative of Ep-459 in which the terminal amino group is substituted with a Z (benzyloxycarbonyl) group), Ep-174 (a derivative of E-64 in which the agmatine moiety is removed, so that the molecule has a free carboxyl residue from the leucine moiety), Ep-475 (an analogue of E-64 in which the agmatine moiety is replaced with a $NH_2$—$(CH_2)_2$—CH—$(CH_3)_2$ moiety), or Ep-420 (a derivative of E-64 in which the hydroxyl group is benzoylated, forming an ester, and the leucylagmatine moiety is replaced with isoleucyl-O-methyltyrosine), or peptidyl O-acyl hydroxamates (E Shaw, "Cysteinyl Proteases and Their Selective Inactivation), pp 271–347). Other inhibitors are known in the art.

B. Screening Methods

Another aspect of the present invention is a method for screening a compound for anti-sortase-transamidase activity. This is an important aspect of the present invention, because it provides a method for screening for compounds that disrupt the sorting process and thus have potential antibiotic activity against Gram-positive bacteria.

In general, this method comprises the steps of: (1) providing an active fraction of sortase-transamidase enzyme; (2) performing an assay for sortase-transamidase activity in the presence and in the absence of the compound being screened; and (3) comparing the activity of the sortase-transamidase enzyme in the presence and in the absence of the compound.

The active fraction of sortase-transamidase enzyme can be a substantially purified sortase-transamidase enzyme preparation according to the present invention, but can be a less purified preparation, such as a partially purified particulate preparation as described below.

The enzymatic activity can be measured by the cleavage of a suitable substrate, such as the construct having the Staphylococcal Enterotoxin B (SEB) gene fused to the cell wall sorting signal of Staphylococcal Protein A (SPA). The cleavage can be determined by monitoring the molecular weight of the products by sodium dodecyl sulfate-polyacrylamide gel electrophoresis or by other methods.

One particularly preferred assay for sortase-transamidase activity is the following:

Staphylococcal soluble RNA (sRNA) is prepared from *S. aureus* by a modification of the technique of Zubay (G. Zubay, J. Mol. Biol. 4: 347–356 (1962)). An overnight culture of *S. aureus* is diluted 1:10 in TSB and incubated at 37° C. for 3 hr. The cells are harvested by centrifugation at 6000 rpm for 15 min.

For every gram of wet cell pellets, 2 ml of 0.01 M magnesium acetate, 0.001 M Tris, pH 7.5 is used to suspend the pellets. The cell pellets are beaten by glass bead beater for 45 minutes in 5 minute intervals. The suspension is centrifuged twice at 2500 rpm for 5 minutes to remove the glass beads, then 0.5 ml phenol is added to the suspension. The suspension is vigorously shaken for 90 minutes at 4° C., and then centrifuged at 18,000× g for 15 minutes. The nucleic acids in the top layer are precipitated by addition of 0.1 volume of 20% potassium acetate and 2 volumes of ethanol, then stored at 4° C. for at least 36 hours. The precipitate is obtained by centrifugation at 5,000× g for 5 minutes. Cold NaCl (1 ml) is added to the precipitate and stirred at 4° C. for 1 hour. The suspension is centrifuged at 15,000× g for 30 minutes. The sediments are washed with 0.5 ml of cold 1 M NaCl. The supernatants are combined and 2 volumes of ethanol is added to precipitate the tRNA. The precipitate is suspended in 0.1 ml of 0.2 M glycine, pH 10.3 and incubated for 3 hr at 37° C. This suspension is then made 0.4 M in NaCl and the RNA is precipitated by addition of 2 volumes of ethanol. The precipitate is dissolved in 0.7 ml of 0.3 M sodium acetate, pH 7.0. To this is slowly added 0.5 volume of isopropyl alcohol, with stirring. The precipitate is removed by centrifugation at 8,000× g for 5 min. This precipitate is redissolved in 0.35 ml of 0.3 M sodium acetate, pH 7.0. To this is added 0.5 volume of isopropyl alcohol, using the same procedure as above. The precipitate is also removed by centrifugation. The combined supernatants from the two centrifugations are treated further with 0.37 ml of isopropyl alcohol. The resulting precipitate is dissolved in 75 μl of water and dialyzed against water overnight at 4° C. This sRNA is used in the sortase-transamidase assay.

Particulate sortase-transamidase enzyme is prepared for use in the assay by a modification of the procedure of Chatterjee & Park (A. N. Chatterjee & J. T. Park, Proc. Natl. Acad. Sci. USA 51: 9–16 (1964)). An overnight culture of *S. aureus* OS2 is diluted 1:50 in TSB and incubated at 37° C. for 3 hr. Cells are harvested by centrifugation at 6000 rpm for 15 minutes, and washed twice with ice-cold water. The cells are disrupted by shaking 7 ml of 13% suspension of cells in 0.05 M Tris-HCl buffer, pH 7.5, 0.1 mM $MgCl_2$, and 1 mM 2-mercaptoethanol with an equal volume of glass beads for 10–15 minutes in a beater. The glass beads are removed by centrifugation at 2000 rpm for 5 minutes. The crude extract is then centrifuged at 15,000× g for 5 minutes. The supernatant is centrifuged again at 100,000× g for 30 minutes. The light yellow translucent pellet is resuspended in 2 to 4 ml of 0.02 M Tris-HCl buffer, pH 7.5, containing 0.1 mM $MgCl_2$ and 1 mM 2-mercaptoethanol. This suspension represents the crude particulate enzyme and is used in the reaction mixture below.

The supernatant from centrifugation at 100,000× g is passed through gel filtration using a Sephadex® G-25 agarose column (Pharmacia) to remove endogenous substrates. This supernatant is also used in the reaction mixture.

The complete reaction mixture contains in a final volume of 30 μl (M. Matsuhashi et al., Proc. Natl. Acad. Sci. USA 54: 587–594 (1965)): 3 μmol of Tris-HCl, pH 7.8; 0.1 μmol of $MgCl_2$; 1.3 μmol of KCl; 2.7 nmol of [$^3$H] glycine (200 μCi/μmol); 2 nmol of UDP-M-pentapeptide; 5 nmol of UDP-N-acetylglucosamine; 0.2 μmol of ATP; 0.05 μmol of potassium phosphoenolpyruvate; 2.05 μg of chloramphenicol; 5 μg of pyruvate kinase; 0.025 μmol of 2-mercaptoethanol; 50 μg of staphylococcal sRNA prepared as above; 4 μg (as protein) of supernatant as prepared above; 271 μg of particulate enzyme prepared as above; and 8 nmol of a synthesized soluble peptide (HHHHHHAQALEPTGEENPF) (SEQ ID NO:32) as a substrate.

The mixture is incubated at 20° C. for 60 minutes. The mixture is then heated at 100° C. for 1 minute. The mixture is diluted to 1 ml and precipitated with 50 μl nickel resin, and washed with wash buffer (1% Triton X-100, 0.1% sodium dodecyl sulfate, 50 mM Tris, pH 7.5). The nickel resin beads are counted in a scintillation counter to determine $^3$H bound to the beads.

The effectiveness of the compound being screened to inhibit the activity of the sortase-transamidase enzyme can be determined by adding it to the assay mixture in a predetermined concentration and determining the resulting degree of inhibition of enzyme activity that results. Typically, a dose-response curve is generated using a range of concentrations of the compound being screened.

The particular enzyme preparation of sortase-transamidase employed in this protocol can be replaced with any other sortase-transamidase preparation, purified or crude, staphylococcal, recombinant, or from any other source from any other Gram-positive bacterium as described above.

The soluble peptide is captured in this embodiment by its affinity for nickel resin as a result of the six histidine residues. More than six histidine residues can be used in the peptide. As an alternative, the soluble peptide can be captured by an affinity resulting from other interactions, such as streptavidin-biotin, glutathione S-transferase-glutathione, maltose binding protein-amylose, and the like, by replacing the six histidine residues with the amino acid sequence that constitutes the binding site in the peptide and employing the appropriate solid phase affinity resin containing the binding partner. Suitable peptides can be prepared by solid phase peptide synthesis using techniques well known in the art, such as those described in M. Bodanszky, "Peptide Chemistry: A Practical Textbook" (2d ed., Springer-Verlag, Berlin, 1993). For example, if the glutathione S-transferase-glutathione interaction is used, the active site of glutathione S-transferase (D. B. Smith & K. S. Johnson, "Single-Step Purification of Polypeptides Expressed in *Escherichia coli* as Fusions with Glutathione S-Transferase," *Gene* 67: 31–40 (1988)) can be substituted for the six histidine residues, and glutathione can be bound to the solid support.

IV. Use of Sortase-Transamidase for Protein and Peptide Display

A. Methods for Protein and Peptide Display

The sortase-transamidase enzymes of the present invention can also be used in a method of displaying a polypeptide on the surface of a gram-positive bacterium.

In general, a first embodiment of this method comprises the steps of: (1) expressing a polypeptide having a sorting signal at its carboxyl-terminal end as described above; (2) forming a reaction mixture including: (i) the expressed polypeptide; (ii) a substantially purified sortase-transamidase enzyme; and (iii) a Gram-positive bacterium having a peptidoglycan to which the sortase-transamidase can link the polypeptide; and (3) allowing the sortase-transamidase to catalyze a reaction that cleaves the polypeptide within the $LPX_3X_4G$ motif of the sorting signal and covalently cross-links the amino-terminal portion of the cleaved polypeptide to the peptidoglycan to display the polypeptide on the surface of the Gram-positive bacterium.

In this method, the polypeptide having the sorting signal at its carboxy-terminal end need not be expressed in a Gram-positive bacterium; it can be expressed in another bacterial system such as *Escherichia coli* or *Salmonella typhimurium*, or in a eukaryotic expression system.

The other method for protein targeting and display relies on direct expression of the chimeric protein in a Gram-positive bacterium and the action of the sortase-transamidase on the expressed protein. In general, such a method comprises the steps of: (1) cloning a nucleic acid segment encoding a chimeric protein into a Gram-positive bacterium to generate a cloned chimeric protein including therein a carboxyl-terminal sorting signal as described above, the chimeric protein including the polypeptide to be displayed; (2) growing the bacterium into which the nucleic acid segment has been cloned to express the cloned chimeric protein to generate a chimeric protein including therein a carboxyl-terminal sorting signal; and (3) covalent binding of the chimeric protein to the cell wall by the enzymatic action of the sortase-transamidase involving cleavage of the chimeric protein within the $LPX_3X_4G$ motif so that the protein is displayed on the surface of the gram-positive bacterium in such a way that the protein is accessible to a ligand.

Typically, the Gram-positive bacterium is a species of Staphylococcus. A particularly preferred species of Staphylococcus is *Staphylococcus aureus*.

However, other Gram-positive bacteria such as *Streptococcus pyogenes*, other Streptococcus species, and Gram-positive bacteria of other genera can also be used.

Cloning the nucleic acid segment encoding the chimeric protein into the Gram-positive bacterium is performed by standard methods. In general, such cloning involves: (1) isolation of a nucleic acid segment encoding the protein to be sorted and covalently linked to the cell wall; (2) joining the nucleic acid segment to the sorting signal; (3) cloning by insertion into a vector compatible with the Gram-positive bacterium in which expression is to take place; and (4) incorporation of the vector including the new chimeric nucleic acid segment into the bacterium.

Typically, the nucleic acid segment encoding the protein to be sorted is DNA; however, the use of RNA in certain cloning steps is within the scope of the present invention.

When dealing with genes from eukaryotic organisms, it is preferred to use cDNA, because the natural gene typically contains intervening sequences or introns that are not translated. Alternatively, if the amino acid sequence is known, a synthetic gene encoding the protein to be sorted can be constructed by standard solid-phase oligodeoxyribonucleotide synthesis methods, such as the phosphotriester or phosphite triester methods. The sequence of the synthetic gene is determined by the genetic code, by which each naturally occurring amino acid is specified by one or more codons. Additionally, if a portion of the protein sequence is known, but the gene or messenger RNA has not been isolated, the amino acid sequence can be used to construct a degenerate set of probes according to the known degeneracy of the genetic code. General aspects of cloning are described, for example, in J. Sambrook et al., "Molecular Cloning: A Laboratory Manual" (2d ed., Cold Spring Harbor Laboratory Press, Cold Spring Harbor, N.Y., 1989); in B. Perbal, "A Practical Guide to Molecular Cloning" (2d ed., John Wiley & Sons, New York 1988), in S. L. Berger & A. R. Kimmel, "Guide to Molecular Cloning Techniques" (Methods in Enzymology, vol. 152, Academic Press, Inc., San Diego, 1987), and in D. V. Goeddel, ed., "Gene Expression Technology" (Methods in Enzymology, vol. 185, Academic Press, Inc., San Diego, 1991).

Once isolated, DNA encoding the protein to be sorted is then joined to the sorting signal. This is typically accomplished through ligation, such as using *Escherichia coli* or bacteriophage T4 ligase. Conditions for the use of these enzymes are well known and are described, for example, in the above general references.

The ligation is done in such a way so that the protein to be sorted and the sorting signal are joined in a single contiguous reading frame so that a single protein is produced. This may, in some cases, involve addition or deletion of bases of the cloned DNA segment to maintain a single reading frame. This can be done by using standard techniques.

Cloning is typically performed by inserting the cloned DNA into a vector containing control elements to allow expression of the cloned DNA. The vector is then incorporated into the bacterium in which expression is to occur, using standard techniques of transformation or other techniques for introducing nucleic acids into bacteria.

One suitable cloning system for *S. aureus* places the cloned gene under the control of the BlaZRI regulon (P. Z. Wang et al., Nucl. Acids Res. 19:4000 (1991)). Vectors and other cloning techniques for use in *Staphylococcus aureus* are described in B. Nilsson & L. Abrahmsen, "Fusion to Staphylococcal Protein A," in Gene Expression Technology, supra, p.144–161.

If the chimeric protein is cloned under control of the BlaZRI regulon, expression can be induced by the addition of the β-lactam antibiotic methicillin.

Another aspect of the present invention is a polypeptide displayed on the surface of a Gram-positive bacterium by covalent linkage of an amino-acid sequence of $LPX_3X_4$ derived from cleavage of an $LPX_3X_4G$ motif, as described above.

Yet another aspect of the present invention is a covalent complex comprising: (1) the displayed polypeptide; and (2) an antigen or hapten covalently cross-linked to the polypeptide.

B. Screening Methods

These polypeptides associated with the cell surfaces of Gram-positive bacteria can be used in various ways for screening. For example, samples of expressed proteins from an expression library containing expressed proteins on the surfaces of the cells can be used to screen for clones that express a particular desired protein when a labeled antibody or other labeled specific binding partner for that protein is available.

These methods are based on the methods for protein targeting and display described above.

A first embodiment of such a method comprises: (1) expressing a cloned polypeptide as a chimeric protein having a sorting signal at its carboxy-terminal end as described above; (2) forming a reaction mixture including: (i) the expressed chimeric protein; (ii) a substantially purified sortase-transamidase enzyme; and (iii) a Gram-positive bacterium having a peptidoglycan to which the sortase-transamidase can link the polypeptide through the sorting signal; (3) binding of the chimeric protein covalently to the cell wall by the enzymatic action of a sortase-transamidase expressed by the Gram-positive bacterium involving cleavage of the chimeric protein within the $LPX_3X_4G$ motif so that the polypeptide is displayed on the surface of the Gram-positive bacterium in such a way that the polypeptide is accessible to a ligand; and (4) reacting the displayed polypeptide with a labeled specific binding partner to screen the chimeric protein for reactivity with the labeled specific binding partner.

The nucleic acid segment encoding the chimeric protein is formed by methods well known in the art and can include a spacer.

In the last step, the cells are merely exposed to the labeled antibody or other labeled specific binding partner, unreacted antibodies removed as by a wash, and label associated with the cells detected by conventional techniques such as fluorescence, chemiluminescence, or autoradiography.

A second embodiment of this method employs expression in a Gram-positive bacterium that also produces a sortase-transamidase enzyme. This method comprises: (1) cloning a nucleic acid segment encoding a chimeric protein into a Gram-positive bacterium to generate a cloned chimeric protein including therein a carboxyl-terminal sorting signal as described above, the chimeric protein including the polypeptide whose expression is to be screened; (2) growing the bacterium into which the nucleic acid segment has been cloned to express the cloned chimeric protein to generate a chimeric protein including therein a carboxyl-terminal sorting signal; (3) binding the polypeptide covalently to the cell wall by the enzymatic action of a sortase-transamidase expressed by the Gram-positive bacterium involving cleavage of the chimeric protein within the $LPX_3X_4G$ motif so that the polypeptide is displayed on the surface of the Gram-positive bacterium in such a way that the polypeptide is accessible to a ligand; and (4) reacting the displayed polypeptide with a labeled specific binding partner to screen the chimeric protein for reactivity with the labeled specific binding partner.

V. Use of Sorted Molecules for Diagnosis and Treatment of Bacterial Infections

Sorted molecules can also be used for the diagnosis and treatment of bacterial infections caused by Gram-positive bacteria. Antibiotic molecules or fluorescent or any other diagnostic molecules can be chemically linked to a sorted peptide segment, which may include a spacer as described above, and then can be injected into animals or humans. These molecules are then sorted by the sortase-transamidase so that they are covalently linked to the cell wall of the bacteria.

In general, these methods comprise: (1) conjugating an antibiotic or a detection reagent to a protein including therein a carboxyl-terminal sorting signal to produce a conjugate; and (2) introducing the conjugate to an organism infected with a Gram-positive bacterium in order to cause the conjugate to be sorted and covalently cross-linked to the cell walls of the bacterium in order to treat or diagnose the infection.

The antibiotic used can be, but is not limited to, a penicillin, ampicillin, vancomycin, gentamicin, streptomycin, a cephalosporin, amikacin, kanamycin, neomycin, paromomycin, tobramycin, ciprofloxacin, clindamycin, rifampin, chloramphenicol, or norfloxacin, or a derivative of these antibiotics.

The detection reagent is typically an antibody or other specific binding partner labeled with a detectable label, such as a radiolabel. Such methods are well known in the art and need not be described further here.

Accordingly, another aspect of the present invention is a conjugate comprising an antibiotic or a detection reagent covalently conjugated to a protein including therein a carboxyl-terminal sorting signal as described above to produce a conjugate.

Yet another aspect of the present invention is a composition comprising the conjugate and a pharmaceutically acceptable carrier.

In this context, the conjugates can be administered using conventional modes of administration, including, but not limited to, intravenous, intraperitoneal, oral, or intralymphatic. Other routes of administration can alternatively be used. Oral or intraperitoneal administration is generally preferred. The composition can be administered in a variety of dosage forms, which include, but are not limited to, liquid solutions or suspensions, tablets, pills, powders, suppositories, polymeric microcapsules or microvesicles, liposomes, and injectable or infusible solutions. The preferred form depends on the mode of administration and the quantity administered.

The compositions for administration preferably also include conventional pharmaceutically acceptable carriers and adjuvants known in the art such as human serum albumin, ion exchangers, alumina, lecithin, buffered substances such as phosphate, glycine, sorbic acid, potassium sorbate, and salts or electrolytes such as protamine sulfate. The most effective mode of administration and dosage regimen for the conjugates as used in the methods in the present invention depend on the severity and course of the disease, the patient's health, the response to treatment, the particular strain of bacteria infecting the patient, other drugs being administered and the development of resistance to them, the accessibility of the site of infection to blood flow, pharmacokinetic considerations such as the condition of the patient's liver and/or kidneys that can affect the metabolism and/or excretion of the administered conjugates, and the judgment of the treating physician. According, the dosages should be titrated to the individual patient.

VI. Use of Sorted Polypeptides for Production of Vaccines

Additionally, the sorted polypeptides covalently crosslinked to the cell walls of Gram-positive bacteria according to the present invention have a number of uses. One use is use in the production of vaccines that can be used to generate immunity against infectious diseases affecting mammals, including both human and non-human mammals, such as cattle, sheep, and goats, as well as other animals such as poultry and fish. This invention is of special importance to mammals. The usefulness of these complexes for vaccine production lies in the fact that the proteins are on the surface of the cell wall and are accessible to the medium surrounding the bacterial cells, so that the antigenic part of the chimeric protein is accessible to the antigen processing system. It is well known that presenting antigens in particulate form greatly enhances the immune response. In effect, bacteria containing antigenic peptides on the surfaces linked to the bacteria by these covalent interactions function as natural adjuvants. Here follows a representative list of typical microorganisms that express polypeptide antigens against which useful antibodies can be prepared by the methods of the present invention:

(1) Fungi: *Candida albicans*, *Aspergillus fumigatus*, *Histoplasma capsulatum* (all cause disseminating disease), *Microsporum canis* (animal ringworm).

(2) Parasitic protozoa: (1) *Plasmodium falciparum* (malaria), *Trypanosoma cruzei* (sleeping sickness).

(3) Spirochetes: (1) *Borrelia bergdorferi* (Lyme disease), *Treponema pallidum* (syphilis), *Borrelia recufrentis* (relapsing fever), *Leptospira icterohaemorrhagiae* (leptospirosis).

(4) Bacteria: *Neisseria gonorrhoeae* (gonorrhea), *Staphylococcus aureus* (endocarditis), *Streptococcus pyogenes* (rheumatic fever), *Salmonella typhosa* (salmonellosis), *Hemophilus influenzae* (influenza), *Bordetella pertussis* (whooping cough), *Actinomyces israelii* (actinomycosis), *Streptococcus mutans* (dental caries), *Streptococcus equi* (strangles in horses), *Streptococcus agalactiae* (bovine mastitis), *Streptococcus anginosus* (canine genital infections).

(5) Viruses: Human immunodeficiency virus (HIV), poliovirus, influenza virus, rabies virus, herpes virus, foot and mouth disease virus, psittacosis virus, paramyxovirus, myxovirus, coronavirus.

Typically, the resulting immunological response occurs by both humoral and cell-mediated pathways. One possible immunological response is the production of antibodies, thereby providing protection against infection by the pathogen.

This method is not limited to protein antigens. As discussed below, non-protein antigens or haptens can be covalently linked to the C-terminal cell-wall targeting segment, which can be produced as an independently expressed polypeptide, either alone, or with a spacer at its amino-terminal end. If a spacer at the amino-terminal end is used, typically the spacer will have a conformation allowing the efficient interaction of the non-protein antigen or hapten with the immune system, most typically a random coil or α-helical form. The spacer can be of any suitable length; typically, it is in the range of about 5 to about 30 amino acids; most typically, about 10 to about 20 amino acids. In this version of the embodiment, the independently expressed polypeptide, once expressed, can then be covalently linked to the hapten or non-protein antigen. Typical non-protein antigens or haptens include drugs, including both drugs of abuse and therapeutic drugs, alkaloids, steroids, carbohydrates, aromatic compounds, including many pollutants, and other compounds that can be covalently linked to protein and against which an immune response can be raised.

Alternatively, a protein antigen can be covalently linked to the independently expressed cell-wall targeting segment or a cell-wall targeting segment including a spacer.

Many methods for covalent linkage of both protein and non-protein compounds to proteins are well known in the art and are described, for example, in P. Tijssen, "Practice and Theory of Enzyme Immunoassays" (Elsevier, Amsterdam, 1985), pp. 221–295, and in S. S. Wong, "Chemistry of Protein Conjugation and Cross-Linking" (CRC Press, Inc., Boca Raton, Fla., 1993).

Many reactive groups on both protein and non-protein compounds are available for conjugation.

For example, organic moieties containing carboxyl groups or that can be carboxylated can be conjugated to proteins via the mixed anhydride method, the carbodiimide method, using dicyclohexylcarbodiimide, and the N-hydroxysuccinimide ester method.

If the organic moiety contains amino groups or reducible nitro groups or can be substituted with such groups, conjugation can be achieved by one of several techniques. Aromatic amines can be converted to diazonium salts by the slow addition of nitrous acid and then reacted with proteins at a pH of about 9. If the organic moiety contains aliphatic amines, such groups can be conjugated to proteins by various methods, including carbodiimide, tolylene-2,4-diisocyanate, or malemide compounds, particularly the N-hydroxysuccinimide esters of malemide derivatives. An example of such a compound is 4-(N-maleimidomethyl)-cyclohexane-1-carboxylic acid. Another example is m-maleimidobenzoyl-N-hydroxysuccinimide ester. Still another reagent that can be used is N-succinimidyl-3-(2-pyridyidithio) propionate. Also, bifunctional esters, such as dimethylpimelimidate, dimethyladipimidate, or dimethylsuberimidate, can be used to couple amino-group-containing moieties to proteins.

Additionally, aliphatic amines can also be converted to aromatic amines by reaction with p-nitrobenzoylchloride and subsequent reduction to a p-aminobenzoylamide, which can then be coupled to proteins after diazotization.

Organic moieties containing hydroxyl groups can be cross-linked by a number of indirect procedures. For example, the conversion of an alcohol moiety to the half ester of succinic acid (hemisuccinate) introduces a carboxyl group available for conjugation. The bifunctional reagent sebacoyidichloride converts alcohol to acid chloride which, at pH 8.5, reacts readily with proteins. Hydroxyl-containing organic moieties can also be conjugated through the highly reactive chlorocarbonates, prepared with an equal molar amount of phosgene.

For organic moieties containing ketones or aldehydes, such carbonyl-containing groups can be derivatized into carboxyl groups through the formation of O-(carboxymethyl) oximes. Ketone groups can also be derivatized with p-hydrazinobenzoic acid to produce carboxyl groups that can be conjugated to the specific binding partner as described above. Organic moieties containing aldehyde groups can be directly conjugated through the formation of Schiff bases which are then stabilized by a reduction with sodium borohydride.

One particularly useful cross-linking agent for hydroxyl-containing organic moieties is a photosensitive noncleavable heterobifunctional cross-linking reagent, sulfosuccinimidyl 6-[4'-azido-2'-nitrophenylamino] hexanoate. Other similar reagents are described in S. S. Wong, "Chemistry of Protein Conjugation and Cross-Linking," supra.

Other cross-linking reagents can be used that introduce spacers between the organic moiety and the specific binding partner.

These methods need not be described further here.

VII. Production of Substantially Purified Sortase-Transamidase Enzyme

Another aspect of the present invention is methods for the production of substantially purified sortase-transamidase enzyme.

A. Methods Involving Expression of Cloned Gene

One method for the production of substantially purified sortase-transamidase enzyme involves the expression of the cloned gene, preferably the srtA gene or the srtB gene. The isolation of the nucleic acid segment or segments encoding a sortase-transamidase enzyme is described above; these nucleic acid segment or segments are then incorporated into a vector and then use to transform a host in which the enzyme can be expressed. In one alternative, the host is a Gram-positive bacterium.

The next step in this alternative is expression in a Gram-positive bacterium to generate the cloned sortase-transamidase enzyme. Expression is typically under the control of various control elements associated with the vector incorporating the DNA encoding the sortase-transamidase gene, such as the coding region of the srtA gene or the srtB gene; such elements can include promoters and operators, which can be regulated by proteins such as repressors. The conditions required for expression of cloned proteins in Gram-positive bacteria, particularly *S. aureus*, are well known in the art and need not be further recited here. An example is the induction of expression of lysostaphin under control of the BlaZRI regulon induced by the addition of methicillin.

When expressed in *Staphylococcus aureus*, the chimeric protein is typically first exported with an amino-terminal leader peptide, such as the hydrophobic signal peptide at the amino-terminal region of the cloned lysostaphin of Recsei et al. (P. Recsei et al., "Cloning, Sequence, and Expression of the Lysostaphin Gene from *Staphylococcus simulans*," Proc. Natl. Acad. Sci. USA 84:1127–1131 (1987)).

Alternatively, the cloned nucleic acid segment encoding the sortase-transamidase enzyme can be inserted in a vector that contains sequences allowing expression of a sortase-transamidase in another organism, such as *E. coli* or *S. typhimurium*. A suitable host organism can then be transformed or transfected with the vector containing the cloned nucleic acid segment. Expression is then performed in that host organism.

The expressed enzyme is then purified using standard techniques. Techniques for the purification of cloned proteins are well known in the art and need not be detailed further here. One particularly suitable method of purification is affinity chromatography employing an immobilized antibody to sortase. Other protein purification methods include chromatography on ion-exchange resins, gel electrophoresis, isoelectric focusing, and gel filtration, among others.

One particularly useful form of affinity chromatography for purification of cloned proteins, such as sortase-transamidase, as well as other proteins, such as glutathione S-transferase and thioredoxin, that have been extended with carboxyl-terminal histidine residues, is chromatography on a nickel-sepharose column. This allows the purification of a sortase-transamidase enzyme extended at its carboxyl terminus with a sufficient number of histidine residues to allow specific binding of the protein molecule to the nickel-sepharose column through the histidine residues. The bound protein is then eluted with imidazole. Typically, six or more histidine residues are added; preferably, six histidine residues are added. One way of adding the histidine residues to a cloned protein, such the sortase-transamidase, is through PCR with a primer that includes nucleotides encoding the histidine residues. The histidine codons are CAU and CAC expressed as RNA, which are CAT and CAC as DNA. Amplification of the cloned DNA with appropriate primers will add the histidine residues to yield a new nucleic acid segment, which can be recloned into an appropriate host for expression of the enzyme extended with the histidine residues.

B. Other Methods

Alternatively, the sortase-transamidase can be purified from Gram-positive bacteria by standard methods, including precipitation with reagents such as ammonium sulfate or protamine sulfate, ion-exchange chromatography, gel filtration chromatography, affinity chromatography, isoelectric focusing, and gel electrophoresis, as well as other methods known in the art.

Because the sortase-transamidase is a cysteine protease, one particularly useful method of purification involves covalent chromatography by thiol-disulfide interchange, using a two-protonic-state gel containing a 2-mercaptopyridine leaving group, such as Sepharose 2B-glutathione 2-pyridyl disulfide or Sepharose 6B-hydroxypropyl 2-pyridyl disulfide. Such covalent chromatographic techniques are described in K. Brocklehurst et al., "Cysteine Proteases," in New Comprehensive Biochemistry, Volume 16: Hydrolytic Enzymes (A. Neuberger & K. Brocklehurst, eds., Elsevier, New York, 1987), ch. 2, pp. 39–158.

VIII. Further Applications of Sortase-Transamidase

A. Production of Antibodies

Antibodies can be prepared to a substantially purified sortase-transamidase of the present invention, whether the sortase-transamidase is purified from bacteria or produced from recombinant bacteria as a result of gene cloning procedures. Because a substantially purified enzyme according to the present invention is a protein, it is an effective antigen, and antibodies can be made by well-understood methods such as those disclosed in E. Harlow & D. Lane, "Antibodies: A Laboratory Manual" (Cold Spring Harbor Laboratory, 1988). In general, antibody preparation involves immunizing an antibody-producing animal with the protein, with or without an adjuvant such as Freund's complete or incomplete adjuvant, and purification of the antibody produced. The resulting polyclonal antibody can be purified by techniques such as affinity chromatography.

Once the polyclonal antibodies are prepared, monoclonal antibodies can be prepared by standard procedures, such as those described in Chapter 6 of Harlow & Lane, supra.

B. Derivatives for Affinity Chromatography

Another aspect of the present invention is derivatives of a cloned, substantially purified sortase-transamidase of the present invention extended at its carboxyl terminus with a sufficient number of histidine residues to allow specific binding of the protein molecule to a nickel-sepharose column through the histidine residues. Typically, six or more histidine residues are added; preferably, six histidine residues are added.

The histidine residues can be added to the carboxyl terminus through PCR cloning as described above.

This invention is further described by means of the following examples. These Examples are for illustrative purposes only, and are not to be construed as limiting the scope of the invention in any manner.

EXAMPLE 1

Identification of a Staphylococcal Mutant Defective in Cell Wall Sorting

Generation of Temperture Sensitive (ts) Mutants Through Chemical Mutagenesis

Figure 2A:
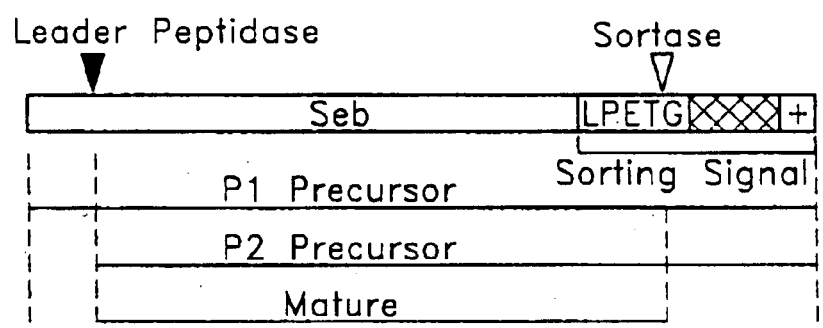
FIG. 2:
(A) is a diagramatic representation of the primary structure of the surface protein precursor SEB-SPA$_{490-524}$.
(B) depicts an SDS-PAGE gel of immunoprecipitated [$^{35}$S] SEB-SPA$_{490-52\ P1}$ precursor, P2 precursor and mature protein. SM317 and SM329 are two ts mutants that accumulate P2 as compared to wild-type staphylococci (WT).
(C) depicts an SDS-PAGE gel of immunoprecipitated [$^{35}$S] SEB-SPA$_{490-52\ P1}$ precursor, P2 precursor and mature protein in SM317, SM329 and WT staphylococci following a pulse-chase analysis of SEB-SPA$_{490-524}$ anchoring.
(D) depicts Staphylococcal strains OS2 (WT), SM317 and SM329 streaked on tryptic soy agar and grown at 42° C.

Cell wall sorting mutants were created and isolated from a population of conditional lethal mutants of $S.$ $aureus$ strain OS2. Staphylococci were mutagenized with nitrosoguanidine and colonies were formed by plating at 30° C. Bacteria were streaked and incubated at 30° C. and 42° C. to identify mutants that are temperature sensitive for growth (ts). A collection of one thousand ts mutants was transformed with pSEB-SPA$_{490-524}$ (O. Schneewind, D. Mihaylova-Petkov, P. Model, $EMBO$ 12, 4803 (1993)), specifying a reporter protein for measurements of surface protein anchoring. The SEB-SPA$_{490-524}$ precursor (P1) is exported from the cytoplasm and its $NH_2$-terminal leader peptide removed to generate the P2 intermediate (FIG. 2A). The P2 precursor is the substrate for sortase, which cleaves the polypeptide between the threonine and the glycine of the LPXTG motif and generates mature, anchored surface protein (M). When analyzed by labeling wild-type staphylococci with [$^{35}$S] methionine for 5 min, cleavage of P1 precursor is faster than that of the P2 species, yielding a ratio of P1 (5%), P2 (19%), and M(76%) concentration (FIG. 2B). This assay was employed to screen one thousand ts mutants and two strains were identified that accumulated P2 precursor at 47% (SM317) and 26% (SM329), respectively (FIG. 2B). To examine the sorting reaction further, mutant and wild-type staphylococci were subjected to pulse-chase analysis (FIG. 2C). $S.$ $aureus$ OS2 (wild-type) cleaved and anchored the P1 precursor within 2 min. The sorting reaction in strain SM317 was severely reduced as cleavage and cell wall anchoring of pulse-labeled P2 required more than 10 min. Strain SM329 displayed only a weak defect and P2 processing required 3 min (FIG. 2C). When examined by pulse-labeling staphylococci grown in minimal medium, SM329 displayed a much more severe defect in cell wall sorting.

Anchor Structure of Surface Proteins in the Mutant Strain SM317

To examine whether the mutant strains SM317 and SM329 are defective in the synthesis of bacterial cell wall, two tests were performed. Lysostaphin is a bacteriolytic enzyme that cuts the pentaglycine crossbridges of the staphylococcal cell wall predominantly at the central glycine residue (C. A. Schindler and V. T. Schuhardt, $Proc.$ $Natl.$ $Acad.$ $Sci.$ $USA$ 51, 414 (1964); B. L. M. de Jonge, Y. S. Chang, D. Gage, A. Tomasz, $J.$ $Biol.$ $Chem.$ 267, 11248 (1992)). As reported previously, fem mutants display resistance to this bacteriocin and grow even in the presence of large amounts of lysostaphin (U. Kopp, M. Roos, J. Wecke, H. Labischinski, $Microb.$ $Drug$ $Resist.$ 2, 29 (1996)). Strains SM317 and SM329 were sensitive to lysostaphin at concentrations that also inhibited growth of wild-type staphylococci, indicating that the sorting defect in SM317 is not caused by a mutationally altered cell wall crossbridge. To measure bacterial cell wall synthesis, staphylococci were grown in minimal medium and labeled with [$^3$H]lysine and [$^3$H]leucine (D. Boothby, L. Daneo-Moore, G. D. Shockman, $Anal.$ $Biochem.$ 44, 645 (1971)). As lysine, but not leucine, is a component of the bacterial cell wall, the ratio of [$^3$H]lysine/[$^3$H]leucine incorporation into acid precipitable and protease resistant murein polymer is a measure for cell wall synthesis (D. Boothby, L. Daneo-Moore, G. D. Shockman, $Anal.$ $Biochem.$ 44, 645 (1971)). Wild-type staphylococci displayed a ratio of 30, while the addition of vancomycin to the culture medium reduced the ratio of incorporated lysine/leucine to 1.5 (20 fold inhibition). Strains SM317 and SM329 displayed a ratio of 18 and 19

(1.6 fold less than wild-type cells), suggesting that the accumulation of P2 precursor in the mutant SM317 is not caused by a defect in cell wall synthesis.

Figure 3A:
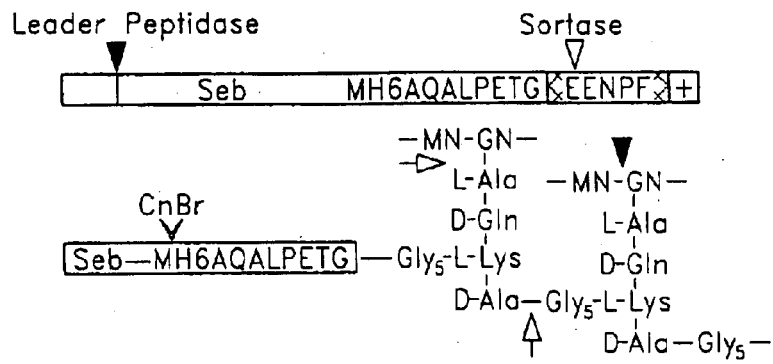
FIG. 3:
(A) is a diagrammatic representation of the primary structure of SEB-MH$_6$-CWS and its linkage to the cell wall.
(B) deptics a mass spectroscopy profile (MALDI-MS) of solubilized and affinity purified SEB-MH$_6$-CWS.
(C) deptics a mass spectroscopy profile (MALDI-MS) of solubilized, mutanolysin-released anchor peptides were digested with f11 hydrolase.
Figure 3B:
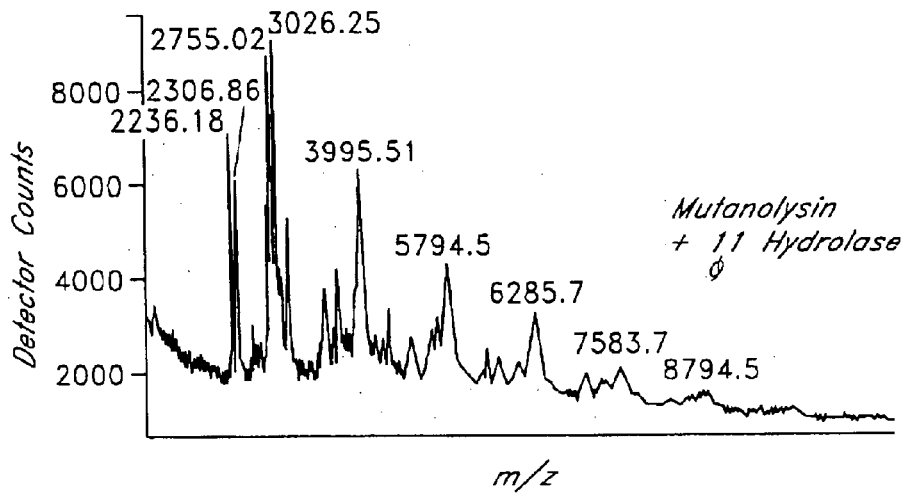
Figure 3C:
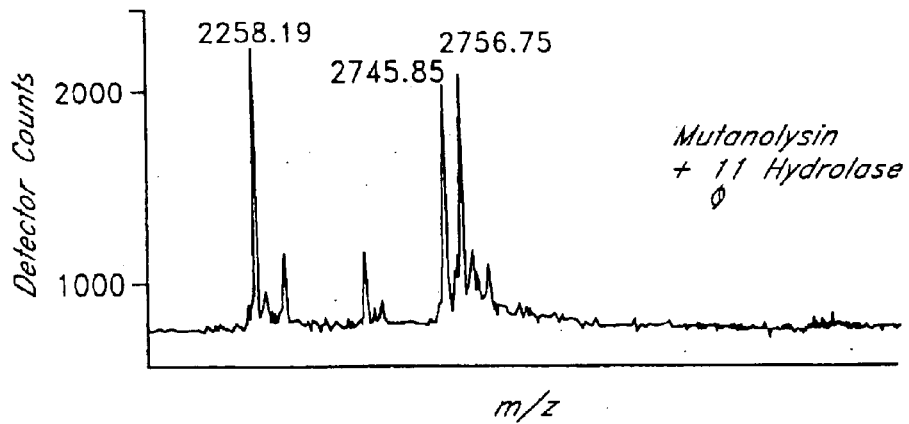

The cell wall anchor structure of surface protein in strain SM317 was determined (FIG. 3). Plasmid pHTT4 specifying the reporter protein SEB-MH$_6$-CWS was transformed into *S. aureus* SM317 (H. Ton-That, K. F. Faull, O. Schneewind, *J. Biol. Chem.* 272, 22285 (1997)). The staphylococcal cell wall was purified and digested with mutanolysin, a muramidase that hydrolyzes the glycan strands (K. Yokogawa, et al., *Antimicrob. Agents Chemother.* 6, 156 (1974)). Mutanolysin-released surface protein was purified by chromatography on Ni-NTA and cleaved at methionine residues with cyanogen bromide (H. Ton-That, K. F. Faull, O. Schneewind, *J. Biol. Chem.* 272, 22285 (1997)). COOH-terminal peptides bearing cell wall anchor structures were purified by a second affinity chromatography step and analyzed by MALDI-MS (FIG. 3B). A series of ion signals with regularly spaced mass increments was revealed, measurements that are consistent with one, two, three, four, five and six peptidoglycan subunits linked to the COOH-terminal threonine of surface protein. Ion signals of muanolysin-solubilized anchor peptides were explained as H$_6$AQALPET-Gly$_5$ linked to cell wall tetrapeptide (predicted mass 2235; observed 2236), pentapeptide (predicted mass 2306; observed 2306), N,O6-diacetylMurNac-GlcNac tetrapeptide (predicted mass 2755, observed 2756), N,O6-diacetylMurNac-GlcNac pentapeptide (predicted mass 2826, observed 2826), murein-tetrapeptide-murein-pentapeptide (predicted mass 3991, observed 3995), (murein-tetrapeptide)$_2$-murein-pentapeptide (predicted mass 5194; observed 5196), (murein-tetrapeptide)$_4$ (predicted mass 6285 observed 6285), (murein-tetrapeptide)$_4$-murein-pentapeptide (predicted mass 7581; observed 7583), (murein-tetrapeptide)$_5$-murein-pentapeptide (predicted mass 8783; observed 8784). If surface protein is tethered to cross-linked peptidoglycan of strain SM317, digestion of muramidase-solubilized anchor peptides with f11 hydrolase should produce anchor peptide linked to murein tetrapeptide and disaccharide-tetrapeptide (H. Ton-That, K. F. Faull, O. Schneewind, *J. Biol. Chem.* 272, 22285 (1997); W. W. Navarre, H. Ton-That, K. F. Faull, O. Schneewind, *J. Biol. Chem.* 274, in press (1999)) (FIG. 3). This was tested and the doubly digested anchor peptides generated ion signals at m/z 2236 [L-Ala-D-iGln-L-Lys(NH$_2$—H$_6$AQALPET-Gly$_5$)-D-Ala, predicted mass 2235], 2714 [MurNac(L-Ala-D-iGln-L-Lys(NH$_2$—H$_6$AQALPET-Gly$_5$)-D-Ala)-GlcNac, predicted mass 2713] and 2756 [O6-acetyl-MurNac(L-Ala-D-iGln-L-Lys(NH$_2$—H$_6$AQALPET-Gly$_5$)-D-Ala)-GlcNac, predicted mass 2756] (FIG. 3C). Thus, surface proteins of *S. aureus* SM317 are tethered to cross-linked peptidoglycan in a manner that is indistinguishable from the anchor structure of polypeptides in wild-type staphylococci (W. W. Navarre, H. Ton-That, K. F. Faull, O. Schneewind, *J. Biol. Chem.* 273, 29135 (1998)). These results suggest that the accumulation of P2 precursor in strain SM317 is likely caused by a defect in sortase.

Screening for the Sortase Gene

Figure 4A:
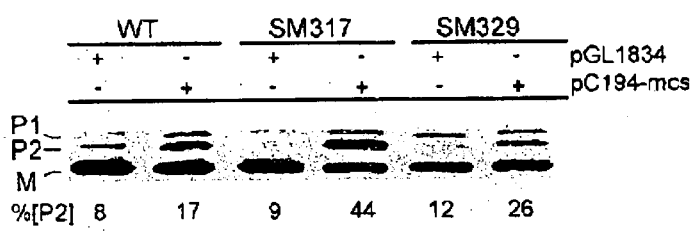
FIG. 4:
(A) depicts an SDS-PAGE gel of immunoprecipitated [$^{35}$S] SEB-SPA$_{490-52\ P1}$ precursor, P2 precursor and mature protein in SM317, SM329 and WT staphylococci transformed with or without pGL1834 (plasmid containing the srtA gene cloned into pC194-mcs) following a pulse-chase analysis of SEB-SPA$_{490-524}$ anchoring.
(B) depicts an SDS-PAGE gel of immunoprecipitated [$^{35}$S] SEB-SPA$_{490-52\ P1}$ precursor, P2 precursor and mature protein from SM317 transformed with the DNA of either the mutant SM317 (pGL1898) or wild-type strain OS2 (pGL1897).
(C) depicts an SDS-PAGE gel of immunoprecipitated [35S] SEB-SPA490-52 P1 precursor, P2 precursor and mature protein from *S. aureus* OS2 (wild type), SM317 and SM329 transformed with pGL1834 and subjected to pulse-chase analysis.
Figure 4B:
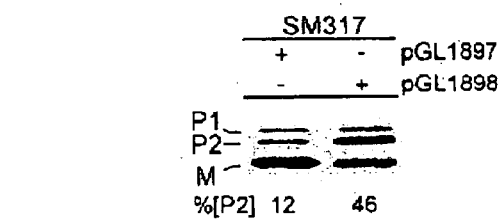
Figure 4C:
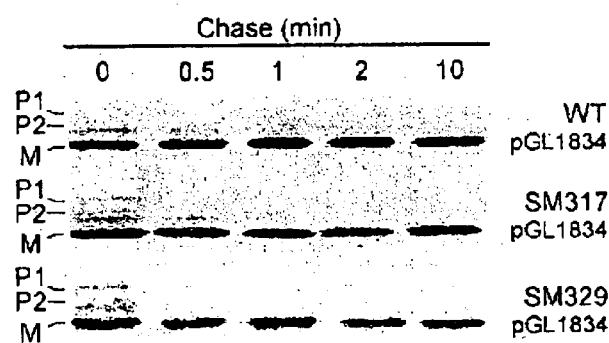
Figure 5:
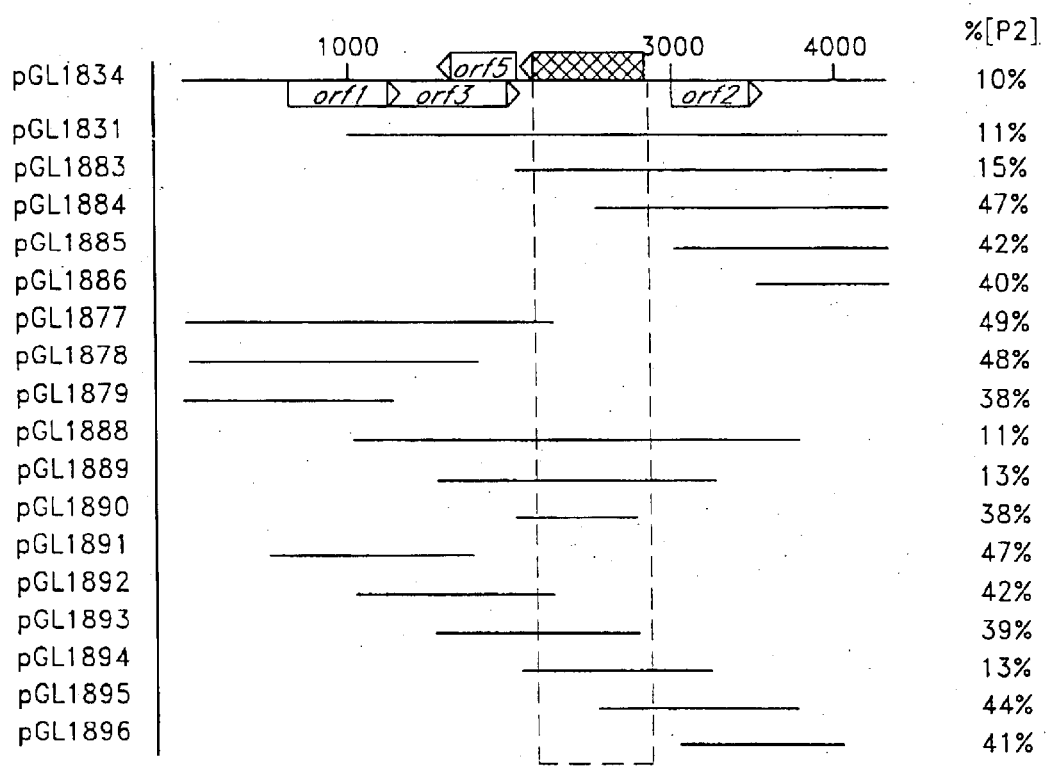
FIG. 5 depicts the size of DNA fragments and the position of the coding region of the srtA gene of *S. aureus* (SEQ ID NO:2) sufficient for an increase in surface protein anchoring. The concentration of P2 precursor in plasmid transformants of the mutant SM317 was measured by labeling with [$^{35}$S] methionine and is indicated in percent.

Over-expression of sortase from a multi-copy plasmid should reduce the concentration of P2 in both wild-type and mutant staphylococci. A plasmid library of two thousand 3–5 kb random *S. aureus* OS2 chromosomal DNA insertions was screened for sequences that caused a reduction in the concentration of P2 precursor in strain SM317. Two plasmids, pGL1631 and pGL1834, answered this screen (FIG. 4). Transformation with pGL1834 reduced the P2 concentration in strain SM317 from 44% to 9%, in strain SM329 from 26% to 12%, and in wild-type *S. aureus* OS2 from 17% to 8%. When measured by pulse-chase analysis, *S. aureus* OS2 (pGL1834) displayed a rapidly increased processing of P2 precursors, a phenotype that was also observed in strains SM317 and SM329 (FIG. 4C). DNA sequencing revealed that pGL1631 and pGL1834 contained staphylococcal chromosomal DNA insertions with identical overlapping sequences. The DNA sequence sufficient to promote a reduction in P2 concentration was mapped to a gene which was named srtA (surface protein sorting A) (FIG. 5).

The srtA Gene

The srtA gene (SEQ. ID NO.2) specifies a polypeptide chain of 206 amino acids (FIG. 6; SEQ. ID. NO. 3). A sequence of 18 hydrophobic amino acids near the NH$_2$-terminus suggests the presence of a signal peptide/membrane anchor sequence. This feature is consistent with the notion that cell wall anchoring occurs on the cell surface, after polypeptide substrates bearing an LPXTG motif have been translocated across the cytoplasmic membrane. Another property of the srtA gene consistent with its function as sortase is the presence of codon 184 specifying cysteine. As the cell wall sorting reaction is sensitive to methanethiosulfonate, a reagent that forms disulfide with sulfhydryl (D. J. Smith, E. T. Maggio, G. L. Kenyon, *Biochemistry* 14, 764 (1975)), the presence of a cysteine must be a conserved feature of sortase homologues.

Many, if not all, Gram-positive pathogens display proteins on their surface via a sorting signal mediated mechanism (W. W. Navarre and O. Schneewind, *Microbiol. Mol. Biol. Rev.* 63, 174 (1999)). Thus, if the srtA gene specifies sortase, homologous genes should be found in the genomes of other Gram-positive pathogens. Chromosomal DNA sequences of *Enterococcus faecalis*, *Staphylococcus aureus*, *Streptococcus pyogenes*, *Streptococcus pneumoniae*, and *Streptococcus mutans* were searched and the presence of srtA genes revealed (FIG. 7). Database searches also identified sequences homologous to srtA in *Bacillus subtilis* and *Actinomyces naeslundii*. All srtA homologues displayed absolute conservation of the cysteine and striking conservation of the peptide sequences surrounding it (FIG. 7). *S. pneumoniae* harbors more than one srtA homologue which we have named srtB and srtC, respectively. The srtA like genes of *E. faecalis* and *A. naeslundii* are immediately adjacent to structural genes specifying surface proteins with a COOH-terminal sorting signal. The presence of a srtA homologue in the chromosome of *B. subtilis* is surprising as LPXTG motif containing sorting signals have not yet been identified in this organism. One of the srtA homologues in *A. naeslundii*, previously designated orf365, has been mutated, which abolished fimbrial assembly of mutant Actinomyces (M. K. Yeung, J. A. Donkersloot, J. O. Cisar, P. A. Ragsdale, *J. Bacteriol.* 66, 1482 (1998)). Actinomyces fimbriae are composed of protein subunits bearing LPXTG motifs (M. K. Yeung and J. O. Cisar, *J. Bacteriol.* 172, 2462 (1990)), however the mechanism of fimbrial assembly (polymerization) is not yet understood.

The srtA Gene in Strain SM317

To examine whether the defect in cell wall sorting of *S. aureus* SM317 is caused by a mutation in the srtA gene, corresponding sequences were PCR amplified from the chromosomal DNA of *S. aureus* OS2 and SM317. When cloned into a multi-copy vector and transformed into *S. aureus* SM317, the srtA gene amplified from wild-type staphylococci reduced the P2 concentration from 44% to 12%, while the same gene amplified from the chromosomal DNA of *S. aureus* SM317 did not reduce the P2 concentration of the parent strain (FIG. 4B). Thus, the srtA gene is defective in strain SM317 and DNA sequencing identified mutations in codons 35 and 180. The expression of wild-type srtA in SM317 in the ts phenotype of the mutant strain was examined. Multi-copy expression of srtA (pGL1894)

allowed growth of SM317 at 42° C. albeit at a rate that was less than that observed for wild-type staphylococci. This result suggests that the conditional lethal phenotype of *S. aureus* SM317 is not only caused a mutation in the srtA gene. Expression of plasmid encoded wild-type srtA did not alter the ts growth phenotype of *S. aureus* SM329.

Sortase and the Cell Wall Sorting Reaction

The srtA gene was isolated as a multi-copy suppressor of P2 precursor accumulation, a scheme that should only be answered by the gene for sortase. Only one gene (srtA) from a library of two thousand plasmid transformants bearing random 3–5 kb chromosomal DNA insertions was observed this screen. Additional observations show SrtA protein catalyzes the in vitro transpeptidation of substrates bearing an LPXTG motif, thereby demonstrating that SrtA displays sortase activity. Purified SrtA protein can be used for the screening of compounds that inhibit sortase. Such compounds may be useful for the treatment of human infections caused by Gram-positive bacteria.

Materials and Methods

Mutagenesis of *S. aureus* Strain OS2

Staphylococci ($1 \times 10^{12}$ cfu) were treated with 0.2 mg/ml N-methyl-N'-nitro-N-nitrosoguanidine for 45 min at 30° C. and mutagenesis was quenched by the addition of 2 volumes of 100 mM sodium phosphate, pH 7.0. Approximately 80% of the mutagenized population was killed and the mutational frequency of rifampicin resistant rpoB mutations was increased to $1.2 \times 10^{-4}$. Temperature sensitive mutants were selected by growing the mutagenized population in tryptic soy broth at 42° C. and treating with 8 μg/ml penicillin G for two hours, a selection that was repeated twice. Colonies were formed at 30° C., streaked on tryptic soy agar and examined for growth at 42° C.

Transformation of Competent Cells

Staphylococci were grown in tryptic soy broth supplemented with chloramphenicol (10 mg/ml) or tetracycline (2 mg/ml) at 30° C. until $OD_{660}$ 0.6. Cells were incubated at 42° C. for 20 min, sedimented by centrifugation at 15,000× g for 3 minutes and washed with 1 ml of prewarmed minimal medium [Schneewind, O., Model, P., Fischetti, V. A. (1992) *Cell* 70, 267]. Staphylococci were labeled with 50 mCi of [$^{35}$S]-Promix (Amersham) for 5 minutes and surface protein processing quenched by the addition of 75 ml 100% TCA. The TCA precipitates were collected by centrifugation, washed in acetone and dried under vacuum. Samples were suspended in 1 ml of 0.5 M Tris-HCl, pH 7.0 and staphylococcal peptidoglycan was digested by adding 50 ml 2 mg/ml lysostaphin (AMBI Pharmaceuticals) for 1 hour at 37° C. Proteins were again precipitated with TCA, washed with acetone and, after immunoprecipitation with a-SEB, were analyzed by 14% SDS-PAGE and PhosphorImager.

Pulse-Chase Screen of Mutants

Staphylococci were grown as described above and 5 ml were labeled with 500 mCi of [$^{35}$S]-Promix (Amersham) for 45 seconds. Incorporation of radioactivity was quenched by adding 50 ml chase (100 mg/ml casamino acids, 20 mg/ml methionine and cysteine). At timed intervals after the addition of the chase, 1 ml aliquots were removed and protein was precipitated by the addition of 75 ml 100% TCA. Sample preparation followed the same steps as described above.

DNA Sequencing

The DNA insertions pf pGL1631 and 1834 were mapped and sequenced by synthesizing oligonucleotide primers that annealed to sequenced template DNA 500 nucleotides apart. The primers for the amplification of srtA from the chromosomal DNA of *S. aureus* strains OS2 and SM317 were 5'-AAAAA-3' and 5'-TTTTT-3'.

EXAMPLE 2

Inhibitors of Cell Wall Sorting

To study the effects of antibiotic cell wall synthesis inhibitors interfered with the anchoring of surface proteins, the activity of several inhibitors were examined in a Gram-positive bacteria sorting assay. A search for chemical inhibitors of the sorting reaction identified methanethiosulfonates and p-hydroxymercuribenzoic acid. Thus, sortase, the enzyme proposed to cleave surface proteins at the LPXTG motif, appears to be a sulfhydryl containing enzyme that utilizes peptidoglycan precursors but not assembled cell wall as a substrate for the anchoring of surface protein.

Figure 8A:
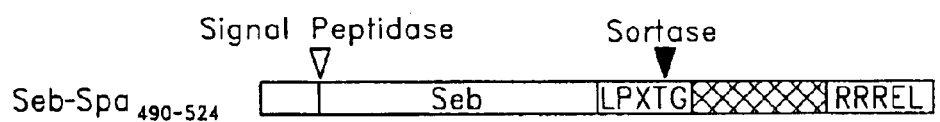
FIG. 8:
(A) depicts the structure of Seb-Spa$_{490-524}$ harboring an NH$_2$-terminal leader (signal) peptide with signal peptidase cleavage site as well as a COOH-terminally fused cell wall sorting signal consisting of the LPXTG motif, hydrophobic domain (black box), and positively charged tail (boxed +).
(B) depicts the SDS-PAGE gel analysis of pulse chase experiment where staphlococcal cultures were labeled with [$^{35}$S]methionine for 1 min and quenching all further incorporation by the addition of excess unlabeled methionine (chase). P1 precursor, P2 precursor and mature Seb-Spa$_{490-524}$ were evaluated.
Figure 8B:
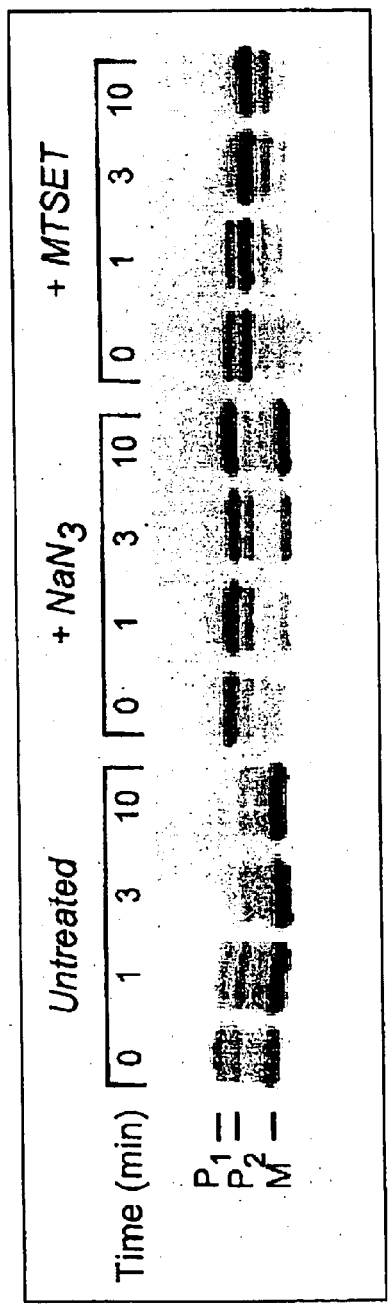

In order to identify compounds that interfere with the anchoring of surface proteins a reporter protein Seb-Spa$_{490-524}$ which, when expressed in *S. aureus* OS2 cells, is synthesized as a precursor in the cytoplasm and initiated into the secretory pathway by an NH$_2$-terminal leader peptide (P1 precursor) was utilized (Schneewind, O., Mihaylova-Petkov, D. and Model, P. (1993) *EMBO* 12, 4803–4811). After signal peptide cleavage, the P2 precursor bearing a COOH-terminal sorting signal serves as a substrate for sortase, an enzyme that cleaves between the threonine and the glycine of the LPXTG motif (Navarre, W. W. and Schneewind, O. (1994) *Mol. Microbiol.* 14,115–121). Amide linkage of the carboxyl of threonine to the cell wall crossbridge generates mature, anchored surface protein (M) (Schneewind, O., Fowler, A. and Faull, K. F. (1995) *Science* 268, 103–106). Surface protein processing was investigated by pulse-labeling polypeptides with [$^{35}$S]methionine. During the pulse, all three species, P1 and P2 precursors as well as mature Seb-Spa$_{490-524}$ can be detected (FIG. 8B). Within 1 min after the addition of the chase, most pulse-labeled surface protein was converted to the mature, anchored species. Surface protein anchoring was complete 3 min after the quenching of [$^{35}$S]methionine incorporation.

Sodium azide is an inhibitor of SecA, an essential component of the secretory pathway in bacteria (Oliver, D. B., Cabelli, R. J., Dolan, K. M. and Jarosik, G. P. (1990) *Proc. Natl. Acad. Sci. USA* 87, 8227–8231). Addition of 5 mM sodium azide to staphylococcal cultures 5 min prior to pulse-labeling significantly reduced protein export and led to the accumulation of leader peptide bearing P1 precursor (Schneewind, O., Model, P. and Fischetti, V. A. (1992) *Cell* 70, 267–281). Methanethiosulfonates react with sulfhydryl (Akabas, M. H. and Karlin, A. (1995) *Biochemistry* 34, 12496–12500) and one of these compounds, [2-(trimethylammonium) ethyl]methanethiosulfonate) (MTSET) prevented incorporation of [$^{35}$S]methionine by staphylococci. However, when added 15 seconds after the beginning of the pulse, MTSET interfered with the cleavage of sorting signals at the LPXTG motif, while the Sec-dependent export of P1 precursor remained unaltered. This result revealed that sortase must harbor a sulfhydryl that is necessary for enzymatic cleavage at LPXTG bearing sorting signals.

Sortase's requirement of sulfhydryl for enzymatic activity was tested by the addition of other sulfhydryl reagents and analysis of inhibition of the cleavage of sorting signals at the LPXTG motif. MTSES, another methanethiosulfonate, also interfered with sorting albeit not as effectively as MTSET (Table I). pHMB, an organic mercurial known to inhibit cysteine proteases, also displayed an inhibitory effect, whereas alkylating reagents such as N-ethylmaleimide, iodoacetate and iodoacetamide did not (Creighton, T. E. (1993) *Proteins*. W. H. Freeman and Company, New York). Sulfhydryl reducing agents, i.e. dithiothreitol and mercaptoethanol, did not affect the sorting reaction. Neither PMSF, which reacts with hydroxyl (Creighton, T. E. (1993) *Proteins*. W. H. Freeman and Company, New York), nor treatment with the divalent cation chelator EDTA interfered with cell wall sorting, indicating that sortase likely does not require divalent cations or hydroxyl for cleavage and anchoring of surface protein.

Antibiotic Inhibition of Bacterial Cell Wall Synthesis and Cell Wall Sorting

Figure 9B:
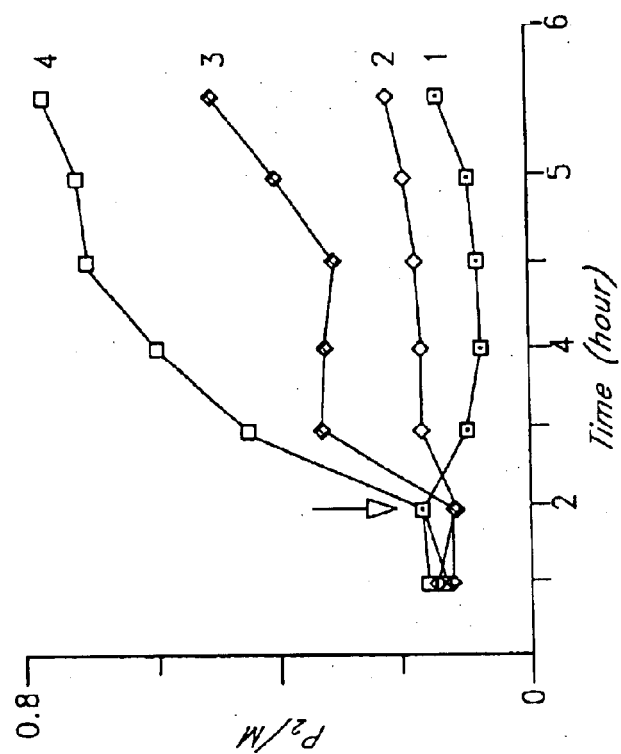
FIG. 9:
(A) depicts a growth curve for staphylococcal growth with antibiotics added (1, open squares: mock treated; 2, open diamonds: penicillin 10 µg/ml; 3, closed diamonds: moenomycin, 10 µg/ml; 4, closed squares: vancomycin 10 µg/ml).
(B) depicts a curve measuring the rate of cell wall sorting in the presence of antibiotics or mock treated as described in (A).
Figure 9A:
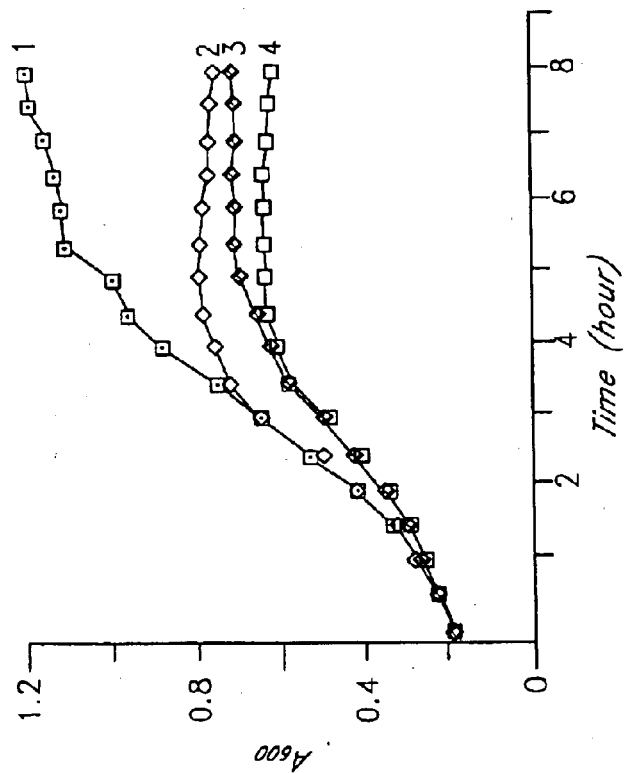

To examine the effect of known antibiotics on cell wall sorting three compounds, penicillin, vancomycin and moenomycin were used. $S.$ $aureus$ OS2 (pSeb-Spa$_{490-524}$) was grown in minimal medium until A$_{600}$ of 0.3, treated with 10 µg/ml of either penicillin, vancomycin, or moenomycin and incubated for an additional 5 hours (FIG. 9A). At 30 min intervals during this experiment, aliquots were withdrawn for measurements of surface protein sorting and cell wall synthesis. The effect of antibiotics on the rate of bacterial cell wall synthesis was determined as the ratio of [$^3$H]lysine/ [$^3$H]leucine label incorporated into acid precipitable, pronase resistant peptidoglycan. Lysine is a component of peptidoglycan, whereas leucine is not. Hence, the ratio of incorporation of these two amino acids is a measure for cell wall synthesis. Surface protein anchoring was measured by pulse-labeling and quantified as the ratio between the concentration of P2 precursor [P2] and mature, anchored Seb-Spa$_{490-524}$ [M].

Addition of vancomycin, penicillin or moenomycin reduced the growth rate of staphylococci as compared to a mock treated control. While the rate of cell wall sorting precursor cleavage remained constant during the growth of mock treated staphylococci, the addition of vancomycin led to a steady accumulation of P2 precursor, indicating that this compound caused a reduction of the sorting reaction. A similar, albeit weaker effect was observed when moenomycin was added to staphylococcal cultures. In contrast, penicillin G did not alter the rate of cell wall sorting. As expected, all three antibiotics diminished the rate of peptidoglycan synthesis (Table II). Together these data revaled that vancomycin and moenomycin cause a reduction in the rate of cell wall sorting, while penicillin had no effect on surface protein anchoring.

Cell Wall Sorting in Staphylococcal Protoplasts

Figures 10A, 10B:
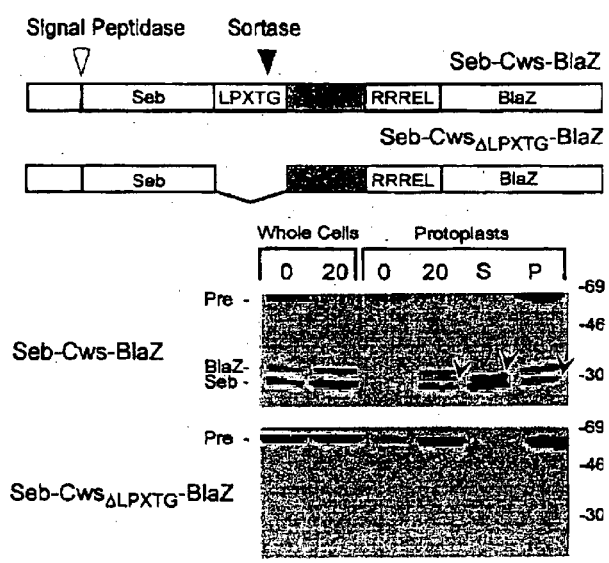
FIG. 10:
(A) depicts the structure of Seb-Cws-BlaZ harboring an NH$_2$-terminal signal (leader) peptide and the sorting signal of protein A which consists of an LPXTG motif, hydrophobic (shaded box) and charged domains (boxed RRREL). The sorting signal is fused to the COOH-terminus of Seb and to the NH$_2$-terminus of mature BlaZ. Cleavage at the LPXTG motif produces two fragments, an NH$_2$-terminal cell wall anchored surface protein (Seb) and a COOH-terminal BlaZ domain that is located in the bacterial cytoplasm.
(B) depicts an SDS-PAGE gel analysis of *S. aureus* OS2 (pSeb-Cws-BlaZ) and *S. aureus* OS2 (pSeb-Cws$_{DLPXTG}$-BlaZ) cell wall sorting. The arrows point to Seb species that were observed in protoplasts but not in whole cells.
Figure 11:
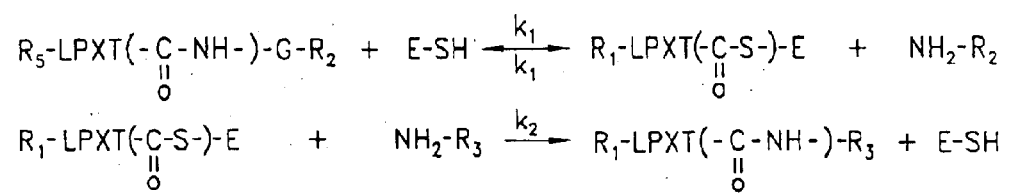
FIG. 11 depicts a model for the transpeptidation reaction catalyzed by staphylococcal sortase.

Previous work revealed that protoplasts, generated by muralytic digestion of staphylococci or penicillin selection of streptococcal L forms, secreted surface protein into the surrounding medium (van de Rijn, I. and Fischetti, V. A. (1981) $Infect. Immun.$ 32, 86–91; Movitz, J. (1976) $Eur. J. Biochem.$ 68, 291–299). This can be explained in two ways. Either the C-terminal sorting signals cannot retain surface proteins in the envelope of protoplasts or the presence of intact, assembled cell wall is not required to cleave sorting signals at their LPXTG motif. To distinguish between these possibilities, the surface protein anchoring in intact bacteria and staphylococcal protoplasts was measured (FIG. 10). Wild-type staphylococci cleaved the Seb-Cws-BlaZ precursor to generate the mature, anchored NH$_2$-terminal Seb and COOH-terminal, cytoplasmic BlaZ fragments (Navarre, W. W. and Schneewind, O. (1994) $Mol. Microbiol.$ 14, 115–121). When tested in staphylococcal protoplasts generated by lysostaphin-digestion of the cell wall, precursor cleavage occurred similar to whole cells, indicating that the presence of mature, assembled cell wall is not required for cleavage of sorting signals. Unique sorting products in protoplasts that migrated more slowly than rmature, anchored Seb (see arrow in FIG. 10B) were observed. As these species were immunoprecipitated with a-Seb but not with a-BlaZ, they likely represent products of the sorting reaction. The COOH-terminal anchor structure of these protoplast species are distinct from those generated by lysostaphin-digestion (three glycyl attached to the carboxyl of threonine), as they migrated more slowly on SDS-PAGE than lysostaphin-released Seb.

To examine whether all cleaved Seb fragments were released into the extra-cellular medium, pulse-labeled protoplasts were sedimented by centrifugation and separated from the extra-cellular medium in the supernatant. All Seb-Cws-BlaZ precursor and COOH-terminal BlaZ cleavage fragment sedimented with the protoplasts. In contrast, NH$_2$-terminal Seb fragments that migrated at the same speed as Seb released by lysostaphin-digestion from the cell wall of intact staphylococci were soluble in the culture medium. Some, but not all, of the more slowly migrating Seb species sedimented into the pellet, suggesting that these products of the sorting reaction may be attached to protoplast membranes. No precursor cleavage was observed for Seb-Cws$_{DLPXTG}$-BlaZ in either whole cells or staphylococcal protoplasts.

Materials and Methods

Bacterial Strains and Plasmids

Plasmids pSeb-Spa$_{490-524}$(3), pSeb-Csw-BlaZ, and pSeb-Cws$_{DLPXTG}$-BlaZ (Navarre, W. W. and Schneewind, O. (1994) $Mol. Microbiol.$ 14, 115–121) were transformed into $S.$ $aureus$ OS2 (spa:ermC, r) (Schneewind, O., Model, P. and Fischetti, V. A. (1992) $Cell$ 70, 267–281) and have been described previously. Staphylococci were generally grown in tryptic soy broth or agar. All chemicals were purchased from Sigma unless indicated otherwise.

Characterization of Cell Wall Sorting Intermediates $S.$ $aureus$ OS2 (pSeb-Spa$_{490-524}$) was grown overnight in CDM (van de Rijn, I. and Kessler, R. E. (1980) $Infect Immun.$ 27, 444–448) (Jeol BioSciences) supplemented with chloramphenicol (10 mg/ml), diluted 1:10 into minimal medium and grown with shaking at 37° C. until A$_{600}$ 0.6. Cells were labeled with 100 mCi of [$^{35}$S]-Promix (Amersham) for 1 minute. Labeling was quenched by the addition of an excess non-radioactive amino acid [50 ml chase (100 mg/ml casamino acids, 20 mg/ml methionine and cysteine)]. At timed intervals after the addition of the chase, 0, 1, 3, and 10 minutes, 250 ml aliquots were removed and protein was precipitated by the addition of 250 ml 10% TCA. The precipitate was sedimented by centrifugation 15,000× g for 10 min, washed with 1 ml acetone and dried. Samples were suspended in 1 ml of 0.5 M Tris-HCl, pH 6.8 and staphylococcal peptidoglycan was digested by adding 50 ml lysostaphin (Schindler, C. A. and Schuhardt, V. T. (1964) $Proc. Natl. Acad Sci. USA$ 51, 414–421) (100 mg, AMB1 Pharmaceuticals) and incubating for 1 hour at 37° C. Proteins were again precipitated with TCA, washed with acetone and subjected to immunoprecipitation with a-Seb followed by SDS-PAGE and PhosphorImager analysis. To characterize the P1 and P2 precursors, 1 ml of culture was either incubated with 5 mM sodium azide for 5 min prior to labeling or 5 mM MTSET was added 15 seconds after the beginning of the pulse.

Antibiotic Inhibition of Cell Wall Sorting

Overnight cultures of $S.$ $aureus$ OS2 (pSeb-Spa$_{490-524}$) grown in CDM were diluted into fresh minimal medium and incubated for until A$_{600}$ 0.3. Cultures were then treated with either penicillin (10 mg/ml), vancomycin (10 mg/ml), moenomycin (10 mg/ml) or left untreated. A 0.5 ml culture sample was removed for pulse labeling with 100 mCi of ($^{35}$S)-Promix (Amersham) for 5 minutes. Labeling was quenched and proteins precipitated by the addition of 0.5 ml 10% TCA. The precipitate was collected by centrifugation, washed in acetone and dried under vacuum. The pellets were suspended in 1 ml 0.5 M Tris-HCl, pH 7.0, 50 ml lysostaphin (100 mg/ml, AMB1 Pharmaceuticals) added and the staphylococcal cell wall digested by incubating for 1 hour at 37° C. Proteins were precipitated with TCA, washed in acetone, dried and solubilized in 50 ml 0.5 M Tris-HCl, pH 7.5, 4% SDS and boiled for 10 min. Aliquots of solubilized surface protein were immunoprecipitated with a-Seb followed by SDS-PAGE and PhosphorImager analysis.

Peptidoglycan Synthesis Measurements

Staphylococci were grown in the presence or absence of antibiotics as described above. At 30 min intervals, 0.5 ml culture samples were withdrawn and labeled with either 50 mCi [$^3$H]lysine or 50 mCi [$^3$H]leucine for 20 min (Boothby, D., Daneo-Moore, L. and Shockman, G. D. (1971) Anal. Biochem. 44, 645–653). All labeling was quenched by the addition of 0.5 ml 20% TCA. Samples were heated to 96° C. for 30 min, cooled to room temperature and pipetted onto glass fiber filters. The filters were placed into a holder and washed under vacuum suction with 25 ml 75% ethanol and 2 ml 50 mM Tris-HCl, pH 7.8. After incubation in 5 ml pronase solution (50 mM Tris-HCl, pH 7.8, 1 mg/ml pronase) at 30° C. for 30 min, filters were washed again with 4 ml of distilled water and 4 ml ethanol. The amount of radioactivity retained by the filter was determined by scintillation counting (Boothby, D., Daneo-Moore, L. and Shockman, G. D. (1971) Anal. Biochem. 44, 645–653).

Chemical Inhibitors of the Sorting Reaction

S. aureus OS2 (pSeb-Spa$_{490-524}$) was grown overnight in CDM supplemented with chloramphenicol (10 mg/ml), diluted 1:10 into minimal medium and grown with shaking at 37° C. until A$_{600}$ 0.6. Cells were labeled with 100 mCi of [$^{35}$S]-Promix (Amersham) for 5 minutes. Chemicals were added to a final concentration of 5 mM 15 seconds after the beginning of the pulse. All labeling was quenched by adding TCA to 10%. Precipitated cells and proteins were collected by centrifugation, washed in acetone and and the staphylococcal cell wall digested with lysostaphin as described above. The digests were again precipitated with TCA, immunoprecipitated with a-Seb followed by SDS-PAGE and PhosphorImager analysis.

Cell Wall Sorting in Staphylococcal Protoplasts

Overnight cultures of S. aureus OS2 (pSeb-Cws-BlaZ) or S. aureus OS2 (pSeb-Cws$_{DLPXTG}$-BlaZ) grown in CDM were diluted 1:10 into minimal medium and grown with shaking at 37° C. until A$_{600}$ 0.6. One ml of culture was pulse-labeled with 100 mCi of [$^{35}$S]-Promix (Amersham) for 2 minutes and labeling was quenched by the addition of 50 ml chase solution. Culture aliquots (0.5 ml) were removed for TCA precipitation either during the pulse or 20 min after the addition of chase. Another culture aliquot was first converted to protoplasts and then subjected to labeling. The cells were sedimented by centrifugation at 15,000× g for 5 min and suspended in 1 ml 50 mM Tris-HCl, 0.4 M sucrose, 10 mM MgCl2, pH 7.5. The cell wall was digested with lysostaphin (100 mg) for 30 min at 37° C. The protoplasts were labeled with 100 mCi of [$^{35}$S]-Promix (Amersham) for 2 minutes and labeling quenched by the addition of 50 ml chase solution. For sedimentation analysis, pulse-labeled staphylococci were centrifuged at 15,000× g for 10 min to separate soluble surface protein from those that were bound to protoplasts. All samples were precipitated with TCA, washed in acetone and suspended in 50 ml 4% SDS, 0.5 M Tris-HCl pH 7.5 with boiling for 10 min. Aliquots of solubilized surface protein precursor and anchored products were immunoprecipitated with a-Seb and a-BlaZ, subjected to SDS-PAGE and PhosphorImager analysis.

EXAMPLE 3

Purification and Characterization of Sortase-Transpeptidase

To examine whether staphylococcal sortase captures surface proteins after their cleavage at the LPXTG motif as acyl-enzyme intermediates, the proposed acyl-enzyme intermediates between surface protein and sortase were treated by hydroxylaminolysis (P. Lawrence and J. L. Strominger, J. Biol. Chem. 245, 3653 (1970); J. W. Kozarich, N. Tokuzo, E. Willoughby, J. L. Strominger, J. Biol. Chem. 252, 7525 (1977)). In this model, the sulfhydryl of sortase may function as a nucleophile at the peptide bond between threonine and glycine, thereby forming a thioester with the carboxyl of threonine and releasing the amino of glycine (FIG. 8A). Lipmann first used hydroxylamine to demonstrate the existence of acyl-enzyme intermediates as this strong nucieophile attacks thioester to form hydroxamate with carboxyl, thereby regenerating enzyme sulfhydryl (F. Lipmann and L. C. Tuttle, J. Biol. Chem. 161, 415 (1945)).

Hydroxylaminolysis of Surface Proteins

Figure 12A:
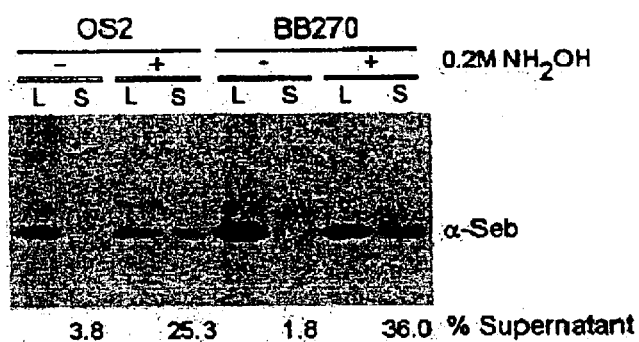
FIG. 12:
(A) depicts an SDS-PAGE gel analysis of a pulse chase analysis of surface protein anchoring to the cell wall in the presence or absence of release of proteins fro the surface by hydroxylamine.
(B) depicts an SDS-PAGE gel analysis of a pulse chase analysis of surface protein anchoring to the cell wall in the presence or absence of release of proteins fro the surface by hydroxylamine added either 5 min prior to labeling (prior), during pulse-labeling (pulse) or 5 min after quenching to *S. aureus* OS2 cultures.
(C) depicts a bar graph indicating that increasing amounts of hydroxylamine added 5 min prior to labeling of *S. aureus*

Hydroxylaminolysis of surface proteins was examined by pulse-labeling staphylococci with [$^{35}$S]methionine in either the presence or absence of 0.2 M NH$_2$OH. Cultures were labeled with [$^{35}$S]methionine and divided into two aliquots, each of which was precipitated with 5% TCA. One sample was boiled in hot SDS, whereas the other was first treated with lysostaphin to release all anchored surface protein, and then boiled in hot SDS. Surface protein (SEB-SPA$_{490-524}$) of mock treated staphylococci was insoluble in hot SDS (3.8%) unless the peptidoglycan had been digested with lysostaphin prior to boiling in SDS (100%)(FIG. 12A). Addition of 0.2 M NH$_2$OH caused 25.3% of all labeled SEB-SPA$_{490-524}$ to be released into the extra-cellular medium and to be soluble in hot SDS. This phenomenon was not strain specific as S. aureus OS2 and S. aureus BB270 displayed similar amounts of surface protein hydroxylaminolysis.

Figure 12B:
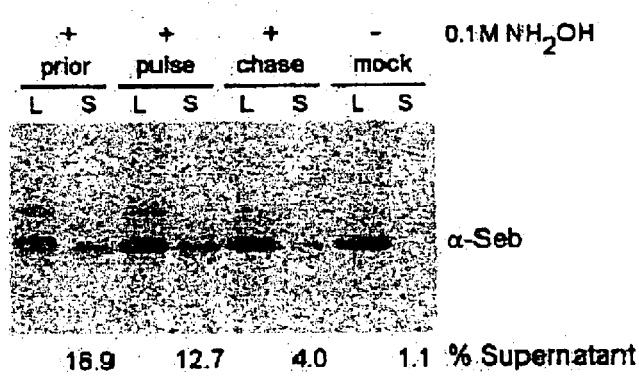
Figure 12C:
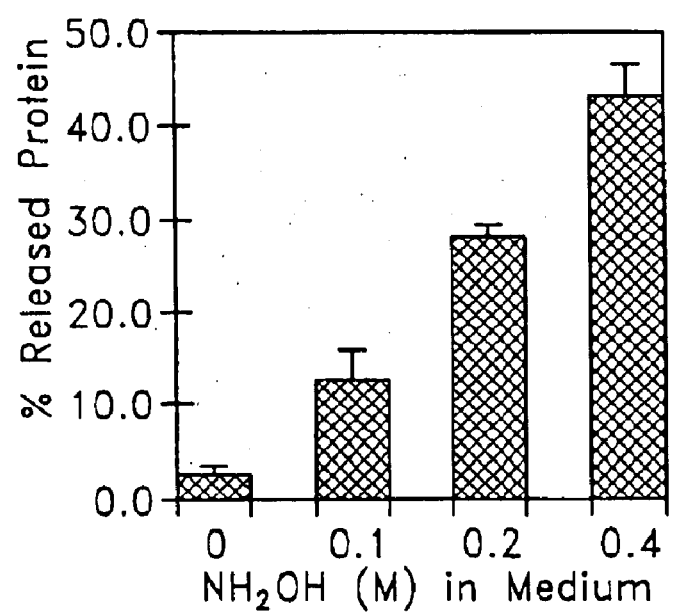

If the solubility of surface proteins in hot SDS is caused by hydroxylaminolysis of acyl-enzyme intermediates, addition of NH$_2$OH after the pulse labeling of staphylococci should not release SEB-SPA$_{490-524}$ as this polypeptide is rapidly anchored to the cell wall. Addition of NH$_2$OH either before or during the pulse with [$^{35}$S]methionine released surface proteins into the extra-cellular medium (16.9% and 12.7%, respectively) (FIG. 12B). Very little SDS-soluble SEB-SPA$_{490-524}$ was detected when NH$_2$OH was added after the pulse (4%). Increasing the amount of NH$_2$OH prior to pulse-labeling resulted in increased amounts of released surface proteins (FIG. 12C).

Characterization of NH$_2$OH-released Surface Proteins

Figure 13A:
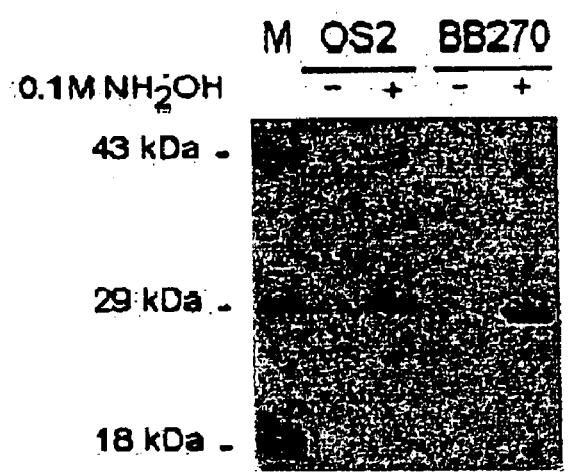
Figure 13B:
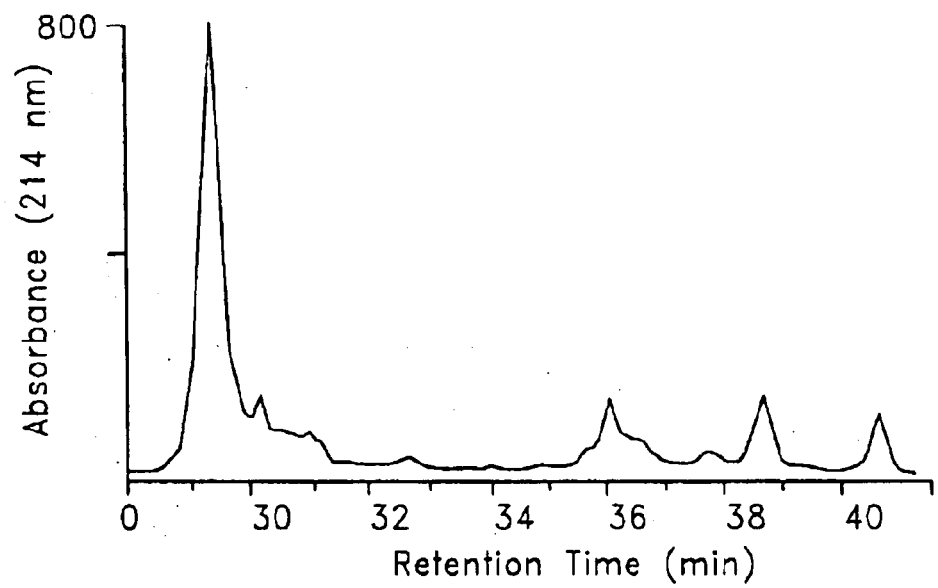
Figure 13C:
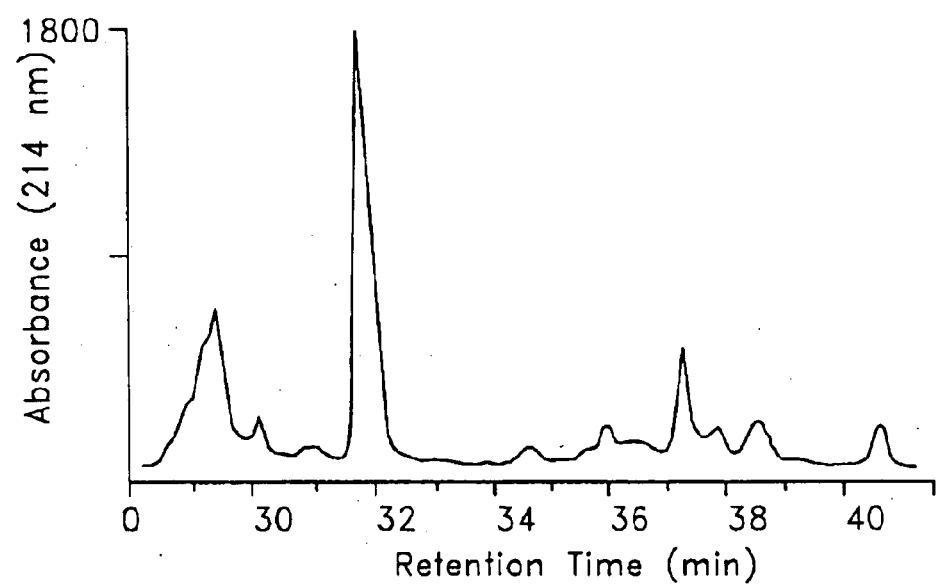

Hydroxylaminolysis of sortase acyl-intermediates should result in the formation of surface protein hydroxamate at the threonine of the LPXTG motif. To characterize NH$_2$OH-released surface protein, staphylococci (10$^{13}$ cfu) expressing the surface protein SEB-MH$_6$-CWS (H. Ton-That, K. F. Faull, O. Schneewind, J. Biol. Chem. 272, 22285 (1997)) were incubated in the presence or absence of 0.1 M NH$_2$OH. Samples were centrifuged to sediment bacteria and SEB-MH$_6$-CWS was purified from the supernatant by affinity chromatography and analyzed on Coomassie-stained SDS-PAGE. Treatment with 0.1 M NH$_2$OH caused the release of SEB-MH$_6$-CWS by S. aureus strains OS2 and BB270 (FIG. 13A). SEB-MH$_6$-CWS purified from strain BB270 was cleaved at methionine with cyanogen bromide. COOH-terminal peptides bearing anchor structures were purified by affinity chromatography and analyzed by rpHPLC (H. Ton-That, K. F. Faull, O. Schneewind, J. Biol. Chem. 272, 22285 (1997)). The chromatogram of anchor peptides released from mock treated bacteria revealed a major absorbance peak at 29% CH$_3$CN (FIG. 13B). The sample was subjected to electrospray-ionization mass spectrometry (ESI-MS) and a compound with an average mass of 2236 Da was detected. This measurement is consistent with the structure of anchor peptide linked to a branched cell wall tetrapeptide [L-Ala-D-iGln-L-Lys(NH$_2$—H$_6$AQALPET-Gly$_5$)-D-Ala, predicted mass 2235]. This surface protein species is not linked to the glycan strands of the staphylococcal cell wall and is therefore released into the culture medium. The chromatogram of anchor peptides released by treatment with 0.1 M NH$_2$OH revealed a major absorbance peak at 32% CH$_3$CN (FIG. 13C). ESI-MS identified a compound with the average mass of 1548 Da. When subjected to Edman degradation, the peptide sequence NH$_2$—H$_6$AQALPET* was obtained, in which the thirteenth cleavage cycle released a phenylthiohydantoin moiety of unknown structure. The predicted mass of NH$_2$—H$_6$AQALPET> (T> indicates threonine hydroxamate) is 1565 Da, 17 Da more than the observed mass of 1548 Da. Fractions of both chromatograms were scanned by rpHPLC for the presence of ion signals with an average mass of 1548, 1565 or 2236. rpHPLC fractions of anchor peptides from mock-treated cultures contained the compound with mass 2236, however no ions of the predicted mass 1548 or 1565 were detected. In contrast, rpHPLC fractions collected from anchor peptides of NH$_2$OH-treated staphylococci harbored compounds with an average mass of 1548 Da (NH$_2$—H$_6$AQALPET*, 32% CH$_3$CN) and 1565 Da (NH$_2$—H$_6$AQALPET>, 31% CH$_3$CN), but not the anchor peptide of 2235 Da. Thus, treatment with 0.1 M NH$_2$OH released surface protein from staphylococci as a hydroxamate of the threonine within the LPXTG motif, suggesting that sortase forms an acyl-enzyme intermediate with cleaved surface protein. The peptide NH$_2$—H$_6$AQALPET> appears to be unstable during our purification, thereby generating NH$_2$—H$_6$AQALPET* with a loss of 17 Da at the threonine hydroxmate.

Analysis of Sortase Hydroxylaminolysis Activity In Vitro in the Presence of NH$_2$OH If NH$_2$OH can release surface protein from staphylococci in vivo, sortase may catalyze the cleavage of LPXTG motif bearing peptides in the presence of NH$_2$OH in vitro. Fluoresence of the EDANS fluorophore within the peptide DABCYL-QALPETGEE-EDANS is quenched by the close proximity of DABCYL (G. T. Wang, E. Matayoshi, H. J. Huffaker, G. A. Krafft, Tetrahedon Lett. 31, 6493 (1990)). When the peptide is cleaved and the fluorophore separated from DABCYL, an increase in fluorescence is observed (E. D. Matayoshi, G. T. Wang, G. A. Krafft, J. Erickson, Science 247, 954 (1989)). Incubation of the LPXTG peptide with crude staphylococcal extracts caused only a small increase in fluorescence. However, the addition of 0.1 M NH$_2$OH to staphylococcal extracts resulted in a forty fold increase in fluorescence intensity (FIG. 14). This activity appears to be specific for sortase as it can be inhibited by pre-incubation of staphylococcal extracts with methanethiosulfonate (MTSET) (D. J. Smith, E. T. Maggio, G. L. Kenyon, Biochemistry 14, 764 (1975), a known inhibitor of the sorting reaction. These results suggest that sortase catalyzes the hydroxylaminolysis of LPXTG peptide in vitro. Thus, surface protein is cleaved between the threonine and the glycine of the LPXTG motif, resulting in the formation of a NH$_2$OH-sensitive thioester linkage between the carboxyl of threonine and the active site sulfhydryl of sortase. In vivo, the acyl-enzyme intermediate is resolved by a nucleophilic attack of the amino within the pentaglycine crossbridge. Recent observations suggest that the pentaglycine crossbridge of the lipid II precursor functions as a nucleophile for the sorting reaction. We show here that hydroxylamine can subsitute for pentaglycine both in vivo and in vitro.

Purification and Characterization of Sortase

When expressed in E. coli and analyzed by centrifugation of crude lysates, the staphylococcal SrtA protein sedimented with membranes. To obtain a soluble enzyme and to examine its properties, the NH$_2$-terminal membrane anchor segment of SrtA was replaced with a six histidine tag (SrtA$_{DN}$). SrtA$_{DN}$ was expressed in E. coli XL-1 Blue and purified by affinity chromatography from cleared lysates. When incubated with the LPXTG peptide and measured as an increase in fluorescence, SrtA$_{DN}$ catalyzed cleavage of the substrate. Addition of 0.2 M NH$_2$OH to this reaction resulted in an increase in fluorescence, indicating that cleavage of the LPXTG peptide occurred more efficiently. Hydroxylaminolysis of LPXTG peptide was dependent on the sulfhydryl of SrtA$_{DN}$ as pre-incubation with MTSET abolished all enzymatic activity. Methanethiosulfonate forms disulfide with sulfhydryl (D. J. Smith, E. T. Maggio, G. L. Kenyon, Biochemistry 14, 764 (1975); M. H. Akabas and A. Karlin, Biochemistry 34, 12496 (1995)) which can be reversed by reducing reagents such as dithiothreitol (DTT) (R. Pathak, T. L. Hendrickson, B. Imperiali, Biochemistry 34, 4179 (1995)). MTSET-inactivated SrtA$_{DN}$ was incubated in the presence of 10 mM DTT, which restored 80% of LPXTG peptide cleavage activity. The availability of purified, soluble sortase (SrtA$_{DN}$) and an in vitro assay for the hydroxylaminolysis of LPXTG peptide should allow the screening for compounds that interfere with the anchoring of surface protein in Gram-positive bacteria. Such compounds may be useful for the therapy of human infections with Gram-positive bacteria that have gained resistance to all known antibiotics.

Materials and Methods

Pulse-Chase Screen of Hydroxylaminolysis of Surface Proteins

Staphylococci were grown in minimal medium unil OD$_{600}$ 0.6 and pulse-labeled with 100 µCi Pro-Mix ([$^{35}$S] methionine and cysteine) for 1 min. Incorporation of radiolabel into polypeptides was quenched by the addition of 50 µl chase solution (100 mg/ml casamino acids, 20 mg/ml methionine and cysteine) and incubation was continued at 37° C. for 5 min. Two 0.5 ml aliquots of labeled culture were each precipitated with 0.5 ml 10% TCA, washed in acetone and dried under vacuum. One sample was suspended in 50 µl 0.5 M tris, 4% SDS and boiled. The other sample was first suspended in 1 ml 0.5 M Tris pH 7.0 and the cell wall digested for 1 hour at 37° C. by adding 50 µl 2 mg/ml lysostaphin. The sample was precipitated with 75 µl 100% TCA, washed in acetone, dried and then boiled in SDS. Aliquots were subjected to immunoprecipitation with a-SEB and analyzed after SDS-PAGE on Phosphorlmager.

Purification of NH$_2$OH Surface Proteins

Staphylococci (10$^{13}$ cells) were incubated in 200 ml 50 mM Tris-HCl, pH 7.0 with or without 0.1 M NH$_2$OH for 60 min. Sampes were centrifuged at 10,000× g for 15 min and the supernatants applied to 1 ml Ni-NTA column, pre-equilibrated with column buffer (CB, 50 mM Tris-HCl, 150 mM NaCl, pH 7.5). The column was washed first with 20 ml CB and 20 ml CB containing 10% glycerol and eluted with 4 ml of column buffer and 0.5 imidazol. Aliquots were mixed with sample buffer and separated on SDS-PAGE. The eluate was precipitated with TFA (10%), washed in acetone and dried under vacuum. The sample was suspended in 600 µl 70% formic acid and, after addition of a crystal of cyanogen bromide, incubated overnight. Cleaved peptides were repeatedly dried and suspended in water to evaporate cyanogen bromde, solubilized in 1 ml buffer A and subjected to affinity chromatography as previously described. Peptides were eluted in 4 ml of 6 M guanidine-hydrochloride, 0.2 M acetic acid, desalted over C18 cartridge and dried. Pellets were solubilized in 50 µl buffer B (8 M urea, 50 mM phosphate, 10 mM Tris-HCl, pH 7.3) and subjected to rpHPLC on C18 column (Hypersil, Keystone Scientific) with a linear gradient from 1%–99% CH$_3$CN in 0.1% TFA in 90 minutes. MALDI-MS and ESI-MS was performed as described (H. Ton-That, K. F. Faull, O. Schneewind (1997) J. Biol. Chem. 272:22285–22292).

Identification of Peptide Structure by Mass Spectrometry

The structure of the peptides with mass 1548 and 1565 was determined by tandem mass spectrometry, MS/MS using the parent ions. Collisionally induced dissociation of the parent ions produced daughter ion spectra consistent with compound structures $NH_2$—$H_6$AQALPET> (T> is threonine hydroxamate, predicted compound mass 1565) and $NH_2$—$H_6$AQALPET* (T* represents a loss of 17 Da of threonine hydroxamate; the structure of this residue is unknown).

Assay of Sortase activity by Fluorescent Assay

Reactions were assembled in a volume of 120 µl containing 50 mM Tris-HCl, 150 mM NaCl, pH 7.5. The concentration of LPXTG peptide substrate (DABCYL-QALPETGEE-EDANS) was 10 µM, of MTSET 5 mM, of $NH_2OH$ 0.2 M. Staphylococcal cell extracts were obtained by subjecting 1013 cells to disrubtion in a bead beater instrument. The crude extract was subjected to slow speed centrifugation at 3,000× g for 15 min to remove beads and intact cells. A 10 µl aliquot of the supernatant, containing approximately 50 mg/ml protein, was used as enzyme preparation. Incubations were carried out for 1 hour at 37° C., followed by centrifugation of the sample at 15,000× g for 5 min. The supernatant was subjected to analysis in a fluorimeter using 395 nm for excitation and 495 nm for recordings.

Purification of Sortase by Addition of Histidine Tag

The primers orf6N-ds-B (5'-AAAGGATCCAAACCACATATCGATAATTATC-3') and orf6C-dT-B (5'-AAAGGATCCTTTGACTTCTGTAGCTACAMG-3') were used to PCR amplify the srtA sequence from the chromosome of S. aureus OS2. The DNA fragment was cut with BamHI, inserted into pQE16 (Qiagen) cut BamHI to generate pHTT5, transformed into E. coli XL-1 Blue and selected on Luria broth with ampicillin (100 µg/ml). E coli XL-1 Blue (pHTT5) ($10^{12}$ cells) were suspended in 30 ml C buffer (50 mM Bis-Tris-HCl, 150 mM NaCl, 10% glycerol, pH 7.2) and lysed by one passage through a French pressure cell at 14,000 psi. The extract was centrifuged at 29,000× g for 30 min and the supernatant applied to 1 ml Ni-NTA resin, pre-equilibrated with C buffer. The column was washed with 40 ml C buffer and $SrtA_{DN}$ protein was eluted in 4 ml C buffer with 0.5 M imidazol at a concentration of 30 µg/µl.

Reactions were assembled in a volume of 260 µl containing 50 mM Hepes buffer, 150 mM NaCl, pH 7.5 and as indicated 5 µM $SrtA_{DN}$ in 50 mM BisTris, pH 7.5, 10 µM LPXTG peptide (DABCYL-QALPETGEE-EDANS), 10 µM TGXLP peptide (DABCYL-QATGELPEE-EDANS), 5 mM MTSET, 0.2 M $NH_2OH$, 5 mM pHMB or 10 mM DTT. Incubations were carried out for 1 hour at 37° C. Samples were analyzed in a fluorimeter using 395 nm for excitation and 495 nm for recordings.

EXAMPLE 4

Identification of a Second Sortase Gene, srtB

A second sortase gene, srtB, was identified with Blast searches using the srtA gene as query (SEQ ID NO:2). All S. aureus strains examined had both srtA and srtB genes. The srtB gene (SEQ ID NO:38) specifies a polypeptide chain of 244 amino acids (FIG. 6B; SEQ. ID. No:37). Alignment of SrtB and SrtA amino acid sequences indicates that SrtB has 22% identity and 37% similarity with the sequence of SrtA as well as 11 conserved amino acid residues. This degree of identity and similarity are the degree of identity and similarity determined with the Blast program (T. A. Tatusova & T. L. Madden, "Blast 2 Sequences—A New Tool for Comparing Protein and Nucleotide Sequences," FEMS Microbiol. Lett. 174:247–250 (1999).

Role of Multiple Sortase Enzymes in Staphylococci

The N-terminal membrane anchor segment of SrtB (residues 2–25) were replaced with a six-histidine tag (SrtBDN). In the absence of the peptidoglycan substrane, SrtA DN catalyzes peptide bond hydrolysis and cleaves LPETG peptide, presumably between the threonine and the glycine (Ton-That et al., 2000). This reaction was inhibited with methylmethane thiosulfonate, indicating that SrtB sortase catalyzes peptide bond hydrolysis and transpeptidation reaction, also via the conserved cystein residue (FIG. 14).

S. aureus knockout variants were generated by replacing the srtB gene of wild-type S. aureus Newman with the ermC marker gene (strain SKM9). Elimination of the srtB did not result in a defect in cell wall anchoring of surface proteins such as: protein A, FnbA, FnbB or ClfA. However, it is likely that srtB mutant staphylococci display a sorting defect for some of the remaining surface proteins. Thus, SrtB and SrtA catalyze similar reactions using different surface protein substrates. It is possible that different sortase enzymes modify specific secretion pathways. For example, SrtA with the Sec-1 secretion pathway and SrtB with the Sec-2 secretion pathway, or vice-versa. Presence of multiple sets of secretion, signal peptidase and sortase genes in S. aureus indicate existence of more than one pathway for surface protein transport.

Effect of srtB Knockout Variant S. aureus on in vivo Infectivity

The in vivo activity of srtB mutant stalphylococci was determined using a kidney staphylococcal abscess assay. S. aureus Newman and the srtB mutant, isogenic srtB:ermC knockout variant SKM7 were injected into the tail vein of Balb/c mice. Infection was allowed to proceed for 5 days. On day 5, all infected animals were euthanized, and their kidneys excised and homogenized. Kidney homogenates were then plated on tryptic soy agar plates. The level of staphylococcal infection in each animal, resulting from either the wild type (wt) or mutant strain was then correlated with the number of staphylococci obtained per kidney. FIG. 5 indicates the number of staphylococci obtained per kidney in animals infected with either S. aureus Newman (wt) or SKM7 (srtB mutant).

Advantages of the Present Invention

In isolating and characterizing genes for S. aureus sortase-transamidase enzyme, we have determined existence of a new site for antibiotic action that can be used to screen new antibiotics as well as a target for new antibiotics active against Gram-positive pathogens, such as Staphylococcus, Actinomyces, Mycobacterium, Streptococcus, Bacillus, and other medically important Gram-positive pathogens increasingly resistant to conventional antibiotics. The availability of substantially purified S. aureus sortase-transamidase enzyme provides a method of screening compounds for inhibition of the enzyme.

Purified sortase-transamidase enzymes also yield methods for surface display of peptides and proteins that have advantages over phage display, as well as providing methods for producing vaccines against a large variety of antigens that can be covalently bound to the surfaces of Gram-positive bacteria.

Although the present invention has been described with considerable detail, with reference to certain preferred versions thereof, other versions and embodiments are possible.Therefore, the scope of the invention is determined by the following claims.

We claim:

1. A substantially purified sortase-transamidase enzyme from a Gram-positive bacterium, the enzyme catalyzing a reaction that covalently cross-links the carboxyl terminus of a protein having a sorting signal to the peptidoglycan of a Gram-positive bacterium, and comprising

M-R-M-K-R-F-L-T-I-V-Q-I-L-L-V-V-I-I-I-F-G-Y-K-

I-V-Q-T-Y-I-E-D-K-Q-E-R-A-N-Y-E-K-L-Q-Q-K-F-Q-M-

L-M-S-K-H-Q-A-H-V-R-P-Q-F-E-S-L-E-K-I-N-K-D-I-V-

G-W-I-K-L-S-G-T-S-L-N-Y-P-V-L-Q-G-K-T-N-H-D-Y-L-

N-L-D-F-E-R-E-H-R-R-K-G-S-I-F-M-D-F-R-N-E-L-K-I-

L-N-H-N-T-I-L-Y-G-H-H-V-G-D-N-T-M-F-D-V-L-E-D-Y-

L-K-Q-S-F--Y-E-K-H-K-I-I-E-F-D-N-K-Y-G-K-Y-Q-L-

Q-V-F-S-A-Y-K-T-T-T-K-D-N-Y-I-R-T-D-F-E-N-D-Q-D-

Y-Q-Q-F-L-D-E-T-K-R-K-S-V-I-N-S-D-V-N-V-T-V-K-D-

K-I-M-T-L-S-T-C-E-D-A-Y-S-E-T-T-K-R-I-V-V-V-A-K-

I-I-K-V-S (SEQ ID NO:38).

2. The substantially purified sortase-transamidase enzyme of claim 1 wherein the Gram-positive bacterium is *Staphylococcus aureus*.

3. The substantially purified sortase-transamidase enzyme of claim 1 wherein the enzyme has a molecular weight of about 29,076 daltons.

4. Substantially purified sortase-transamidase enzyme produced by a process comprising the steps of:
 a) culturing a host cell transfected with nucleic acid encoding the sortase-transamidase enzyme of claim 1 under conditions in which the host cell expresses the encoded sortase-transamidase enzyme; and
 b) purifying the expressed enzyme to produce substantially purified sortase-transamidase enzyme.

5. A protein molecule comprising the substantially purified sortase-transamidase enzyme of claim 1 extended at its carboxyl-terminus with a sufficient number of histidine residues to allow specific binding of the protein molecule to a nickel-sepharose column through the histidine residues added at the carboxyl-terminus.

6. A conjugate comprising the sortase-transamidase enzyme of claim 1 covalently conjugated to an antibiotic or a detection reagent.

7. The conjugate of claim 6 wherein said sortase-transamidase enzyme is conjugated to an antibiotic.

8. The conjugate of claim 7 wherein the antibiotic is selected from the group consisting of a penicillin, ampicillin, vancomycin, gentamicin, streptomycin, a cephalosporin, amikacin, kanamycin, neomycin, paromomycin, tobramycin, ciprofloxacin, clindamycin, rifampin, chloramphenicol, and norfloxacin.

9. The conjugate of claim 6 wherein said sortase-transamidase enzyme is conjugated to a detection reagent.

10. A composition comprising:
 a) the conjugate of claim 6; and
 b) a pharmaceutically acceptable carrier.

* * * * *

SEQUENCE LISTING

<160> NUMBER OF SEQ ID NOS: 40

<210> SEQ ID NO 1
<211> LENGTH: 5
<212> TYPE: PRT
<213> ORGANISM: Bacteria
<220> FEATURE:
<221> NAME/KEY: UNSURE
<222> LOCATION: 3
<223> OTHER INFORMATION: Xaa = any of the 20 naturally occurring L-amino
      acids.

<400> SEQUENCE: 1

Leu Pro Xaa Thr Gly
       1               5

<210> SEQ ID NO 2
<211> LENGTH: 621
<212> TYPE: DNA
<213> ORGANISM: Staphylococcus aureas

<400> SEQUENCE: 2
atgaaaaaat ggacaaatcg attaatgaca atcgctggtg tggtacttat cctagtggca      60
      gcatatttgt ttgctaaacc acatatcgat aattatcttc acgataaaga taaagatgaa     120
      aagattgaac aatatgataa aaatgtaaaa gaacaggcga gtaaagataa aaagcagcaa     180
      gctaaacctc aaattccgaa agataaatcg aaagtggcag gctatattga aattccagat     240
      gctgatatta agaaccagt atatccagga ccagcaacac ctgaacaatt aaataaggt     300
      gtaagctttg cagaagaaaa tgaatcacta tgatgatcaaa atatttcaat tgcaggacac     360
      actttcattg accgtccgaa ctatcaattt acaaatctta aagcagccaa aaaggtagt     420
      atggtgtact ttaaagttgg taatgaaaca cgtaagtata aatgacaag tataagagat     480
      gttaagccta cagatgtagg agttctagat gaacaaaaag gtaaagataa acaattaaca     540
      ttaattactt gtgatgatta caatgaaaag acaggcgttt gggaaaaacg taaatctttt     600
      gtagctacag aagtcaaata a                                               621

<210> SEQ ID NO 3
<211> LENGTH: 206
<212> TYPE: PRT
<213> ORGANISM: Staphylococcus aureus

<400> SEQUENCE: 3

Met Lys Lys Trp Thr Asn Arg Leu Met Thr Ile Ala Gly Val Val Leu
       1               5                  10                  15
      Ile Leu Val Ala Ala Tyr Leu Phe Ala Lys Pro His Ile Asp Asn Tyr
                      20                  25                  30
      Leu His Asp Lys Asp Lys Asp Glu Lys Ile Glu Gln Tyr Asp Lys Asn
                      35                  40                  45
      Val Lys Glu Gln Ala Ser Lys Asp Lys Lys Gln Ala Lys Pro Gln
              50                  55                  60
      Ile Pro Lys Asp Lys Ser Lys Val Ala Gly Tyr Ile Glu Ile Pro Asp
       65                  70                  75                  80
      Ala Asp Ile Lys Glu Pro Val Tyr Pro Gly Pro Ala Thr Pro Glu Gln
                      85                  90                  95
      Leu Asn Arg Gly Val Ser Phe Ala Glu Glu Asn Glu Ser Leu Asp Asp
                     100                 105                 110
      Gln Asn Ile Ser Ile Ala Gly His Thr Phe Ile Asp Arg Pro Asn Tyr
                     115                 120                 125
      Gln Phe Thr Asn Leu Lys Ala Ala Lys Lys Gly Ser Met Val Tyr Phe
                     130                 135                 140
      Lys Val Gly Asn Glu Thr Arg Lys Tyr Lys Met Thr Ser Ile Arg Asp
      145                 150                 155                 160
      Val Lys Pro Thr Asp Val Gly Val Leu Asp Glu Gln Lys Gly Lys Asp
                     165                 170                 175
      Lys Gln Leu Thr Leu Ile Thr Cys Asp Asp Tyr Asn Glu Lys Thr Gly
                     180                 185                 190
      Val Trp Glu Lys Arg Lys Ile Phe Val Ala Thr Glu Val Lys
                     195                 200                 205

<210> SEQ ID NO 4
<211> LENGTH: 227
<212> TYPE: PRT

<213> ORGANISM: Streptococcus pyogenes

<400> SEQUENCE: 4

```
Met Glu Glu Val Trp Gln Lys Ala Lys Ala Tyr Asn Ala Arg Leu Gly
 1               5                  10                  15
Thr Gln Pro Val Pro Asp Ala Phe Ser Phe Arg Asp Gly Ile His Asp
            20                  25                  30
Lys Asn Tyr Glu Ser Leu Leu Gln Ile Glu Asn Asn Asp Ile Met Gly
        35                  40                  45
Tyr Val Glu Val Pro Ser Ile Lys Val Thr Leu Pro Ile Tyr His Tyr
    50                  55                  60
Thr Thr Asp Glu Val Leu Thr Lys Gly Ala Gly His Leu Phe Gly Ser
65                  70                  75                  80
Ala Leu Pro Val Gly Gly Asp Gly Thr His Thr Val Ile Ser Ala His
                85                  90                  95
Arg Gly Leu Pro Ser Ala Glu Met Phe Thr Asn Leu Asn Leu Val Lys
            100                 105                 110
Lys Gly Asp Thr Phe Tyr Phe Arg Val Leu Asn Lys Val Leu Ala Tyr
        115                 120                 125
Lys Val Asp Gln Ile Leu Thr Val Glu Pro Asp Gln Val Thr Ser Leu
    130                 135                 140
Ser Gly Val Met Gly Lys Asp Tyr Ala Thr Leu Val Thr Cys Thr Pro
145                 150                 155                 160
Tyr Gly Val Asn Thr Lys Arg Leu Leu Val Arg Gly His Arg Ile Ala
                165                 170                 175
Tyr His Tyr Lys Lys Tyr Gln Gln Ala Lys Ala Met Lys Leu Val
            180                 185                 190
Asp Lys Ser Arg Met Trp Ala Glu Val Val Cys Ala Ala Phe Gly Val
        195                 200                 205
Val Ile Ala Ile Ile Leu Val Phe Met Tyr Ser Arg Val Ser Ala Lys
    210                 215                 220
Lys Ser Lys
225
```

<210> SEQ ID NO 5
<211> LENGTH: 365
<212> TYPE: PRT
<213> ORGANISM: Actinomyces naeslundii

<400> SEQUENCE: 5

```
Met Gly Leu Leu Thr Tyr Pro Thr Ala Ala Ser Trp Val Ser Gln Tyr
 1               5                  10                  15
Asn Gln Ser Lys Val Thr Ala Asp Tyr Ser Ala Gln Val Asp Gly Ala
            20                  25                  30
Arg Pro Asp Ala Lys Thr Gln Val Glu Gln Ala His Ala Tyr Asn Asp
        35                  40                  45
Ala Leu Ser Ala Gly Ala Val Leu Glu Ala Asn Asn His Val Pro Thr
    50                  55                  60
Gly Ala Gly Ser Ser Lys Asp Ser Ser Leu Gln Tyr Ala Asn Ile Leu
65                  70                  75                  80
Lys Ala Asn Asn Glu Gly Leu Met Ala Arg Leu Lys Ile Pro Ser Ile
                85                  90                  95
Ser Leu Asp Leu Pro Val Tyr His Gly Thr Ala Asp Asp Thr Leu Leu
            100                 105                 110
Lys Gly Leu Gly His Leu Glu Gly Thr Ser Leu Pro Val Gly Gly Glu
        115                 120                 125
Gly Thr Arg Ser Val Ile Thr Gly His Arg Gly Leu Ala Glu Ala Thr
    130                 135                 140
Met Phe Thr Asn Leu Asp Lys Val Lys Thr Gly Asp Ser Leu Ile Val
145                 150                 155                 160
Glu Val Phe Gly Glu Val Leu Thr Tyr Arg Val Thr Ser Thr Lys Val
                165                 170                 175
Val Glu Pro Glu Glu Thr Glu Ala Leu Arg Val Glu Gly Lys Asp
            180                 185                 190
Leu Leu Thr Leu Val Thr Cys Thr Pro Leu Gly Ile Asn Thr His Arg
        195                 200                 205
Ile Leu Leu Thr Gly Glu Arg Ile Tyr Pro Thr Pro Ala Lys Asp Leu
    210                 215                 220
Ala Ala Ala Gly Lys Arg Pro Asp Val Pro His Phe Pro Trp Trp Ala
225                 230                 235                 240
Val Gly Leu Ala Ala Gly Leu Ile Val Val Gly Leu Tyr Leu Trp Arg
                245                 250                 255
Ser Gly Tyr Ala Ala Ala Arg Ala Lys Glu Arg Ala Leu Ala Arg Ala
            260                 265                 270
Arg Ala Ala Gln Glu Glu Pro Gln Pro Gln Thr Trp Ala Glu Gln Met
        275                 280                 285
```

```
            Arg Ile Trp Met Asp Asp Ala Gly Val Glu Pro Gln Arg Trp Phe
                290                 295                 300
            Thr Asp Leu Pro Val Pro Pro Gln Pro Ser Glu Met Glu Asn Leu Ala
            305                 310                 315                 320
            Leu Leu Glu Glu Ile Ala Ser Leu Ser Ala Pro Ser Gly Arg Trp Asp
                            325                 330                 335
            Asp Gln Glu Leu Ile Asp Thr Ala Glu Ile Pro Val Leu Asp Ala Thr
                        340                 345                 350
            Arg Pro Ser Ala Gly Thr Ser Gly Arg Thr His Arg Leu
                    355                 360                 365

<210> SEQ ID NO 6
<211> LENGTH: 284
<212> TYPE: PRT
<213> ORGANISM: Enterococcus faecalis

<400> SEQUENCE: 6

Met Lys Ser Lys Lys Arg Arg Ile Ile Asp Gly Phe Met Ile Leu
            1               5                   10                  15
            Leu Leu Ile Ile Gly Ile Gly Ala Phe Ala Tyr Pro Phe Val Ser Asp
                            20                  25                  30
            Ala Leu Asn Asn Tyr Leu Asp Gln Gln Ile Ile Ala His Tyr Gln Ala
                        35                  40                  45
            Lys Ala Ser Gln Glu Asn Thr Lys Glu Met Ala Glu Leu Gln Glu Lys
                    50                  55                  60
            Met Glu Lys Lys Asn Gln Glu Leu Ala Lys Lys Gly Ser Asn Pro Gly
            65                  70                  75                  80
            Leu Asp Pro Phe Ser Glu Thr Gln Lys Thr Thr Lys Pro Asp Lys
                            85                  90                  95
            Ser Tyr Phe Glu Ser His Thr Ile Gly Val Leu Thr Ile Pro Lys Ile
                        100                 105                 110
            Asn Val Arg Leu Pro Ile Phe Asp Lys Thr Asn Ala Leu Leu Leu Glu
                    115                 120                 125
            Lys Gly Ser Ser Leu Leu Glu Gly Thr Ser Tyr Pro Thr Gly Gly Thr
            130                 135                 140
            Asn Thr His Ala Val Ile Ser Gly His Arg Gly Leu Pro Gln Ala Lys
            145                 150                 155                 160
            Leu Phe Thr Asp Leu Pro Glu Leu Lys Lys Gly Asp Glu Phe Tyr Ile
                            165                 170                 175
            Glu Val Asn Gly Lys Thr Leu Ala Tyr Gln Val Asp Gln Ile Lys Thr
                        180                 185                 190
            Val Glu Pro Thr Asp Thr Lys Asp Leu His Ile Glu Ser Gly Gln Asp
                    195                 200                 205
            Leu Val Thr Leu Leu Thr Cys Thr Pro Tyr Met Ile Asn Ser His Arg
            210                 215                 220
            Leu Leu Val Arg Gly His Arg Ile Pro Tyr Gln Pro Glu Lys Ala Ala
            225                 230                 235                 240
            Ala Gly Met Lys Lys Val Ala Gln Gln Asn Leu Leu Leu Trp Thr
                            245                 250                 255
            Leu Leu Leu Ile Ala Cys Ala Leu Ile Ile Ser Gly Phe Ile Ile Trp
                        260                 265                 270
            Tyr Lys Arg Arg Lys Lys Thr Thr Arg Lys Pro Lys
                    275                 280

<210> SEQ ID NO 7
<211> LENGTH: 246
<212> TYPE: PRT
<213> ORGANISM: Streptococcus mutans

<400> SEQUENCE: 7

Met Lys Lys Glu Arg Gln Ser Arg Lys Lys Arg Ser Phe Leu Arg Thr
            1               5                   10                  15
            Phe Leu Pro Ile Leu Leu Leu Val Ile Gly Leu Ala Leu Ile Phe Asn
                            20                  25                  30
            Thr Pro Ile Arg Asn Ala Leu Ile Ala Trp Asn Thr Asn Arg Tyr Gln
                        35                  40                  45
            Val Ser Asn Val Ser Lys Asp Ile Glu His Asn Lys Ala Ala His
                    50                  55                  60
            Ser Ser Phe Asp Phe Lys Lys Val Glu Ser Ile Ser Thr Gln Ser Val
            65                  70                  75                  80
            Leu Ala Ala Gln Met Ala Ala Gln Lys Leu Pro Val Ile Gly Ile
                            85                  90                  95
            Ala Ile Pro Asp Leu Lys Ile Asn Leu Pro Ile Phe Lys Gly Leu Asp
                        100                 105                 110
            Asn Val Gly Leu Thr Tyr Gly Ala Gly Thr Met Lys Asn Asp Gln Val
```

```
            115                 120                 125
    Met Gly Glu Asn Asn Tyr Ala Leu Ala Ser His His Val Phe Gly Met
            130                 135                 140
    Thr Gly Ser Ser Gln Met Leu Phe Ser Pro Leu Glu Arg Ala Lys Glu
    145                 150                 155                 160
    Gly Met Glu Ile Tyr Leu Thr Asp Lys Asn Lys Val Tyr Thr Tyr Val
                        165                 170                 175
    Ile Ser Glu Val Lys Thr Val Thr Pro Glu His Val Glu Val Ile Asp
                180                 185                 190
    Asn Arg Pro Gly Gln Asn Glu Val Thr Leu Val Thr Cys Thr Asp Ala
            195                 200                 205
    Gly Ala Thr Ala Arg Thr Ile Val His Gly Thr Tyr Lys Gly Glu Asn
            210                 215                 220
    Asp Phe Asn Lys Thr Ser Lys Lys Ile Lys Lys Ala Phe Arg Gln Ser
    225                 230                 235                 240
    Tyr Asn Gln Ile Ser Phe
                        245
```

<210> SEQ ID NO 8
<211> LENGTH: 198
<212> TYPE: PRT
<213> ORGANISM: Bacillus subtilis

<400> SEQUENCE: 8

```
    Met Lys Lys Val Ile Pro Leu Phe Ile Ile Ala Ala Gly Leu Val Ile
    1               5                   10                  15
    Ala Gly Tyr Gly Gly Phe Lys Leu Ile Asp Thr Asn Thr Lys Thr Glu
                20                  25                  30
    Gln Thr Leu Lys Glu Ala Lys Leu Ala Ala Lys Pro Gln Glu Ala
            35                  40                  45
    Ser Gly Thr Lys Asn Ser Thr Asp Gln Ala Lys Asn Lys Ala Ser Phe
        50                  55                  60
    Lys Pro Glu Thr Gly Gln Ala Ser Gly Ile Leu Glu Ile Pro Lys Ile
    65                  70                  75                  80
    Asn Ala Glu Leu Pro Ile Val Glu Gly Thr Asp Ala Asp Leu Glu
                    85                  90                  95
    Lys Gly Val Gly His Tyr Lys Asp Ser Tyr Tyr Pro Asp Glu Asn Gly
                100                 105                 110
    Gln Ile Val Leu Ser Gly His Arg Asp Thr Val Phe Arg Thr Gly
            115                 120                 125
    Glu Leu Glu Lys Gly Asp Gln Leu Arg Leu Leu Ser Tyr Gly Glu
        130                 135                 140
    Phe Thr Tyr Glu Ile Val Lys Thr Lys Ile Val Asp Lys Asp Thr
    145                 150                 155                 160
    Ser Ile Ile Thr Leu Gln His Glu Lys Glu Glu Leu Ile Leu Thr Thr
                    165                 170                 175
    Cys Tyr Pro Phe Ser Tyr Val Gly Asn Ala Pro Lys Arg Tyr Ile Ile
                180                 185                 190
    Tyr Gly Lys Arg Val Thr
                195
```

<210> SEQ ID NO 9
<211> LENGTH: 25
<212> TYPE: PRT
<213> ORGANISM: Staphylococcus aureus

<400> SEQUENCE: 9

```
    Glu Glu Asn Pro Phe Ile Gly Thr Thr Val Phe Gly Gly Leu Ser Leu
    1               5                   10                  15
    Ala Leu Gly Ala Ala Leu Leu Ala Gly
                20                  25
```

<210> SEQ ID NO 10
<211> LENGTH: 23
<212> TYPE: PRT
<213> ORGANISM: Staphylococcus aureus

<400> SEQUENCE: 10

```
    Gly Glu Glu Ser Thr Asn Lys Gly Met Leu Phe Gly Gly Leu Phe Ser
    1               5                   10                  15
    Ile Leu Gly Leu Ala Leu Leu
                20
```

```
<210> SEQ ID NO 11
<211> LENGTH: 24
<212> TYPE: PRT
<213> ORGANISM: Staphylococcus sobrinos

<400> SEQUENCE: 11

Asp Ser Ser Asn Ala Tyr Leu Pro Leu Leu Gly Leu Val Ser Leu Thr
        1               5                   10                  15
        Ala Gly Phe Ser Leu Leu Gly Leu
                    20

<210> SEQ ID NO 12
<211> LENGTH: 24
<212> TYPE: PRT
<213> ORGANISM: Enterococcus faecalis

<400> SEQUENCE: 12

Glu Lys Gln Asn Val Leu Leu Thr Val Val Gly Ser Leu Ala Ala Met
        1               5                   10                  15
        Leu Gly Leu Ala Gly Leu Gly Phe
                    20

<210> SEQ ID NO 13
<211> LENGTH: 23
<212> TYPE: PRT
<213> ORGANISM: Streptococcus pyogenes

<400> SEQUENCE: 13

Ser Ile Gly Thr Tyr Leu Phe Lys Ile Gly Ser Ala Ala Met Ile Gly
        1               5                   10                  15
        Ala Ile Gly Ile Tyr Ile Val
                    20

<210> SEQ ID NO 14
<211> LENGTH: 22
<212> TYPE: PRT
<213> ORGANISM: Listeria monocytogenes

<400> SEQUENCE: 14

Asp Ser Asp Asn Ala Leu Tyr Leu Leu Gly Leu Leu Ala Val Gly
        1               5                   10                  15
        Thr Ala Met Ala Leu Thr
                    20

<210> SEQ ID NO 15
<211> LENGTH: 5
<212> TYPE: PRT
<213> ORGANISM: Staphylococcus aureus

<400> SEQUENCE: 15

Arg Arg Arg Glu Leu
       1               5

<210> SEQ ID NO 16
<211> LENGTH: 9
<212> TYPE: PRT
<213> ORGANISM: Staphylococcus aureus

<400> SEQUENCE: 16

Arg Arg Asn Lys Lys Asn His Lys Ala
       1               5

<210> SEQ ID NO 17
<211> LENGTH: 5
<212> TYPE: PRT
<213> ORGANISM: Staphylococcus sobrinus
```

```
<400> SEQUENCE: 17

Arg Arg Lys Gln Asp
      1               5

<210> SEQ ID NO 18
<211> LENGTH: 7
<212> TYPE: PRT
<213> ORGANISM: Enterococcus faecalis

<400> SEQUENCE: 18

Lys Arg Arg Lys Glu Thr Lys
      1               5

<210> SEQ ID NO 19
<211> LENGTH: 5
<212> TYPE: PRT
<213> ORGANISM: Streptococcus pyogenes

<400> SEQUENCE: 19

Lys Arg Arg Lys Ala
      1               5

<210> SEQ ID NO 20
<211> LENGTH: 8
<212> TYPE: PRT
<213> ORGANISM: Actinomyces viscosus

<400> SEQUENCE: 20

Lys Arg Arg His Val Ala Lys His
      1               5

<210> SEQ ID NO 21
<211> LENGTH: 5
<212> TYPE: PRT
<213> ORGANISM: Streptococcus aglactiae

<400> SEQUENCE: 21

Lys Arg Arg Lys Ser
      1               5

<210> SEQ ID NO 22
<211> LENGTH: 6
<212> TYPE: PRT
<213> ORGANISM: Streptococcus pyogenes

<400> SEQUENCE: 22

Lys Arg Lys Glu Glu Asn
      1               5

<210> SEQ ID NO 23
<211> LENGTH: 5
<212> TYPE: PRT
<213> ORGANISM: Mutated derived from streptococcus pyogenes

<400> SEQUENCE: 23

Arg Arg Arg Glu Ser
      1               5

<210> SEQ ID NO 24
<211> LENGTH: 5
<212> TYPE: PRT
<213> ORGANISM: Mutated derived from streptococcus pyogenes

<400> SEQUENCE: 24
```

-continued

```
        Arg Arg Arg Ser Leu
          1               5

<210> SEQ ID NO 25
<211> LENGTH: 5
<212> TYPE: PRT
<213> ORGANISM: Mutated derived from streptococcus pyogenes

<400> SEQUENCE: 25

Arg Arg Ser Glu Leu
          1               5

<210> SEQ ID NO 26
<211> LENGTH: 5
<212> TYPE: PRT
<213> ORGANISM: Mutated derived from streptococcus pyogenes

<400> SEQUENCE: 26

Arg Ser Arg Glu Leu
          1               5

<210> SEQ ID NO 27
<211> LENGTH: 5
<212> TYPE: PRT
<213> ORGANISM: Mutated derived from streptococcus pyogenes

<400> SEQUENCE: 27

Ser Arg Arg Glu Leu
          1               5

<210> SEQ ID NO 28
<211> LENGTH: 5
<212> TYPE: PRT
<213> ORGANISM: Mutated derived from streptococcus pyogenes

<400> SEQUENCE: 28

Arg Arg Ser Ser Ser
          1               5

<210> SEQ ID NO 29
<211> LENGTH: 5
<212> TYPE: PRT
<213> ORGANISM: Mutated derived from streptococcus pyogenes

<400> SEQUENCE: 29

Arg Ser Arg Ser Ser
          1               5

<210> SEQ ID NO 30
<211> LENGTH: 5
<212> TYPE: PRT
<213> ORGANISM: Mutated derived from streptococcus pyogenes

<400> SEQUENCE: 30

Ser Arg Arg Ser Ser
          1               5

<210> SEQ ID NO 31
<211> LENGTH: 19
<212> TYPE: PRT
<213> ORGANISM: Mutated derived from streptococcus pyogenes

<400> SEQUENCE: 31

His His His His His His Ala Gln Ala Leu Glu Pro Thr Gly Glu Glu
```

```
                1               5              10              15
            Asn Pro Phe

<210> SEQ ID NO 32
<211> LENGTH: 29
<212> TYPE: DNA
<213> ORGANISM: Staphylococcus aureus

<400> SEQUENCE: 32
aaggattcaa aaggagcggt atacattgc                                      29

<210> SEQ ID NO 33
<211> LENGTH: 29
<212> TYPE: DNA
<213> ORGANISM: Staphylococcus aureus

<400> SEQUENCE: 33
aaggatccta cctttcctc tagctgaac                                       29

<210> SEQ ID NO 34
<211> LENGTH: 283
<212> TYPE: PRT
<213> ORGANISM: Streptococcus pneumoniae srtA

<400> SEQUENCE: 34

Met Ser Arg Thr Lys Leu Arg Ala Leu Leu Gly Tyr Leu Leu Met Leu
    1               5                   10                  15
    Val Ala Cys Leu Ile Pro Ile Tyr Cys Phe Gly Gln Met Val Leu Gln
                    20                  25                  30
    Ser Leu Gly Gln Val Lys Gly His Ala Thr Phe Val Lys Ser Met Thr
                35                  40                  45
    Thr Glu Met Tyr Gln Glu Gln Asn His Ser Leu Ala Tyr Asn Gln
        50                  55                  60
    Arg Leu Ala Ser Gln Asn Arg Ile Val Asp Pro Phe Leu Ala Glu Gly
    65                  70                  75                  80
    Tyr Glu Val Asn Tyr Gln Val Ser Asp Asp Pro Asp Ala Val Tyr Gly
                    85                  90                  95
    Tyr Leu Ser Ile Pro Ser Leu Glu Ile Met Glu Pro Val Tyr Leu Gly
                    100                 105                 110
    Ala Asp Tyr His His Leu Gly Met Gly Leu Ala His Val Asp Gly Thr
                115                 120                 125
    Pro Leu Pro Leu Asp Gly Thr Gly Ile Arg Ser Val Ile Ala Gly His
        130                 135                 140
    Arg Ala Glu Pro Ser His Val Phe Phe Arg His Leu Asp Gln Leu Lys
    145                 150                 155                 160
    Val Gly Asp Ala Leu Tyr Tyr Asp Asn Gly Gln Glu Ile Val Glu Tyr
                    165                 170                 175
    Gln Met Met Asp Thr Glu Ile Ile Leu Pro Ser Glu Trp Glu Lys Leu
                    180                 185                 190
    Glu Ser Val Ser Ser Lys Asn Ile Met Thr Leu Ile Thr Cys Asp Pro
                195                 200                 205
    Ile Pro Thr Phe Asn Lys Arg Leu Leu Val Asn Phe Glu Arg Val Ala
        210                 215                 220
    Val Tyr Gln Lys Ser Asp Pro Gln Thr Ala Ala Val Ala Arg Val Ala
    225                 230                 235                 240
    Phe Thr Lys Glu Gly Gln Ser Val Ser Val Ala Thr Ser Gln Trp
                    245                 250                 255
    Leu Tyr Arg Gly Leu Val Val Leu Ala Phe Gly Ile Leu Phe Val
                    260                 265                 270
    Leu Trp Lys Leu Ala Arg Leu Leu Arg Gly Lys
                275                 280

<210> SEQ ID NO 35
<211> LENGTH: 296
<212> TYPE: PRT
<213> ORGANISM: Streptococcus pneumoniae srtB

<400> SEQUENCE: 35

Met Asp Asn Ser Arg Arg Ser Arg Lys Lys Gly Thr Lys Lys Lys
    1               5                   10                  15
    His Pro Leu Ile Leu Leu Leu Ile Phe Leu Val Gly Phe Ala Val Ala
```

```
            Ile Tyr Pro Leu Val Ser Arg Tyr Tyr Arg Ile Ser Asn Glu Val
                        35                  40                  45
            Ile Lys Glu Phe Asp Glu Thr Val Ser Gln Met Asp Lys Ala Glu Leu
             50                  55                  60
            Glu Glu Arg Trp Arg Leu Ala Gln Ala Phe Asn Ala Thr Leu Lys Pro
             65                  70                  75                  80
            Ser Glu Ile Leu Asp Pro Phe Thr Glu Gln Lys Lys Lys Gly Val
                            85                  90                  95
            Ser Glu Tyr Ala Asn Met Leu Lys Val His Glu Arg Ile Gly Tyr Val
                        100                 105                 110
            Glu Ile Pro Ala Ile Asp Gln Gly Ile Pro Met Tyr Val Gly Thr Ser
                        115                 120                 125
            Glu Asp Ile Leu Gln Lys Gly Ala Gly Leu Leu Glu Gly Ala Ser Leu
            130                 135                 140
            Pro Val Gly Gly Glu Asn Thr His Thr Val Ile Thr Ala His Arg Gly
            145                 150                 155                 160
            Leu Pro Thr Ala Glu Leu Phe Ser Gln Leu Asp Lys Met Lys Lys Gly
                            165                 170                 175
            Asp Ile Phe Tyr Leu His Val Leu Asp Gln Val Leu Ala Tyr Gln Val
                        180                 185                 190
            Asp Gln Ile Val Thr Val Glu Pro Asn Asp Phe Glu Pro Val Leu Ile
                        195                 200                 205
            Gln His Gly Glu Asp Tyr Ala Thr Leu Leu Thr Cys Thr Pro Tyr Met
            210                 215                 220
            Ile Asn Ser His Arg Leu Leu Val Arg Gly Lys Arg Ile Pro Tyr Thr
            225                 230                 235                 240
            Ala Pro Ile Ala Glu Arg Asn Arg Ala Val Arg Glu Arg Gly Gln Phe
                            245                 250                 255
            Trp Leu Trp Leu Leu Leu Gly Ala Met Ala Val Ile Leu Leu Leu Leu
                        260                 265                 270
            Tyr Arg Val Tyr Arg Asn Arg Arg Ile Val Lys Gly Leu Glu Lys Gln
                        275                 280                 285
            Leu Glu Gly Arg His Val Lys Asp
                290                 295

<210> SEQ ID NO 36
<211> LENGTH: 304
<212> TYPE: PRT
<213> ORGANISM: Streptococcus pneumoniae srtC

<400> SEQUENCE: 36

Met Leu Ile Lys Met Val Lys Thr Lys Lys Gln Lys Arg Asn Asn Leu
             1               5                  10                  15
            Leu Leu Gly Val Val Phe Phe Ile Gly Met Ala Val Met Ala Tyr Pro
                        20                  25                  30
            Leu Val Ser Arg Leu Tyr Tyr Arg Val Glu Ser Asn Gln Gln Ile Ala
                        35                  40                  45
            Asp Phe Asp Lys Glu Lys Ala Thr Leu Asp Glu Ala Asp Ile Asp Glu
             50                  55                  60
            Arg Met Lys Leu Ala Gln Ala Phe Asn Asp Ser Leu Asn Asn Val Val
             65                  70                  75                  80
            Ser Gly Asp Pro Trp Ser Glu Met Lys Lys Gly Arg Ala Glu
                            85                  90                  95
            Tyr Ala Arg Met Leu Glu Ile His Glu Arg Met Gly His Val Glu Ile
                        100                 105                 110
            Pro Val Ile Asp Val Asp Leu Pro Val Tyr Ala Gly Thr Ala Glu Glu
                        115                 120                 125
            Val Leu Gln Gln Gly Ala Gly His Leu Glu Gly Thr Ser Leu Pro Ile
            130                 135                 140
            Gly Gly Asn Ser Thr His Ala Val Ile Thr Ala His Thr Gly Leu Pro
            145                 150                 155                 160
            Thr Ala Lys Met Phe Thr Asp Leu Thr Lys Leu Lys Val Gly Asp Lys
                            165                 170                 175
            Phe Tyr Val His Asn Ile Lys Glu Val Met Ala Tyr Gln Val Asp Gln
                        180                 185                 190
            Val Lys Val Ile Glu Pro Thr Asn Phe Asp Asp Leu Leu Ile Val Pro
                        195                 200                 205
            Gly His Asp Tyr Val Thr Leu Leu Thr Cys Thr Pro Tyr Met Ile Asn
            210                 215                 220
            Thr His Arg Leu Leu Val Arg Gly His Arg Ile Pro Tyr Val Ala Glu
            225                 230                 235                 240
            Val Glu Glu Glu Phe Ile Ala Ala Asn Lys Leu Ser His Leu Tyr Arg
                            245                 250                 255
            Tyr Leu Phe Tyr Val Ala Val Gly Leu Ile Val Ile Leu Leu Trp Ile
                        260                 265                 270
            Ile Arg Arg Leu Arg Lys Lys Lys Lys Gln Pro Glu Lys Ala Leu Lys
```

```
            275                 280                 285
Ala Leu Lys Ala Ala Arg Lys Glu Val Lys Val Glu Asp Gly Gln Gln
        290                 295                 300
```

<210> SEQ ID NO 37
<211> LENGTH: 2732
<212> TYPE: DNA
<213> ORGANISM: Staphylococcus aureus

<400> SEQUENCE: 37

```
aaaaacccct tgtggtgtcac tgtacctgat aaagattcag caactttcat gtttatttca    60
aaacttctt  gcgcgtatgc gataatttgc tgatctaatc ttgccggttc aattgcaaat   120
aattgtgtaa ttacaattcc actttgataa gcttcttcaa ttaaatgcac accttcaatt   180
aaagctaatc cagtttatc  cctctcacgt ttctttttca gcttgttcgc ttgtttaatt   240
ctattatttt gtgcagaagt aatttgttcc attgatagct cctcgcttta tttttaaaaa   300
taaaatatt  aatcattaat aagatgaaaa catttgattg tatagttaat attaattaat   360
cgcttttatc actcataata tttcaaattg tataaatttc ttttatcgat actactacta   420
taaatcatac gccccaaaat atcattatta attctttttct tcttcaaaat aaatcaaaat   480
gatataattg atgattattt tcaaagcaca ttcaaatcaa actatgtttt agcaatttgt   540
tgttagcatg tttgtgttca ttaaaaaaac gaccatcatc ggtatcatgt atggtcgtta   600
caaaagctaa caataccaat tgtcataaca agtactgcaa cctctttaaa ttcaattatt   660
tcatgtaact atagcctata tcatatgtaa ttactttgtt atttataatc gggctacttt   720
catcttcatt tttacttcta acatgtttat gcgctgcttt aaagacatca gattttaacc   780
aatccgtaaa agcttgcttt gatttccaaa ctgttaaaat tttcacttca tcaaaatctt   840
cttgttctaa agtttgtgta acaaacatgc catcaaagcc ttcaatgtt  tcaatcccat   900
gtctcgtgta aaatcgttct ataatatctt tgctgttcc  ttttgttaac gtcagcctat   960
tttctgccat aaatttcata attatccctct tttctgttca acttaccttta attattttttg  1020
cgacaacaac aattcttttc gtcgtttcac tatatgcatc ttcgcacgtt gataaagtca  1080
ttattctatc ttttaccgtt acattaacat ctgaattaat tacagattta cgttttgtct  1140
catctaaaaa ttgttgataa tcttgatcat tttcaaaatc tgtacgtatg taattatctt  1200
tagtagtagt tttatatgca ctaaatactt gcaattgata tttaccatat ttattgtcaa  1260
attcaattat cttgtgtttt tcataaaacg attgctttaa ataatcttct aacacatcaa  1320
acatcgtatt atcaccgaca tggtgcccgt ataaatagt  attatgattt aaattcttca  1380
attcatttct aaaatccata aaaatactac ctttacgtcg atgttctcgc tcaaaatcta  1440
aatttaaata atcgtgattt gtcttacctt gtagtactgg taaatttaat gatgttcctg  1500
ataattttat ccatccaaca atgtctttat ttatttttttc aagtgattca aattgtggtc  1560
tcacatgttc ttgatgtttg ctcatcagca tttgaaattt ttgttgtaat ttctcataat  1620
ttgcgcgttc ttgcttgtct tcaatatatg tttgaacaat tttgtaacca aaaatgataa  1680
taattacaac caataaaatt tgtacaatag ttaaaaatcc cttcattctc ataaaaatcc  1740
tcttttatta acgacgtttc ttcagtcatc actaaaccag ttgttgtacc gttttagatt  1800
cgatttcgtt gactttgaca aattaagtaa attagcattg gaccaccgac aatcattaaa  1860
atagcattgg ctggaattttc taaggaggc tgtatcactc gtcctaataa atcagccact  1920
aacaatagcc atgcaccaat aactgtagaa aacggaataa gtactctgta attgcccca   1980
actagctttc taaccacatg tggcacaata atacctaaaa aggctagttg tccaacaatc  2040
gcaacagttg cacttgctaa aaatactgct aataaacctg ttaaccatct gtaacgatca  2100
atattaaaac cgatacttcg cgcttgtatg tcgtctaaat ttagtaaatt caatttaggg  2160
gacaaatagta atgttaatat taatcccaat aatgctgata ctgctaatat gtatacgtcg  2220
ctccatattt tcattgttaa gccttgagga attttcatta aaggtttg   agttaaaatt  2280
tctaaaacac catttaatat aacgaataac gcaacaccta ctaatatcat acttacagca  2340
ttgaatctaa atttagaatg caacaatata attattaaaa atggtattaa acctccaata  2400
aaacttaata atggtaagta aaagtacaat tgtggaataa acaacataca aagtgctctc  2460
attataagtg cacctgagga aacgccaatg atattcgcct ctgccaaatg attttgtagt  2520
gctgcttgta ataatgctcc agaaactgct aacattgcgc caaccatcaa tgcaattaat  2580
atacgtggca atcgcaaatc aatgattgaa tccactgctt cattgctacc agttgtaaat  2640
tttgtaaata ggtcattaaa tgacaattta attgtaccgg ttacaaacga aatataagca  2700
gttgcgatta aaatgactaa caaacataaa aa                                 2732
```

<210> SEQ ID NO 38
<211> LENGTH: 244
<212> TYPE: PRT
<213> ORGANISM: Staphylococcus aureus

<400> SEQUENCE: 38

```
Met Arg Met Lys Arg Phe Leu Thr Ile Val Gln Ile Leu Leu Val Val
 1               5                  10                  15
Ile Ile Ile Ile Phe Gly Tyr Lys Ile Val Gln Thr Tyr Ile Glu Asp
            20                  25                  30
Lys Gln Glu Arg Ala Asn Tyr Glu Lys Leu Gln Lys Phe Gln Met
        35                  40                  45
Leu Met Ser Lys His Gln Ala His Val Arg Pro Gln Phe Glu Ser Leu
    50                  55                  60
Glu Lys Ile Asn Lys Asp Ile Val Gly Trp Ile Lys Leu Ser Gly Thr
65                  70                  75                  80
Ser Leu Asn Tyr Pro Val Leu Gln Gly Lys Thr Asn His Asp Tyr Leu
                85                  90                  95
```

-continued

```
Asn Leu Asp Phe Glu Arg Glu His Arg Arg Lys Gly Ser Ile Phe Met
                100                 105                 110
Asp Phe Arg Asn Glu Leu Lys Ile Leu Asn His Asn Thr Ile Leu Tyr
            115                 120                 125
Gly His His Val Gly Asp Asn Thr Met Phe Asp Val Leu Glu Asp Tyr
        130                 135                 140
Leu Lys Gln Ser Phe Tyr Glu Lys His Lys Ile Ile Glu Phe Asp Asn
145                 150                 155                 160
Lys Tyr Gly Lys Tyr Gln Leu Gln Val Phe Ser Ala Tyr Lys Thr Thr
                165                 170                 175
Thr Lys Asp Asn Tyr Ile Arg Thr Asp Phe Glu Asn Asp Gln Asp Tyr
            180                 185                 190
Gln Gln Phe Leu Asp Glu Thr Lys Arg Lys Ser Val Ile Asn Ser Asp
        195                 200                 205
Val Asn Val Thr Val Lys Asp Lys Ile Met Thr Leu Ser Thr Cys Glu
210                 215                 220
Asp Ala Tyr Ser Glu Thr Thr Lys Arg Ile Val Val Ala Lys Ile
225                 230                 235                 240
Ile Lys Val Ser
```

<210> SEQ ID NO 39
<211> LENGTH: 621
<212> TYPE: DNA
<213> ORGANISM: Staphylococcus aureus

<400> SEQUENCE: 39

```
ttatttgact tctgtagcta caaagatttt acgttttcc caaacgcctg tcttttcatt      60
gtaatcatca caagtaatta atgttaattg tttatcttta ccttttgtt catctagaac     120
tcctacatct gtaggcttaa catctcttat acttgtcatt ttatacttac gtgtttcatt    180
accaacttta agtacacca tactaccttt tttggctgct ttaagatttg taaattgata    240
gttcggacgg tcaatgaaag tgtgtcctgc aattgaaata ttttgatcat ctagtgattc    300
attttcttct gcaaagctta caccctctatt taattgtca ggtgttgctg gtcctgbata    360
tactggttct taaatatcag catctggaat tcaatatag cctgccactt tcgatttatc    420
tttcggaatt tgaggtttag cttgctgctt tttatcttta ctcgcctgtt cttttacatt    480
tttatcatat tgttcaatct tttcatcttt atctttatcg tgaagataat tatcgatatg    540
tggtttagca acaaatatg ctgccactag ataagtacc acaccagcga ttgtcattaa     600
tcgatttgtc cattttttca t                                              621
```

<210> SEQ ID NO 40
<211> LENGTH: 2732
<212> TYPE: DNA
<213> ORGANISM: Staphylococcus aureus

<400> SEQUENCE: 40

```
tgaaataaac atgaaagttg ctgaatcttt atcaggtaca gtgacaccac aagggttttt       60
atttgcaatt gaaccggcaa gattagatca gcaaattatc gcatacgcgc aagaagtttt      120
aattgaaggt gtgcatttaa ttgaagaagc ttatcaaagt ggaattgtaa ttacacaatt      180
aattaaacaa gcgaacaagc taaaaagaa acgtgagagg gataaaactg gattagcttt      240
ttttttaaaaa taaagcgagg agctatcaat ggaacaaatt acttctgcac aaaataatag     300
attaattaat attaactata caatcaaatg ttttcatctt attaatgatt aatattttta     360
tagtagtagt atcgataaaa gaaatttata caatttgaaa tattatgagt gataaaagcg     420
attttgattt attttgaaga agaaaagaat taataatgat attttgggcc gtatgattta     480
acaaattgct aaaacatagt ttgatttgaa tgtgctttga aataatcat caattatatc      540
taacgaccat acatgatacc gatgatggtc gttttttaa tgaacacaaa catgctaaca      600
aataattgaa tttaaagagg ttgcagtact tgttatgaca attggtattg ttagcttttg     660
aaagtagccc gattataaat aacaaagtaa ttacatatga tataggctat agttacatga     720
ggttaaaatc tgatgtcttt aaagcagcgc ataaacatgt tagaagtaaa aatgaagatg     780
aagattttga tgaagtgaaa attttaacag tttggaaatc aaagcaagct tttacggatt     840
atgggattga acattagaa ggctttgatg gcatgtttgt tacacaaact ttagaacaag     900
ataggctgac gttaacaaaa ggaacagcaa agatatatt agaacgattt tacacgagac     960
caaaaataat taaggtaagt taaacagaaa agaggataat atgaaattt atggcagaaa    1020
tgacttatc aacgtgcgaa gatgcatata tgaaacgac gaaaagaatt gttgttgtcg    1080
agacaaaacg taaatctgta attaattcag atgttaatgt aacggtaaaa gatagaataa    1140
aagataatta catacgtaca gattttgaaa atgatcaaga ttatcaacaa ttttttagatg    1200
ttgacaataa atatggtaaa tatcaattgc aagtatttag tgcatataaa actactacta    1260
ttgatgtgtt agaagattat ttaaagcaat cgttttatga aaaacacaag ataattgaat    1320
tgaagaattt aaatcataat actattttat acgggcacca tgtcggtgat aatacgatgt    1380
tagatttga gcgagaacat cgacgtaaag gtagtatttt tatggatttt agaaatgaat    1440
caggaacatc attaaattat ccagtactac aagtaagac aaatcacgat tatttaaatt    1500
gaccacaatt tgaatcactt gaaaaaataa ataagacat tgttggatgg ataaaattat    1560
attatgagaa attacaacaa aaatttcaa tgctgatgag caaacatcaa gaacatgtga    1620
ttatcatttt tggttacaaa attgttcaaa catatattga agacaagcaa gaacgcgcaa    1680
ggattttat gagaatgaag cgattttaa ctattgtaca aatttattg gttgtaatta     1740
aatctaaaac ggtacaacaa ctggtttagt gatgactgaa gaaacgtcgt taataaaaga    1800
tttaatgatt gtcggtggtc caatgctaat ttacttaatt tgtcaaagtc aacgaaatcg    1860
```

```
agtggctgat ttattaggac gagtgataca gcctccttta gaaattccag ccaatgctat    1920
tgggggcaat tacagagtac ttattccgtt ttctacagtt attggtgcat ggctattgtt    1980
gattgttgga caactagcct tttttaggtat tattgtgcca catgtggtta gaaagctagt   2040
tgatcgttac agatggttaa caggtttatt agcagtattt ttagcaagtg caactgttgc    2100
ccctaaattg aatttactaa atttagacga catacaagcg cgaagtatcg gtttttaatat   2160
cgacgtatac atattagcag tatcagcatt attgggatta atattaacat tactattgtc    2220
aattttaact caaaaccctt taatgaaaat tcctcaaggc ttaacaatga aaatatggag    2280
tgctgtaagt atgatattag taggtgttgc gttattcgta ttattaaatg gtgttttaga    2340
tattggaggt ttaataccat tttttaataat tatattgttg cattctaaat ttagattcaa    2400
gagagcactt tgtatgttgt ttattccaca attgtacttt tacttaccat tattaagttt    2460
actacaaaat cctttggcag aggcgaatat cattggcgtt tcctcaggtg cacttataat    2520
attaattgca ttgatggttg gcgcaatgtt agcagtttct ggagcattat tacaagcagc    2580
atttacaact ggtagcaatg aagcagtgga ttcaatcatt gatttgcgat tgccacgtat    2640
tgcttatatt tcgtttgtaa ccggtacaat taaattgtca tttaatgacc tatttacaaa    2700
tttttatgtt tgttagtcat tttaatcgca ac                                  2732
```